(12) United States Patent
Rodriguez-Navarro

(10) Patent No.: US 12,740,799 B2
(45) Date of Patent: Sep. 22, 2026

(54) DIRECTABLE TRACTION SYSTEMS AND METHODS

(71) Applicant: Levita Magnetics International Corp., Mountain View, CA (US)

(72) Inventor: Alberto Rodriguez-Navarro, San Francisco, CA (US)

(73) Assignee: LEVITA MAGNETICS INTERNATIONAL CORP., Mountain View, CA (US)

( * ) Notice: Subject to any disclaimer, the term of this patent is extended or adjusted under 35 U.S.C. 154(b) by 93 days.

(21) Appl. No.: 18/969,128

(22) Filed: Dec. 4, 2024

(65) Prior Publication Data

US 2025/0312053 A1 Oct. 9, 2025

Related U.S. Application Data

(63) Continuation of application No. 17/332,876, filed on May 27, 2021, now Pat. No. 12,185,962, which is a (Continued)

(51) Int. Cl.

*A61B 17/29* (2006.01)
*A61B 17/02* (2006.01)

(Continued)

(52) U.S. Cl.

CPC .......... *A61B 17/29* (2013.01); *A61B 17/0218* (2013.01); *A61B 17/122* (2013.01);

(Continued)

(58) Field of Classification Search

CPC . A61B 17/29; A61B 17/0218; A61B 17/1285; A61B 34/73; A61B 2017/00283;

(Continued)

(56) References Cited

U.S. PATENT DOCUMENTS

| | | | |
|---|---|---|---|
| 2,678,228 | A | 5/1954 | Gerhardt |
| 2,863,444 | A | 12/1958 | Winsten |

(Continued)

FOREIGN PATENT DOCUMENTS

| | | | |
|---|---|---|---|
| AU | 2016204942 | A1 | 2/2017 |
| CA | 2 748 471 | A1 | 7/2010 |

(Continued)

OTHER PUBLICATIONS

Aesculap, "Endoscopic Vascular surgery in the pelvic region," B/Braun, Aesculap AG & Co.KG, Catalog, 48 pages, 2006, Copy Unavailable, document can be accessed at https://docplayer.net/22042174-Aesculap-endoscopic-technology-endoscopic-vascular-surgery-in-the-pelvic-region.html.

(Continued)

*Primary Examiner* — Brooke Labranche
(74) *Attorney, Agent, or Firm* — Cooley LLP

(57) ABSTRACT

Described here are methods, systems, and devices, useful for minimally invasive surgical procedures. The methods may include introducing a grasper through an opening into an abdominal cavity, grasping a portion of a left lobe of a liver with the grasper, rotating the grasper towards a control element located outside the abdominal cavity by applying a magnetic field to the grasper across a body wall, and moving the control element over a set of ribs such that the liver bends into a folded configuration.

15 Claims, 18 Drawing Sheets

Related U.S. Application Data continuation of application No. 15/926,578, filed on Mar. 20, 2018, now Pat. No. 11,020,137.

(60) Provisional application No. 62/473,841, filed on Mar. 20, 2017.

(51) Int. Cl.
*A61B 17/122* (2006.01)
*A61B 17/128* (2006.01)
*A61B 34/00* (2016.01)
*A61B 17/00* (2006.01)

(52) U.S. Cl.
CPC .......... *A61B 17/1285* (2013.01); *A61B 34/73* (2016.02); *A61B 2017/00283* (2013.01); *A61B 2017/00876* (2013.01); *A61B 2017/2931* (2013.01); *A61B 2017/2934* (2013.01); *A61B 2017/2947* (2013.01)

(58) Field of Classification Search
CPC .. A61B 2017/00876; A61B 2017/2931; A61B 2017/2934; A61B 2017/2947; A61B 17/122
See application file for complete search history.

(56) References Cited

U.S. PATENT DOCUMENTS 3,146,381 A 8/1964 Louis
3,674,014 A 7/1972 Tillander
3,789,285 A 1/1974 Nishizawa
3,794,091 A 2/1974 Ersek et al.
4,364,377 A 12/1982 Smith
4,380,999 A 4/1983 Healy
4,706,668 A 11/1987 Backer
4,756,312 A 7/1988 Epley
4,901,405 A 2/1990 Grover et al.
4,915,435 A 4/1990 Levine
4,968,136 A 11/1990 Lim et al.
4,971,067 A 11/1990 Bolduc et al.
4,976,723 A 12/1990 Schad
4,997,436 A 3/1991 Oberlander
5,002,557 A 3/1991 Hasson
5,154,189 A 10/1992 Oberlander
5,156,608 A 10/1992 Troidl et al.
5,156,609 A 10/1992 Nakao et al.
5,282,806 A 2/1994 Haber et al.
5,300,081 A 4/1994 Young et al.
5,304,183 A 4/1994 Gourlay et al.
5,304,185 A 4/1994 Taylor
5,307,805 A 5/1994 Byrne
5,340,360 A 8/1994 Stefanchik
5,397,325 A 3/1995 Della Badia
5,411,535 A 5/1995 Fujii et al.
5,415,160 A 5/1995 Ortiz et al.
5,417,701 A 5/1995 Holmes
5,449,361 A 9/1995 Preissman
5,449,365 A 9/1995 Green et al.
5,450,842 A 9/1995 Tovey et al.
5,458,603 A 10/1995 Futch, Sr.
5,458,693 A 10/1995 Codorniu
5,465,711 A 11/1995 Moll et al.
5,496,317 A 3/1996 Goble et al.
5,499,986 A 3/1996 Dimarco
5,529,568 A 6/1996 Rayman
5,538,098 A 7/1996 Sparhawk
5,567,274 A 10/1996 Funk et al.
5,569,274 A 10/1996 Rapacki et al.
5,593,379 A 1/1997 Rayman
5,595,562 A 1/1997 Grier
5,654,864 A 8/1997 Ritter et al.
5,665,100 A 9/1997 Yoon
5,681,260 A 10/1997 Ueda et al.
5,728,121 A 3/1998 Bimbo et al.
5,733,292 A 3/1998 Gustilo et al.
5,749,881 A 5/1998 Sackier et al.
5,766,189 A 6/1998 Matsuno
5,782,748 A 7/1998 Palmer et al.
5,797,911 A 8/1998 Sherman et al.
5,797,939 A 8/1998 Yoon
5,824,041 A 10/1998 Lenker et al.
5,848,969 A 12/1998 Panescu et al.
5,849,015 A 12/1998 Haywood et al.
5,888,196 A 3/1999 Bonutti
5,893,873 A 4/1999 Rader et al.
5,933,926 A 8/1999 Reiter
6,015,414 A 1/2000 Werp et al.
6,017,358 A 1/2000 Yoon et al.
6,096,038 A 8/2000 Michelson
6,099,537 A 8/2000 Sugai et al.
6,099,550 A 8/2000 Yoon
6,123,657 A 9/2000 Ishikawa et al.
6,126,647 A 10/2000 Posey et al.
6,127,757 A 10/2000 Swinbanks
6,165,180 A 12/2000 Cigaina et al.
6,173,715 B1 1/2001 Sinanan et al.
6,212,419 B1 4/2001 Blume et al.
6,216,028 B1 4/2001 Haynor et al.
6,241,671 B1 6/2001 Ritter et al.
6,311,082 B1 10/2001 Creighton, IV et al.
6,315,709 B1 11/2001 Garibaldi et al.
6,330,467 B1 12/2001 Creighton, IV et al.
6,340,365 B2 1/2002 Dittrich et al.
6,358,196 B1 3/2002 Rayman
6,371,973 B1 4/2002 Tepper
6,398,791 B1 6/2002 Que et al.
6,399,146 B1 6/2002 Harris et al.
6,401,723 B1 6/2002 Garibaldi et al.
6,440,133 B1 8/2002 Beale et al.
6,458,146 B1 10/2002 Kramer
6,459,924 B1 10/2002 Creighton, IV et al.
6,464,710 B1 10/2002 Foster
6,488,615 B1 12/2002 Mitchiner et al.
6,523,919 B1 2/2003 Israelsen et al.
6,537,196 B1 3/2003 Creighton, IV et al.
6,551,304 B1 4/2003 Whalen et al.
6,594,517 B1 7/2003 Nevo
6,630,879 B1 10/2003 Creighton, IV et al.
6,632,229 B1 10/2003 Yamanouchi
6,641,595 B1 11/2003 Moran et al.
6,656,199 B1 12/2003 Lafontaine
6,677,752 B1 1/2004 Creighton, IV et al.
6,689,119 B1 2/2004 Di Caprio et al.
6,702,804 B1 3/2004 Ritter et al.
6,705,989 B2 3/2004 Cuschieri et al.
6,719,765 B2 4/2004 Bonutti
6,761,681 B2 7/2004 Schmid et al.
6,786,219 B2 9/2004 Garibaldi et al.
6,817,364 B2 11/2004 Garibaldi et al.
6,824,511 B1 11/2004 Bell et al.
6,916,314 B2 7/2005 Schneider et al.
7,017,584 B2 3/2006 Garibaldi et al.
7,094,245 B2 8/2006 Adams et al.
7,169,104 B2 1/2007 Ueda et al.
7,182,089 B2 2/2007 Ries
7,182,775 B2 2/2007 De Guillebon et al.
7,189,198 B2 3/2007 Harburn et al.
7,264,584 B2 9/2007 Ritter et al.
7,300,400 B2 11/2007 Brown
7,311,107 B2 12/2007 Harel et al.
7,313,429 B2 12/2007 Creighton, IV et al.
7,314,063 B2 1/2008 Egli
7,341,063 B2 3/2008 Garbibaldi et al.
7,344,553 B2 3/2008 Opolski et al.
7,390,298 B2 6/2008 Chu
7,416,335 B2 8/2008 Munger
7,429,259 B2 9/2008 Cadeddu et al.
7,431,726 B2 10/2008 Spence et al.
7,566,038 B2 7/2009 Scott et al.
7,618,435 B2 11/2009 Opolski
7,686,827 B2 3/2010 Hushka
7,691,103 B2 4/2010 Fernandez et al.
7,691,731 B2 4/2010 Bet et al.

(56) References Cited

U.S. PATENT DOCUMENTS 7,708,756 B2 5/2010 Nobis et al.
7,736,356 B2 6/2010 Cooper et al.
7,766,810 B2 8/2010 Ohdaira
7,769,427 B2 8/2010 Shachar
7,772,950 B2 8/2010 Tunay
7,774,046 B2 8/2010 Werp et al.
7,780,054 B2 8/2010 Wales
7,799,050 B2 9/2010 Hensley et al.
7,837,612 B2 11/2010 Gill et al.
7,850,591 B2 12/2010 Spector
7,942,885 B2 5/2011 Sixto, Jr. et al.
7,963,903 B2 6/2011 Ghiron et al.
7,966,059 B2 6/2011 Creighton, IV et al.
7,967,830 B2 6/2011 Ayala et al.
8,038,612 B2 10/2011 Paz
8,043,290 B2 10/2011 Harrison et al.
8,057,472 B2 11/2011 Walker et al.
8,060,184 B2 11/2011 Hastings et al.
8,066,715 B2 11/2011 Ducharme
8,074,657 B2 12/2011 Scott et al.
8,082,035 B2 12/2011 Glukhovsky
8,133,254 B2 3/2012 Dumbauld et al.
8,136,888 B2 3/2012 Suzuki et al.
8,137,268 B2 3/2012 Van Lue
8,157,149 B2 4/2012 Olson et al.
8,187,286 B2 5/2012 Jugenheimer et al.
8,197,494 B2 6/2012 Jaggi et al.
8,226,690 B2 7/2012 Altarac et al.
8,235,272 B2 8/2012 Nicholas et al.
8,241,322 B2 8/2012 Whitman et al.
8,246,529 B2 8/2012 Riehl et al.
8,252,021 B2 8/2012 Boulnois et al.
8,267,854 B2 9/2012 Asada et al.
8,301,226 B2 10/2012 Csavoy et al.
8,303,495 B2 11/2012 Ducharme
8,313,497 B2 11/2012 Walberg et al.
8,316,861 B2 11/2012 Brewer et al.
8,316,862 B2 11/2012 Shapiro et al.
8,333,695 B2 12/2012 Cuschieri
8,343,171 B2 1/2013 Farritor et al.
8,360,972 B2 1/2013 Paz
8,364,277 B2 1/2013 Glukhovsky
8,377,044 B2 2/2013 Coe et al.
8,382,754 B2 2/2013 Odom et al.
8,403,916 B2 3/2013 Prescott
8,409,076 B2 4/2013 Pang et al.
8,480,668 B2 7/2013 Fernandez et al.
8,491,626 B2 7/2013 Roy et al.
8,517,931 B2 8/2013 Minnelli et al.
8,518,057 B2 8/2013 Walberg et al.
8,556,919 B2 10/2013 Aguirre et al.
8,579,787 B2 11/2013 Shapiro et al.
8,585,685 B2 11/2013 Hagg
8,602,981 B2 12/2013 Deutch
8,608,773 B2 12/2013 Tierney et al.
8,623,011 B2 1/2014 Spivey
8,628,529 B2 1/2014 Aldridge et al.
8,636,762 B2 1/2014 Whitman et al.
8,637,818 B2 1/2014 Balakin
8,685,043 B2 4/2014 Jugenheimer et al.
8,758,394 B2 6/2014 Zimmerling et al.
8,764,769 B1 7/2014 Rodriguez-Navarro et al.
8,790,245 B2 7/2014 Rodriguez Fernandez et al.
8,820,602 B2 9/2014 Walberg et al.
8,827,891 B2 9/2014 Roberts
8,828,024 B2 9/2014 Farritor et al.
8,894,574 B2 11/2014 Ellman
8,926,656 B2 1/2015 Palermo et al.
8,944,997 B2 2/2015 Fernandez et al.
8,968,332 B2 3/2015 Farritor et al.
8,968,356 B2 3/2015 Mueller
9,011,468 B2 4/2015 Ketai et al.
9,033,957 B2 5/2015 Cadeddu et al.
9,044,256 B2 6/2015 Cadeddu et al.
9,339,285 B2 5/2016 Rodriguez-Navarro et al.
9,386,973 B2 7/2016 Deutch
9,561,031 B2 2/2017 Heinrich et al.
9,627,120 B2 4/2017 Scott et al.
9,844,391 B2 12/2017 Rodriguez Fernandez et al.
9,962,148 B2 5/2018 Deutch
9,974,546 B2 5/2018 Rodriguez Fernandez et al.
10,010,370 B2 7/2018 Rodriguez-Navarro et al.
10,130,381 B2 11/2018 Rodriguez-Navarro et al.
10,143,459 B2 12/2018 Heftman
10,335,134 B2 7/2019 Deutch
10,537,348 B2 1/2020 Rodriguez-Navarro et al.
10,905,511 B2 2/2021 Rodriguez-Navarro et al.
11,020,137 B2 6/2021 Rodriguez-Navarro
11,357,525 B2 6/2022 Rodriguez-Navarro et al.
11,413,025 B2 8/2022 Deutch
11,413,026 B2 8/2022 Deutch
11,583,354 B2 2/2023 Rodriguez-Navarro et al.
11,730,476 B2 8/2023 Rodriguez-Navarro et al.
11,751,965 B2 9/2023 Rodriguez-Navarro et al.
12,171,433 B2 12/2024 Rodriguez-Navarro et al.
12,185,962 B2 1/2025 Rodriguez-Navarro
2001/0038683 A1 11/2001 Ritter et al.
2002/0100486 A1 8/2002 Creighton, IV et al.
2002/0107533 A1 8/2002 Solingen
2002/0116043 A1 8/2002 Garibaldi et al.
2002/0173805 A1 11/2002 Matsuno et al.
2003/0114731 A1 6/2003 Cadeddu et al.
2003/0125752 A1 7/2003 Werp et al.
2003/0181945 A1 9/2003 Opolski et al.
2003/0208185 A1 11/2003 Sheffer et al.
2004/0044295 A1 3/2004 Reinert et al.
2004/0050395 A1 3/2004 Ueda et al.
2004/0064153 A1 4/2004 Creighton, IV et al.
2004/0068173 A1 4/2004 Viswanathan
2004/0158972 A1 8/2004 Creighton, IV et al.
2004/0172057 A1 9/2004 Guillebon et al.
2004/0186347 A1 9/2004 Shose et al.
2004/0199074 A1 10/2004 Ritter et al.
2004/0230100 A1 11/2004 Shluzas
2004/0249262 A1 12/2004 Werp et al.
2005/0080440 A1 4/2005 Durgin et al.
2005/0085696 A1 4/2005 Uchiyama et al.
2005/0113628 A1 5/2005 Creighton, IV et al.
2005/0131390 A1 6/2005 Heinrich et al.
2005/0165449 A1 7/2005 Cadeddu et al.
2005/0220583 A1 10/2005 Lutz
2005/0250988 A1 11/2005 Ewers et al.
2005/0251183 A1 11/2005 Buckman et al.
2005/0277975 A1 12/2005 Saadat et al.
2006/0015178 A1 1/2006 Moaddeb et al.
2006/0074448 A1 4/2006 Harrison et al.
2006/0079897 A1 4/2006 Harrison et al.
2006/0089633 A1 4/2006 Bleich et al.
2006/0116714 A1 6/2006 Sepetka et al.
2006/0149135 A1 7/2006 Paz
2006/0152309 A1 7/2006 Mintchev et al.
2006/0228421 A1 10/2006 Seeney et al.
2006/0241691 A1 10/2006 Wilk
2006/0247522 A1 11/2006 Mcgee
2006/0276738 A1 12/2006 Becker
2006/0293566 A1 12/2006 Brown
2007/0004958 A1 1/2007 Ohdaira
2007/0016010 A1 1/2007 Creighton, IV et al.
2007/0027458 A1 2/2007 Sixto, Jr. et al.
2007/0043359 A1 2/2007 Altarac et al.
2007/0073102 A1 3/2007 Matsuno et al.
2007/0135678 A1 6/2007 Suzuki
2007/0135685 A1 6/2007 Cuschieri
2007/0135802 A1 6/2007 Suzuki
2007/0135803 A1 6/2007 Belson
2007/0156028 A1 7/2007 Van Lue et al.
2007/0191670 A1 8/2007 Spector
2007/0221233 A1 9/2007 Kawano et al.
2007/0255273 A1 11/2007 Fernandez et al.
2007/0270629 A1 11/2007 Charles
2007/0282311 A1 12/2007 Scott et al.
2008/0081883 A1 4/2008 King, II et al.
2008/0097496 A1* 4/2008 Chang .................... A61F 5/003 606/1

(56) References Cited

U.S. PATENT DOCUMENTS

2008/0108860 A1 5/2008 Bell et al.
2008/0134474 A1 6/2008 Uryasov
2008/0171907 A1 7/2008 Long et al.
2008/0243106 A1 10/2008 Coe et al.
2008/0249534 A1 10/2008 Gruber et al.
2008/0269779 A1 10/2008 Cadeddu et al.
2008/0300458 A1 12/2008 Kim et al.
2009/0004324 A1 1/2009 Viel et al.
2009/0005636 A1 1/2009 Pang et al.
2009/0026771 A1 1/2009 Bevington et al.
2009/0043246 A1 2/2009 Dominguez
2009/0054909 A1 2/2009 Farritor et al.
2009/0062772 A1 3/2009 Wakeford et al.
2009/0076536 A1 3/2009 Rentschler et al.
2009/0137984 A1 5/2009 Minnelli
2009/0187074 A1 7/2009 Saadat et al.
2009/0192344 A1 7/2009 Bakos et al.
2009/0222029 A1 9/2009 Gordin et al.
2009/0267717 A1 10/2009 Baskett
2009/0318762 A1 12/2009 Segawa et al.
2010/0010306 A1 1/2010 Kawano et al.
2010/0030026 A1 2/2010 Uchiyama et al.
2010/0036394 A1 2/2010 Mintz et al.
2010/0036399 A1 2/2010 Viola
2010/0081876 A1 4/2010 Linenkugel et al.
2010/0105984 A1 4/2010 Brewer et al.
2010/0113872 A1 5/2010 Asada et al.
2010/0114126 A1 5/2010 Neff
2010/0137845 A1 6/2010 Ramstein et al.
2010/0145147 A1 6/2010 Pinsky et al.
2010/0152539 A1 6/2010 Ghabrial et al.
2010/0160739 A1 6/2010 Van Lue
2010/0168523 A1 7/2010 Ducharme
2010/0174234 A1 7/2010 Werp et al.
2010/0193566 A1 8/2010 Scheib et al.
2010/0204727 A1 8/2010 Dominguez
2010/0217245 A1 8/2010 Prescott
2010/0237206 A1 9/2010 Barker
2010/0256636 A1 10/2010 Fernandez et al.
2010/0268254 A1 10/2010 Golden et al.
2010/0298645 A1 11/2010 Deutch
2011/0040152 A1 2/2011 Kim et al.
2011/0054306 A1 3/2011 Del Nido et al.
2011/0087223 A1 4/2011 Spivey
2011/0087224 A1 4/2011 Cadeddu et al.
2011/0087249 A1 4/2011 Rodriques et al.
2011/0105848 A1 5/2011 Sadovsky et al.
2011/0121050 A1 5/2011 Nicholas et al.
2011/0130787 A1 6/2011 Cinquin et al.
2011/0184440 A1 7/2011 Saldinger
2011/0215888 A1 9/2011 Abbott et al.
2011/0230726 A1 9/2011 Viola
2011/0230869 A1 9/2011 Altamirano
2011/0276941 A1 11/2011 Oi
2011/0283822 A1 11/2011 Cadeddu et al.
2011/0284014 A1 11/2011 Cadeddu et al.
2011/0285488 A1 11/2011 Scott et al.
2011/0295067 A1 12/2011 Rodriguez Fernandez et al.
2011/0306840 A1 12/2011 Allen et al.
2011/0313415 A1 12/2011 Fernandez et al.
2012/0008535 A1 1/2012 Kuehnel
2012/0016362 A1 1/2012 Heinrich et al.
2012/0035416 A1 2/2012 Fernandez et al.
2012/0053402 A1 3/2012 Conlon et al.
2012/0053406 A1 3/2012 Conlon et al.
2012/0065627 A1 3/2012 Ghabrial et al.
2012/0078292 A1 3/2012 Banju
2012/0085358 A1 4/2012 Cadeddu et al.
2012/0101488 A1 4/2012 Aldridge et al.
2012/0116148 A1 5/2012 Weinberg et al.
2012/0227748 A1 9/2012 Sanders
2012/0238796 A1 9/2012 Conlon
2012/0330089 A1 12/2012 Ritter et al.
2013/0030462 A1 1/2013 Keating et al.
2013/0066304 A1 3/2013 Belson et al.
2013/0085341 A1 4/2013 Nobis et al.
2013/0090666 A1 4/2013 Hess et al.
2013/0109267 A1 5/2013 Schweikardt et al.
2013/0110128 A1 5/2013 Schostek et al.
2013/0123828 A1 5/2013 Culmer et al.
2013/0158348 A1 6/2013 Nobis et al.
2013/0158523 A1 6/2013 Bergs et al.
2013/0158659 A1 6/2013 Bergs et al.
2013/0158660 A1 6/2013 Bergs et al.
2013/0172672 A1 7/2013 Iddan et al.
2013/0172906 A1 7/2013 Olson et al.
2013/0226226 A1 8/2013 Garrison et al.
2013/0245356 A1 9/2013 Fernandez et al.
2013/0253256 A1 9/2013 Griffith et al.
2013/0253275 A1 9/2013 Ransden et al.
2013/0253550 A1 9/2013 Beisel et al.
2013/0267788 A1 10/2013 Duan et al.
2013/0289579 A1 10/2013 Yeung et al.
2013/0289617 A1 10/2013 Suzuki et al.
2013/0289768 A1 10/2013 Yeung et al.
2013/0303851 A1 11/2013 Griffith et al.
2014/0066695 A1 3/2014 Deutch
2014/0084761 A1 3/2014 Scott et al.
2014/0135616 A1 5/2014 Stein et al.
2014/0176797 A1 6/2014 Silva et al.
2014/0187857 A1 7/2014 Wilson et al.
2014/0243586 A1 8/2014 Rohaninejad et al.
2014/0243597 A1 8/2014 Weisenburgh, II et al.
2014/0257370 A1 9/2014 Taylor et al.
2014/0276335 A1 9/2014 Pate
2014/0277104 A1 9/2014 Rodriguez-Navarro et al.
2014/0350574 A1 11/2014 Farritor et al.
2014/0358162 A1 12/2014 Valdastri et al.
2014/0358229 A1 12/2014 Bergs et al.
2015/0012010 A1 1/2015 Adler et al.
2015/0018614 A1 1/2015 Duan et al.
2015/0141750 A1 5/2015 Iddan et al.
2016/0038135 A1 2/2016 Deutch
2016/0120613 A1 5/2016 Cadeddu et al.
2018/0271603 A1 9/2018 Nir et al.
2018/0296289 A1 10/2018 Rodriguez-Navarro et al.
2018/0325604 A1 11/2018 Atarot et al.
2019/0269394 A1 9/2019 Deutch
2019/0350575 A1 11/2019 Deutch
2021/0290330 A1 9/2021 Rodriguez-Navarro et al.
2023/0021246 A1 1/2023 Rodriguez-Navarro et al.
2023/0106676 A1 4/2023 Deutch
2023/0277266 A1 9/2023 Rodriguez-Navarro et al.
2024/0156556 A1 5/2024 Rodriguez-Navarro et al.

FOREIGN PATENT DOCUMENTS

CA 2733465 A1 9/2011
CN 2244381 Y 1/1997
CN 101090672 A 12/2007
CN 201079412 Y 7/2008
CN 201091596 Y 7/2008
CN 101534725 A 9/2009
CN 102068288 A 5/2011
CN 102355865 A 2/2012
CN 203953720 U 11/2014
DE 42 12 430 A1 10/1993
DE 19 534 618 A1 3/1997
DE 10 2005 006 705 A1 8/2006
DE 10-2010-010417 A1 9/2011
EP 1 797 823 A1 6/2007
EP 1 972 284 A2 9/2008
EP 2 012 697 A2 1/2009
EP 2 355 699 A2 8/2011
EP 2 366 357 A1 9/2011
EP 2 381 873 A2 11/2011
EP 2 391 277 A0 12/2011
EP 1 942 810 B1 8/2012
EP 2 571 443 A2 3/2013
EP 2 595 548 5/2013
EP 2 842 511 A1 3/2015
JP 09-192137 A 7/1997
JP 2004-357816 A 12/2004
JP 2005-021576 A 1/2005

(56) References Cited

FOREIGN PATENT DOCUMENTS

| | | | |
|---|---|---|---|
| JP | 4320214 | B2 | 8/2009 |
| JP | 2009-538699 | A | 11/2009 |
| WO | WO-00/51500 | A1 | 9/2000 |
| WO | WO-2005/004734 | A1 | 1/2005 |
| WO | WO-2005/032370 | A1 | 4/2005 |
| WO | WO-2006/071120 | A1 | 7/2006 |
| WO | WO-2007/067231 | A1 | 6/2007 |
| WO | WO-2007/130382 | A2 | 11/2007 |
| WO | WO-2007/142977 | A2 | 12/2007 |
| WO | WO-2007/143162 | A2 | 12/2007 |
| WO | WO-2007/143170 | A2 | 12/2007 |
| WO | WO-2008/039237 | A1 | 4/2008 |
| WO | WO-2008/085919 | A2 | 7/2008 |
| WO | WO-2008/131128 | A1 | 10/2008 |
| WO | WO-2009/008865 | A1 | 1/2009 |
| WO | WO-2009/019288 | A2 | 2/2009 |
| WO | WO-2009/070743 | A1 | 6/2009 |
| WO | WO-2010/056716 | A2 | 5/2010 |
| WO | WO-2010/077561 | A1 | 7/2010 |
| WO | WO-2010/083480 | A2 | 7/2010 |
| WO | WO-2010/089635 | A1 | 8/2010 |
| WO | WO-2011/044468 | A2 | 4/2011 |
| WO | WO-2011/044471 | A2 | 4/2011 |
| WO | WO-2011/091483 | A1 | 8/2011 |
| WO | WO-2011/146691 | A2 | 11/2011 |
| WO | WO2011/146698 | A2 | 11/2011 |
| WO | WO-2011/146709 | A2 | 11/2011 |
| WO | WO-2012/010910 | A1 | 1/2012 |
| WO | WO-2012/031114 | A2 | 3/2012 |
| WO | WO-2012/033925 | A1 | 3/2012 |
| WO | WO-2012/048102 | A2 | 4/2012 |
| WO | WO-2013/096470 | A1 | 6/2013 |
| WO | WO-2014/133751 | A1 | 9/2014 |
| WO | WO-2014/159023 | A1 | 10/2014 |
| WO | WO-2014/163872 | A1 | 10/2014 |
| WO | WO-2015/112645 | A1 | 7/2015 |
| WO | WO-2015/142953 | A1 | 9/2015 |
| WO | WO-2016/168380 | A1 | 10/2016 |

OTHER PUBLICATIONS

Best, S.L. et al. (2010). "Development of magnetic anchoring and guidance systems for minimally invasive surgery," Indian J. of Urology 26:418-422.

Best, S.L. et al. (2010). "Solo Surgeon LESS Nephrectomy Facilitated by New Generation Magnetically Anchored and Guided (MAGS) Camera," World Congress of Endourology, PS38-14, Chicago IL, Sep. 2010.

Best, S.L. et al. (2010). "MAGS Instrumentation for Less/Notes: Lack of Histologic Damage After Prolonged Magnetic Coupling Across the Abdominal Wall," World Congress of Endourology, PS2-4, Chicago IL, Sep. 2010.

Best, S.L. et al. (2008). "Maximizing Coupling Strength of Magnetically Anchored Surgical Instruments: How Thick Can We Go?" Surgical Endoscopy 25:153-159.

Cadeddu, J.A. et al. (2002). "Transabdominal magnetic anchoring system for trocar-less laparoscopic surgery," J. of Urology, vol. 167, No. 4, Supplement, Abstract No. 16, 1 total page.

Cadeddu, J. et al. (2009). "Novel Magnetically Guided Intraabdominal Camera to Facilitate Laparoendoscopic Single Site Surgery: Initial Human Experience," Surgical Endoscopy 23:1894-1899.

Corrected Notice of Allowability mailed on Jul. 12, 2023, for U.S. Appl. No. 17/161,185, filed Jan. 28, 2021, 4 pages.

Corrected Notice of Allowability mailed on Dec. 12, 2024, for U.S. Appl. No. 16/008,976, filed Jun. 14, 2018, 2 pages.

Dominguez (2007). "Colecistectomia con un trocar asistida por imanes de neodimio. Reporte de un caso." *Asociacion Mexicana de Cirugia Endo*. vol. 8. No. 4, pp. 172-176 (with English Abstract).

Dominguez, G. et al. (2009). "Retraction and triangulation with neodymium magnetic forceps for single-port laparoscopic cholecystectomy," Surg. Endosc. 23:1660-1666.

Duchene, D.A. et al. (2004). "Magnetic positioning system for trocarless laparoscopic instruments," J. of Endourology 18:693.

Extended European Search Report mailed on Jul. 20, 2016, for EP Application No. 14 778 895.4, filed on Feb. 25, 2014, 7 pages.

Extended European Search Report mailed on Dec. 20, 2016, for EP Application No. 09 839 564.3, filed on Oct. 1, 2009, 11 pages.

Extended European Search Report mailed on Sep. 27, 2017, for EP Application No. 15 741 055.6, filed on Jan. 21, 2015, 9 pages.

Extended European Search Report mailed on Oct. 30, 2018, for EP Application No. 16 780 691.8, filed on Apr. 13, 2016, 6 pages.

Extended European Search Report mailed on Nov. 26, 2018, for EP Application No. 16 780 688.4, filed on Sep. 26, 2017, 9 pages.

Extended European Search Report mailed on Jul. 22, 2019, for EP Application No. 19 151 941.2, filed on Feb. 25, 2014, 6 pages.

Extended European Search Report mailed on Aug. 22, 2019, for EP Application No. 17 736 483.3, filed on Jan. 6, 2017, 8 pages.

Extended European Search Report mailed on May 31, 2013, for EP Application No. 08 853 840.0, filed on Nov. 26, 2008, 11 pages.

Extended European Search Report mailed on Jan. 4, 2022, for EP Application No. 21 189 505.7, filed on Apr. 13, 2016, 10 pages.

Extended European Search Report mailed on Jan. 18, 2022, for EP Application No. 21 187 437.5, filed on Apr. 13, 2016, 6 pages.

Extended European Search Report mailed on Feb. 17, 2022, for EP Application No. 21 189 492.8, filed on Feb. 25, 2014, 6 pages.

Extended European Search Report mailed on Feb. 21, 2025, for EP Application No. 24 208 902.7, filed on Apr. 13, 2016, 9 pages.

Fernandez, R. et al. (2012). "Determining a Performance Envelope for Capture of Kidney Stones Functionalized with Superparamagnetic Particles," Journal of Endourology, 26(9):1227-1230.

Fernandez, R. et al. (2003). "Development of a Transabdominal Anchoring System for Trocar-Less Laparoscopic Surgery," Advances in Bioengineering—ASME International Mechanical Engineering Congress & Exposition, Washington DC, Nov. 2003, Bed vol. 55, pp. 157-158.

Final Office Action mailed on Sep. 16, 2016, for U.S. Appl. No. 14/704,828, filed May 5, 2015, 10 pages.

Final Office Action mailed on Jan. 25, 2016, for U.S. Appl. No. 14/337,082, filed Jul. 21, 2014, 9 pages.

Final Office Action mailed on Dec. 28, 2016, for U.S. Appl. No. 14/200,302, filed Mar. 7, 2014, 15 pages.

Final Office Action mailed on Sep. 6, 2017, for U.S. Appl. No. 14/200,302, filed Mar. 7, 2014, 9 pages.

Final Office Action mailed on Mar. 7, 2018, for U.S. Appl. No. 15/098,262, filed Apr. 13, 2016, 10 pages.

Final Office Action mailed on Feb. 26, 2019, for U.S. Appl. No. 15/195,898, filed Jun. 28, 2016, 9 pages.

Final Office Action mailed on Nov. 25, 2020, for U.S. Appl. No. 15/728,297, filed Oct. 9, 2017, 11 pages.

Final Office Action mailed on Sep. 3, 2021, for U.S. Appl. No. 16/149,576, filed Oct. 2, 2018, 14 pages.

Final Office Action mailed on Oct. 26, 2021, for U.S. Appl. No. 16/419,363, filed May 22, 2019, 7 pages.

Final Office Action mailed on Oct. 28, 2021, for U.S. Appl. No. 16/528,878, filed Aug. 1, 2019, 8 pages.

Final Office Action mailed on Feb. 7, 2022, for U.S. Appl. No. 16/008,976, filed Jun. 14, 2018, 20 pages.

Final Office Action mailed on May 2, 2022, for U.S. Appl. No. 15/728,297, filed Oct. 9, 2017, 13 pages.

Final Office Action mailed on Mar. 16, 2023, for U.S. Appl. No. 16/008,976, filed Jun. 14, 2018, 21 pages.

Final Office Action mailed on May 31, 2024, for U.S. Appl. No. 16/008,976, filed Jun. 14, 2018, 12 pages.

International Search Report mailed on Jul. 30, 2014, for PCT Application No. PCT/US2014/021537, filed on Mar. 7, 2014, 2 pages.

International Search Report for International Application No. PCT/IB2009/054307 dated Feb. 8, 2010, 4 pages.

International Search Report mailed on May 4, 2015, for PCT Application No. PCT/US2015/012319, filed on Jan. 21, 2015, 2 pages.

International Search Report mailed on Jul. 18, 2014, for PCT Application No. PCT/US2014/018307, filed on Feb. 25, 2014, 4 pages.

(56) References Cited

OTHER PUBLICATIONS

International Search Report mailed on Jul. 15, 2016, for PCT Application No. PCT/US2016/027385, filed on Apr. 13, 2016, 2 pages.
International Search Report mailed on Aug. 22, 2016, for PCT Application No. PCT/US2016/027390, filed on Apr. 13, 2016, 4 pages.
International Search Report mailed on Apr. 3, 2017, for PCT Application No. PCT/US2017/012628, filed on Jan. 6, 2017, 2 pages.
International Search Report mailed on Apr. 9, 2009, for PCT Application No. PCT/US2008/084991, filed on Nov. 26, 2008, 3 pages.
Leong, F. et al. (2016). "Magnetic surgical instruments for robotic abdominal surgery," IEEE Reviews in Biomedical Engineering 9:66-78.
Mashaud, L. et al. (2011). "Tissue Compression Analysis for Magnetically Anchored Cautery Dissector During Single Site Laparoscopic Cholecystectomy," Journal of Gastrointestinal Surgery 15:902-907.
Mashaud, L. et al. (2010). "Tissue Compression Analysis for Magnetically Anchored Cautery Dissector During Single Site Laparoscopic Cholecystectomy," Gastroenterology, 138:5 (Supplement 1):S-882.
Mashaud, L. et al. (2010). "Magnetic Cautery Dissector Suitability for Traditional or Single Site Laparoscopic Cholecystectomy in Human Cadaver Models," 12th World Congress of Endoscopic Surgery, P246, National Harbor, MD, Apr. 2010.
Milki, A.A. et al. (1998). "Vaginal ultrasound probe coverage leakage: implications for patient care, fertility and sterility, American Society for Reproductive Medicine," Fertil. Steril. 69:409-411.
Non-Final Office Action mailed on May 25, 2016, for U.S. Appl. No. 14/200,302, filed Mar. 7, 2014, 12 pages.
Non-Final Office Action mailed on May 21, 2013, for U.S. Appl. No. 13/132,185, filed Aug. 17, 2011, 18 pages.
Non-Final Office Action mailed on Jul. 21, 2016, for U.S. Appl. No. 14/337,082, filed Jul. 21, 2014, 9 pages.
Non-Final Office Action mailed on Jul. 13, 2015, for U.S. Appl. No. 14/337,082, filed Jul. 21, 2014, 10 pages.
Non-Final Office Action mailed on Jan. 25, 2016, for U.S. Appl. No. 14/704,828, filed May 5, 2015, 9 pages.
Non-Final Office Action mailed on Jul. 14, 2015, for U.S. Appl. No. 14/704,828, filed May 5, 2015, 10 pages.
Non-Final Office Action mailed on Oct. 24, 2013, for U.S. Appl. No. 14/019,370, filed Sep. 5, 2013, 7 pages.
Non-Final Office Action mailed on Oct. 22, 2015, for U.S. Appl. No. 14/019,404, filed Sep. 5, 2013, 6 pages.
Non-Final Office Action mailed on May 22, 2017, for U.S. Appl. No. 14/200,302, filed Mar. 7, 2014, 14 pages.
Non-Final Office Action mailed on May 3, 2017, for U.S. Appl. No. 14/704,828, filed May 5, 2015, 8 pages.
Non-Final Office Action mailed on Jul. 24, 2017, for U.S. Appl. No. 15/098,262, filed Apr. 13, 2016, 9 pages.
Non-Final Office Action mailed on Jun. 29, 2018, for U.S. Appl. No. 15/195,898, filed Jun. 28, 2016, 9 pages.
Non-Final Office Action mailed on Sep. 17, 2019, for U.S. Appl. No. 15/728,297, filed Oct. 9, 2017, 8 pages.
Non-Final Office Action mailed on Mar. 3, 2020, for U.S. Appl. No. 15/728,302, filed Oct. 9, 2017, 14 pages.
Non-Final Office Action mailed on Mar. 6, 2020, for U.S. Appl. No. 15/926,578, filed Mar. 20, 2018, 9 pages.
Non-Final Office Action mailed on Dec. 22, 2020, for U.S. Appl. No. 16/149,576, filed Oct. 2, 2018, 10 pages.
Non-Final Office Action mailed on May 12, 2021, for U.S. Appl. No. 16/008,976, filed Jun. 14, 2018, 15 pages.
Non-Final Office Action mailed on Apr. 29, 2021, for U.S. Appl. No. 16/419,363, filed May 22, 2019, 9 pages.
Non-Final Office Action mailed on Apr. 15, 2021, for U.S. Appl. No. 16/528,878, filed Aug. 1, 2019, 6 pages.
Non-Final Office Action mailed on Sep. 15, 2021, for U.S. Appl. No. 15/728,297, filed Oct. 9, 2017, 11 pages.
Non-Final Office Action mailed on Aug. 5, 2022, for U.S. Appl. No. 16/008,976, filed Jun. 14, 2018, 18 pages.
Non-Final Office Action mailed on Oct. 12, 2022, for U.S. Appl. No. 16/746,448, filed Jan. 17, 2020, 16 pages.
Non-Final Office Action mailed on Oct. 28, 2022, for U.S. Appl. No. 17/161,185, filed Jan. 28, 2021, 9 pages.
Non-Final Office Action mailed on Oct. 16, 2023, for U.S. Appl. No. 16/008,976, filed Jun. 14, 2018, 23 pages.
Non-Final Office Action mailed on Feb. 16, 2024, for U.S. Appl. No. 17/332,876, filed May 27, 2021, 10 pages.
Non-Final Office Action mailed on Jul. 18, 2024, for U.S. Appl. No. 17/836,867, filed Jun. 9, 2022, 10 pages.
Non-Final Office Action mailed on Sep. 13, 2024, for U.S. Appl. No. 18/220,192, filed Jul. 10, 2023, 11 pages.
Notice of Allowance mailed on Feb. 14, 2014, for U.S. Appl. No. 14/019,370, filed Sep. 5, 2013, 7 pages.
Notice of Allowance mailed on Mar. 14, 2014, for U.S. Appl. No. 13/132,185, filed Aug. 17, 2011, 7 pages.
Notice of Allowance mailed on Mar. 14, 2016, for U.S. Appl. No. 14/019,404, filed Sep. 5, 2013, 7 pages.
Notice of Allowance mailed on May 3, 2017, for U.S. Appl. No. 14/337,082, filed Jul. 21, 2014, 7 pages.
Notice of Allowance mailed on Aug. 25, 2017, for U.S. Appl. No. 14/337,082, filed Jul. 21, 2014, 7 pages.
Notice of Allowance mailed on Nov. 22, 2017, for U.S. Appl. No. 14/200,302, filed Mar. 7, 2014, 5 pages.
Notice of Allowance mailed on Jan. 19, 2018, for U.S. Appl. No. 14/704,828, filed May 5, 2015, 7 pages.
Notice of Allowance mailed on Aug. 24, 2018, for U.S. Appl. No. 15/098,262, filed Apr. 13, 2016, 9 pages.
Notice of Allowance mailed on Sep. 11, 2019, for U.S. Appl. No. 15/195,898, filed Jun. 28, 2016, 9 pages.
Notice of Allowance mailed on Nov. 26, 2019, for U.S. Appl. No. 15/195,898, filed Jun. 28, 2016, 6 pages.
Notice of Allowance mailed on Sep. 29, 2020, for U.S. Appl. No. 15/728,302, filed Oct. 9, 2017, 8 pages.
Notice of Allowance mailed on Feb. 5, 2021, for U.S. Appl. No. 15/926,578, filed Mar. 20, 2018, 9 pages.
Notice of Allowance mailed on Feb. 14, 2022, for U.S. Appl. No. 16/149,576, filed Oct. 2, 2018, 9 pages.
Notice of Allowance mailed on Apr. 7, 2022, for U.S. Appl. No. 16/528,878, filed Aug. 1, 2019, 6 pages.
Notice of Allowance mailed on Apr. 20, 2022, for U.S. Appl. No. 16/419,363, filed May 22, 2019, 6 pages.
Notice of Allowance mailed on Oct. 19, 2022, for U.S. Appl. No. 15/728,297, filed Oct. 9, 2017, 8 pages.
Notice of Allowance mailed on Apr. 3, 2023, for U.S. Appl. No. 16/746,448, filed Jan. 17, 2020, 12 pages.
Notice of Allowance mailed on Apr. 10, 2023, for U.S. Appl. No. 17/161,185, filed Jan. 28, 2021, 9 pages.
Notice of Allowance mailed on Aug. 14, 2024, for U.S. Appl. No. 18/346,089, filed Jun. 30, 2023, 14 pages.
Notice of Allowance mailed on Sep. 5, 2024, for U.S. Appl. No. 17/332,876, filed May 27, 2021, 7 pages.
Notice of Allowance mailed on Nov. 29, 2024, for U.S. Appl. No. 16/008,976, filed Jun. 14, 2018, 8 pages.
Notice of Allowance mailed on Feb. 26, 2025, for U.S. Appl. No. 17/836,867, filed Jun. 9, 2022, 8 pages.
Notice of Allowance mailed on Mar. 26, 2025, for U.S. Appl. No. 18/220,192, filed Jul. 10, 2023, 9 pages.
Odwin, C.S. et al. (1990). "Prove covers and disinfectants for transvaginal transducers," JDMS 6:130-135.
Park, S. et al. (2007). "Trocar-less instrumentation for laparoscopy magnetic positioning of intra-abdominal camera and retractor," Surgical Technique 245:379-384.
Raman, J. (2009). "Complete Transvaginal Notes Nephrectomy Using Magnetically Anchored Instrumentation," Journal of Endourology 23:367-371.
Rivas, H. et al. (2005). "A Magnetic Positioning System to Drive Trocarless Laparoscopic Instruments," First International Mini-

(56) References Cited

OTHER PUBLICATIONS mally Invasive Robotic Association (MIRA) Conference on Robotic Surgery, Innsbruck, Austria, Dec. 2005.
Scott, D.J. et al. (2007). "Completely transvaginal Notes cholecystectomy using magnetically anchored instruments," Surg. Endosc. 21:2308-2316.
Scott, D. et al. (2008). "Optimizing Magnetically Anchored Camera, Light Source, Graspers, and Cautery Dissector for Transvaginal Notes Cholecystectomy," Surgical Endoscopy 22:S244.
Scott, D. et al. (2008). "Randomized Comparison of Laparoscopic, Flexible Endoscopic, and Wired and Wireless Magnetic Notes Cameras on Ex-Vivo and In-Vivo Surgical Performance," Gastrointestinal Endoscopy, vol. 67: AB115.
Scott, D. et al. (2008). "Transvaginal Single Access "Pure" Notes Sleeve Gastrectomy Using a Deployable Magnetically Anchored Video Camera," Gastrointestinal Endoscopy, vol. 67: AB116.
Scott, D. et al. (2007). "Transgastric, Transcolonic, and Transvaginal Cholecystectomy Using Magnetically Anchored Instruments," Surgical Endoscopy, vol. 21: S474.
Scott, D. et al. (2007). "Completely Transvaginal Cholecystectomy Using Magnetically Anchored Instruments," Surgical Endoscopy, vol. 21: S335.
Scott, D. et al. (2007). "Short-Term Survival Outcomes Following Transvaginal Notes Cholecystectomy Using Magnetically Anchored Instruments," Gastrointestinal Endoscopy, vol. 65: AB109.
Supplemental Notice of Allowability mailed on Dec. 18, 2020, for U.S. Appl. No. 15/728,302, filed Oct. 9, 2017, 3 pages.
Swain, C. et al. (2008). "Linear Stapler Formation of Ileo-Rectal, Entero-Enteral and Gastrojejunal Anastomoses During Dual and Single Access "Pure" Notes Procedures: Methods, Magnets and Stapler Modifications," Gastrointestinal Endoscopy, vol. 67: AB119.
Swain, P. et al. (2008). "Wireless Endosurgery for Notes," Gastrointestinal Endoscopy, vol. 67: AB104.
Tan, Y. (2011). "Modeling of Magnetic Tools for Use with Superparamagnetic Particles for Magnetic Stone Extraction," 26th Engineering & Urology Society Annual Meeting, p. 29, Washington DC, May 14, 2011.
Tan, Y. (2012). "In Vitro Comparison of Prototype Magnetic Tool with Conventional Nitinol Basket for Ureteroscopic Retrieval of Stone Fragments Rendered Paramagnetic with Iron-Oxide Microparticles," The Journal of Urology, vol. 187, Issue 4, pp. e857-858.
Tang, S. (2008). "Live Video Manipulator for Endoscopy and Notes," Gastrointestinal Endoscopy 68:559-564.
Tillander, H. (1951). "Magnetic guidance of a catheter with articulated steel tip," Acta Radiologica pp. 62-64.
Wikipedia (2015). "Stainless Steel," retrieved from https://en.wikipedia.org/wiki/Stainless_steel, 13 pages.
Written Opinion of the International Searching Authority mailed on Jul. 30, 2014, for PCT Application No. PCT/US2014/021537, filed on Mar. 7, 2014, 5 pages.
Written Opinion of the International Searching Authority for International Application No. PCT/IB2009/054307 dated Feb. 8, 2010, 6 pages.
Written Opinion of the International Searching Authority mailed on Jul. 18, 2014, for PCT Application No. PCT/US2014/018307, filed on Feb. 25, 2014, 5 pages.
Written Opinion of the International Searching Authority mailed on May 4, 2015, for PCT Application No. PCT/US2015/012319, filed on Jan. 21, 2015, 5 pages.
Written Opinion of the International Searching Authority mailed on Jul. 15, 2016, for PCT Application No. PCT/US2016/027385, filed on Apr. 13, 2016, 11 pages.
Written Opinion of the International Searching Authority mailed on Aug. 22, 2016, for PCT Application No. PCT/US2016/027390, filed on Apr. 13, 2016, 9 pages.
Written Opinion of the International Searching Authority mailed on Apr. 3, 2017, for PCT Application No. PCT/US2017/012628, filed on Jan. 6, 2017, 7 pages.
Written Opinion of the International Searching Authority mailed on Apr. 9, 2009, for PCT Application No. PCT/US2008/084991, filed on Nov. 26, 2008, 12 pages.
Zeltser, I.S. et al. (2007). "Single trocar laparoscopic nephrectomy using magnetic anchoring and guidance system in the porcine model," J. of Urology 178:1-4.
U.S. Appl. No. 61/113,495, filed Nov. 11, 2008, by Fernandez et al. (Copy not attached).

* cited by examiner

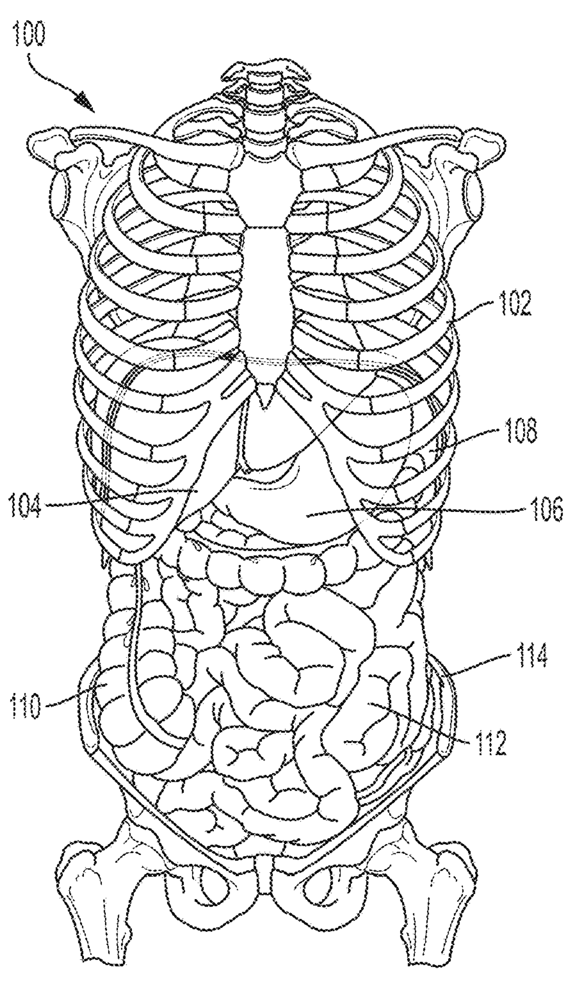
FIG. 1A
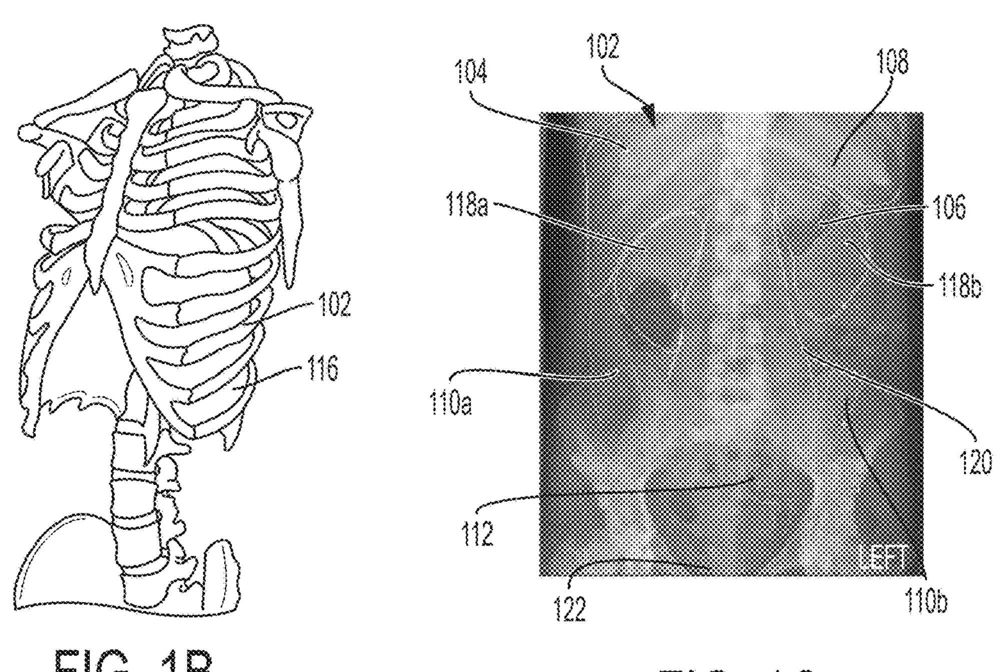
FIG. 1B
FIG. 1C 824
808
824
821
828
814
830
816
806
820
818
822
800
912
910
920
922
902
914
918
916
906
908
904
900
922

800
900
806
814
808
822
824
826
914
918
916
920
902
816
820
818
821
816
828
830
912
910
906
908
904

800
824
918
916
900
914
826
920
808
822
902
806
820
818
821
816
828
910
814
830
906
908
904

800
902
824
914
918
826
916
900
808
830
822
806
820
818
821
816
910
912
828
814
906
908
904
920

1000
1004
900
920
902
906
904
1002

1006
902
1008
904
900
906
920
1008

1100
1102
1190
1192
1194
1104
1108
1162
1150
1164
1120
1110
1106

1102
1104
1182
1108
1120
1164
1180
1160
1166
1106
1100
1184
1140
1110
1144
1142
1146

1190
1194
1192
1102
1104
1100
1108
1168
1166
1122
1160
1162
1120
1184
1156
1154
1112
1106
1110
1150
1152

1106
1102
1222
1152
1150
1154
1214
1220
1206
1208
1218
1110
1112
1102
1160
1104
1120

DIRECTABLE TRACTION SYSTEMS AND METHODS

CROSS-REFERENCE TO RELATED APPLICATIONS

This application is a continuation of U.S. patent application Ser. No. 17/332,876, filed May 27, 2021, which is a continuation of U.S. patent application Ser. No. 15/926,578, filed Mar. 20, 2018, now U.S. Pat. No. 11,020,137, which claims priority to U.S. Provisional Patent Application No. 62/473,841, filed Mar. 20, 2017, the content of each of which is hereby incorporated by reference in its entirety.

FIELD

Devices, systems, and methods herein relate to minimally invasive procedures that may be used in diagnostic and/or therapeutic applications, including but not limited to manipulation and/or traction of tissue such as the liver.

BACKGROUND

Minimally invasive procedures such as endoscopic, laparoscopic, and thoracoscopic procedures may be associated with benefits such as lower pain, quicker post-surgical recovery, shortened hospitalization, and reduced complications when compared to open surgical procedures. During minimally invasive procedures it may be desirable to reposition or otherwise manipulate tissue. However, the placement of an incision is limited due to patient anatomy, which may in turn limit the range of motion and/or direction of force that may be applied during a procedure to manipulate tissue. Accordingly, it may be desirable to provide one or more methods to rotate, retract, pull, reposition, and otherwise manipulate tissue with additional range of motion and/or degrees of freedom independent of an access site into the body.

BRIEF SUMMARY

Described herein are methods, systems, and devices for providing remote traction of tissue such as for minimally invasive surgical procedures. The methods described herein may increase the number of directions and locations available for tissue traction in an abdominal cavity. This may provide access to other tissue in the abdominal cavity, which may allow additional procedures to be performed. Generally, the methods for performing a surgical procedure may comprise introducing a grasper through an opening into an abdominal cavity, grasping a portion of a left lobe of a liver with the grasper, rotating the grasper towards a control element located outside the abdominal cavity by applying a magnetic field to the grasper across a body wall (e.g., abdominal wall, thoracic wall), and moving the control element over a set of ribs such that the liver bends into a folded configuration.

In some variations, a space may be accessed in an abdominal cavity vacated by the grasped portion of the liver. In some other variations, a stomach may be accessed in an abdominal cavity vacated by the grasped portion of the liver. In yet other variations, a stomach may be visualized in the abdominal cavity vacated by the portion of the liver using an optical sensor. In some variations, a gastric procedure may be performed while the liver forms the fold. In some variations, the control element may be stationary during the gastric procedure. In other variations, the control element may be repositioned over the set of ribs during the gastric procedure. In some of these variations, the gastric procedure may comprise one or more of a gastric bypass, a sleeve gastrectomy, a gastric band procedure, a biliopancreatic diversion with duodenal switch, and a gastric cancer resection.

In some variations, the methods may further comprise performing a biliopancreatic diversion with duodenal switch that includes the step of performing a sleeve gastrectomy, grasping a portion of a right lobe of a liver with the grasper, rotating the grasper grasping the right lobe towards the control element located outside the abdominal cavity by applying the magnetic field to the grasper across a body wall, moving the control element over the set of ribs such that the right lobe of the liver bends into a folded configuration, and cutting a pylorus from a duodenum.

In some variations, a superior portion of a patient may be tilted above an inferior portion of the patient. In some of these variations, a location of the control element may be maintained relative to the body wall while tilting the patient and visualizing tissue other than the liver. In other of these variations, the control element may be repositioned over the set of ribs while tilting the patient and visualizing tissue other than the liver.

In some variations, grasping the portion of the liver may comprise grasping a peripheral edge of the liver. In some other variations, moving the control element over the set of ribs may pull grasped tissue away from the opening. In other variations, moving the control element over the set of ribs may move the control element in a lateral direction. In yet other variations, moving the control element over the set of ribs may move the grasped portion of the liver anteriorly over a right lobe of the liver. In some variations, grasping the portion of the liver may comprise grasping a left-lateral portion of segment II of the liver. In some other variations, moving the control element may be performed in a left-superior direction over the set of ribs. In yet other variations, grasping the portion of the lobe may comprise grasping an inferior portion of segment III of the liver.

In some variations, introducing the detachable grasper may comprise introducing a delivery device assembled with the detachable grasper through the opening, reattaching the grasper to the delivery device, releasing the grasper from the grasped portion of the liver, and removing the delivery device from the opening.

In some variations, the set of ribs may comprise at least one of a fifth rib through a tenth rib. In some variation, an abdominal cavity may define the opening. In other variations, the opening may be defined in an abdominal cavity and may be inferior to the set of ribs. In some variations, moving the control element over the set of ribs may comprise applying the magnetic field to the grasper across the set of ribs, a diaphragm, and the thoracic wall. In some variations, the steps may further comprise moving the control element over the body wall and between a set of left ribs and a set of right ribs.

Also described here are methods of performing a surgical procedure comprising introducing a grasper through an opening into an abdominal cavity, grasping a portion of a right lobe of a liver with the grasper, rotating the grasper towards a control element located outside the abdominal cavity by applying a magnetic field to the grasper across a body wall, and moving the control element over a set of ribs such that the liver bends into a folded configuration. In some variations, a space may be accessed in an abdominal cavity vacated by the grasped portion of the liver. In some variations, grasping the portion of the liver comprises grasping an inferior portion of one or more of segments IV, V, and VI of the liver. In some variations, the method may further comprise performing a gastric procedure while the liver forms the fold. In some variations, a left lobe may be grasped with a first grasper and a right lobe may be grasped with a second grasper. In other variations, a plurality of graspers may grasp the liver and be spaced apart.

BRIEF DESCRIPTION OF THE DRAWINGS

FIG. 1A depicts an illustrative anatomy of a torso. FIG. 1B depicts a perspective view of an illustrative anatomy of a torso. FIG. 1C depicts an illustrative variation of an X-ray of a torso.

DETAILED DESCRIPTION

Figure 2A:
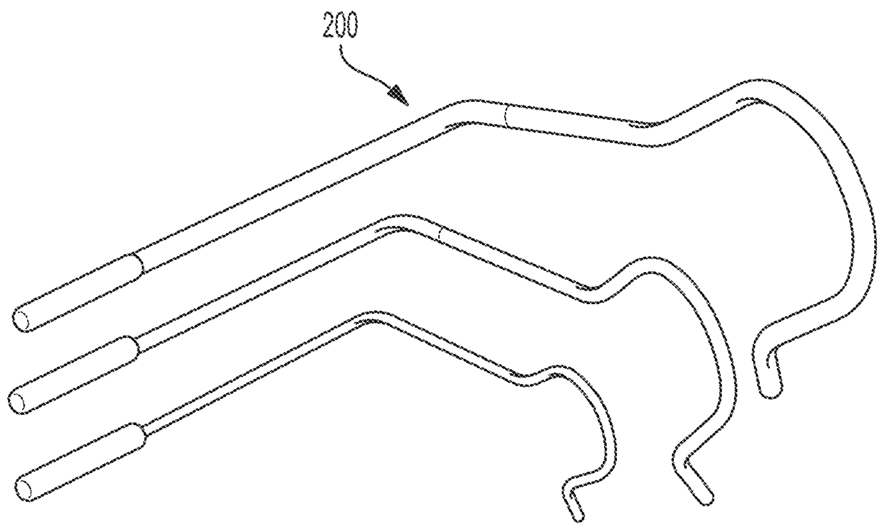
FIG. 2A depicts a perspective view of an illustrative variation of a set of Nathanson retractors.

Generally described here are methods, systems, and devices for performing a surgical procedure such as remote traction of tissue. The methods described here may comprise one or more of remote suspension, traction, mobilization, and manipulation of tissue within a body cavity during a minimally-invasive procedure. Access to the body cavity and internal organs may be achieved in a number of ways such as will be described in more detail below. Accordingly, it may be helpful to briefly describe the anatomy of one body cavity within which the methods described herein may be performed—the abdominal cavity. FIG. 1A is an illustrative depiction of the typical anatomy of a torso. Specifically, FIG. 1A shows a front view of a torso (100) including a set of ribs (102), liver (104), stomach (106), spleen (108), colon (110), small intestine (112), and pelvic bone (114). FIG. 1B is a perspective view of a diaphragm (116) relative to a set of ribs (102). FIG. 1C is an X-ray of a torso with annotated organs including the liver (104), stomach (106), spleen (108), colon (110*a*, 110*b*), small intestine (112), kidneys (118*a*, 118*b*), psoas muscle (120), and rectum (122).

Surgical access to internal tissues and/or organs to perform a procedure generally utilizes one or more entry ports, incisions, natural orifices, and other openings. In laparoscopic procedures, a port may be placed in the abdomen so as to minimize damage to tissue such as bones, muscles, the diaphragm, internal organs, retroperitoneal structures, and other tissues (e.g., nerves, lymphatic system). However, reducing trauma and damage (e.g., from penetration, breaking, tearing, cutting) to the patient also generally limits placement of an access site. In turn, surgical procedure steps including, but not limited to, cutting, cauterizing, stapling, moving, manipulating, and retracting tissue may be constrained by the location of the access site and the ability of an end effector to navigate through the abdominal cavity to reach desired tissue. For example, some devices may comprise a shaft configured to be advanced into an abdominal cavity through an access site with a distal end of the device comprising an end effector. In order to function, these devices require a direct physical connection path from an external control element (e.g., actuation mechanism) of the device to an end effector disposed within the patient. This may limit the location and direction in which the end effector interacts with tissue due to the constrained dimensions within an abdominal cavity.

Moreover, it should be appreciated that the anatomy of a patient is variable with respect to characteristics such as tissue location and size, the thickness and flexibility of the body walls, tissue elasticity, fragility, empty space, and the like, such that selection of an access site is patient dependent and selected by a surgeon. As used herein, a body wall may comprise one or more of an abdominal wall and a thoracic wall. The access site selected may be evaluated after the access site is formed and the surgeon is able to view the internal anatomy of the patient. Sub-optimal access site selection may lead to poor outcomes such as hematoma and pain if the surgeon performs the procedure (e.g., liver retraction) and attempts to overcome the sub-optimal access site. In some of these cases, the surgeon may need to create another access site (e.g., incision).

Figure 3:
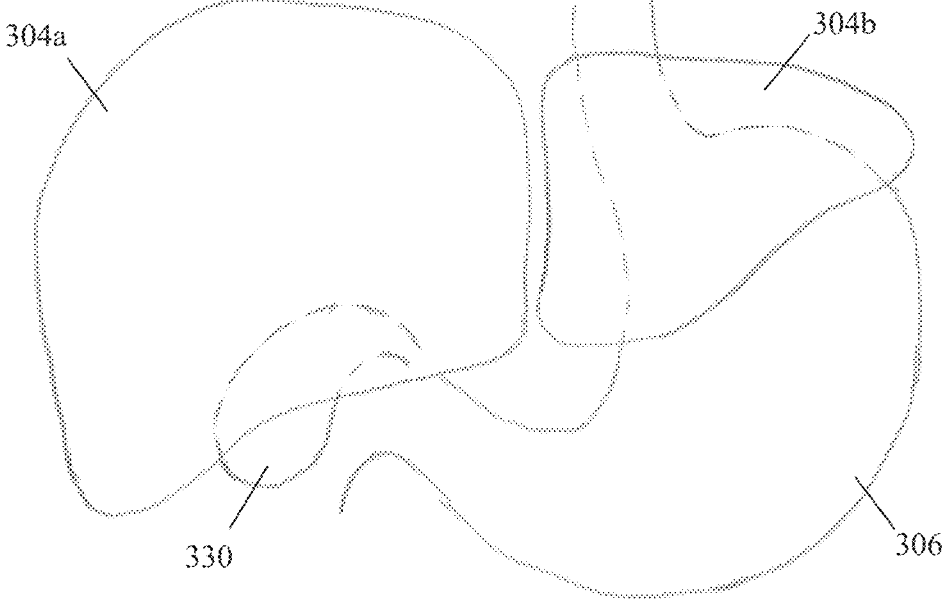
FIG. 3 depicts a schematic diagram of an illustrative variation of a set of abdominal organs.

In some cases, an organ may be moved (e.g., retracted) during a procedure in order to provide access to an otherwise obstructed organ. For example, as shown in FIG. 3, access to portions of the gallbladder (330) and stomach (306) may be blocked by one or more lobes of the liver (304*a*, 304*b*) as well as the ribs and diaphragm (not shown). Conventional tools, such as non-articulating graspers (e.g., straight-shafted graspers), articulating shafted graspers, and retractors that provide a lifting force (e.g., Nathanson retractors), may be used to provide tissue traction. However, these conventional tools have significant limitations.

Conventional non-articulating graspers may be advanced into a body cavity and be configured to releasably couple to a portion of tissue. However, manipulation of a conventional non-articulating end effector (e.g., straight-shafted grasper) is limited to axial rotation, axial advancement, axial retraction, and pivoting at the access site, thus constraining how the grasper may approach and interact with tissue. That is, an approach angle of the shafted end effector to tissue, the direction in which forces may be applied to tissue, and the maneuverability of the end effector may depend on the location of an access site relative to the tissue. Further, to move the grasped tissue, the straight-shafted grasper may apply a pushing force to the grasped tissue that may puncture and/or cause blunt trauma.

Figure 2B:
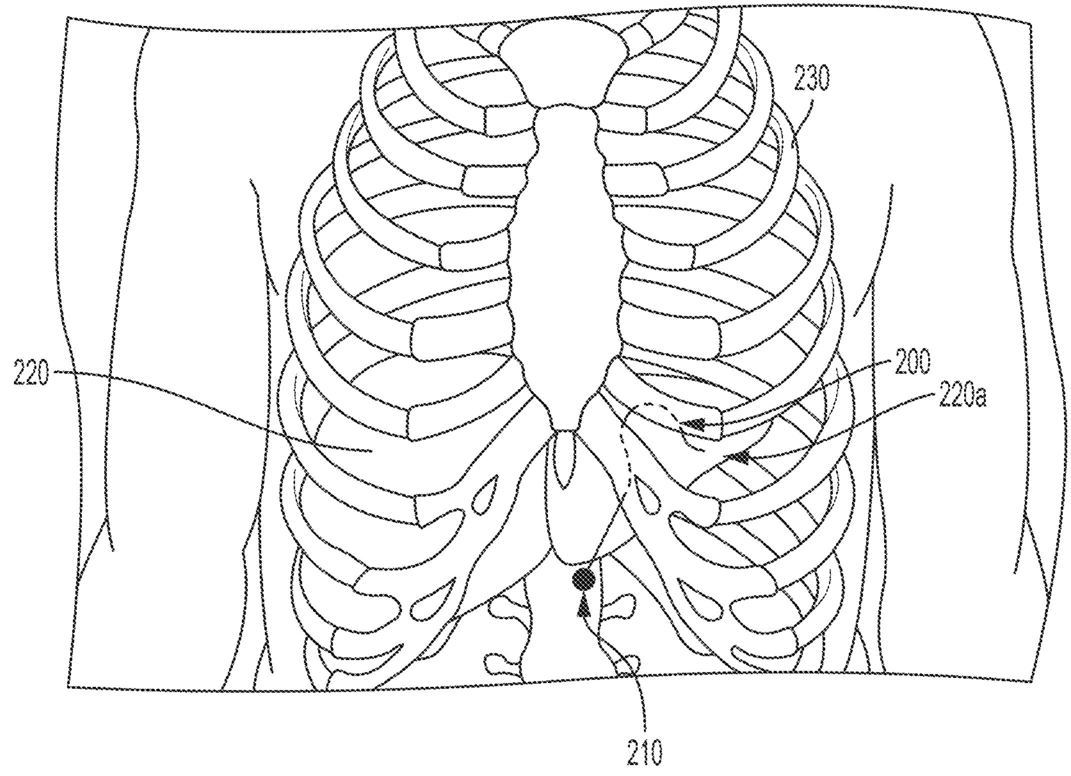
FIG. 2B depicts a schematic diagram of an illustrative variation of a surgical procedure utilizing a Nathanson retractor.

Retractors that provide a lifting force, such as Nathanson retractors, also have significant limitations. As an example, FIG. 2A is a perspective view of a set of Nathanson retractors (200) that may be used to retract the liver. FIG. 2B is an illustrative schematic diagram of a liver retraction procedure utilizing a Nathanson retractor (200) configured to lift a lobe (220*a*) of the liver (220) toward an abdominal wall. In FIG. 2B, an access site (210) such as an incision is created specifically for the Nathanson retractor in a portion of the abdominal wall inferior to the liver (220) and set of ribs (230). As shown in FIG. 2B, a Nathanson retractor (200) may be advanced through the access site (210), under the liver (220) and under the ribs (230) in a position to retract the liver.

Liver retraction using a Nathanson retractor (200) may benefit from simplicity but has a number of drawbacks. First, the liver's surface has very low friction, so a large portion of a lobe of the liver (220) must be retracted (i.e., lifted) by the Nathanson retractor (200) to retract the liver (220). Second, since the liver (220) is relatively dense, the small surface area of the Nathanson retractor (200) in contact with tissue may impart relatively large forces that may stress and damage the liver (220). Third, retracting sub-portions of the liver (220) may be difficult using Nathanson retractors (200) because the sub-portions may simply slip off the retractor (200) configured to retract large portions of the liver.

Conventional articulating end effectors (e.g., articulating shafted grasper, flexible shaft, articulating end effector) may be able to provide more maneuverability than non-articulating end effectors like straight-shafted graspers, but may be larger, complicated to operate, require more space within a body cavity, and still require a direct physical path from a distal end of the end effector through an access site. Like a non-articulating grasper, a conventional articulating shafted grasper may be advanced into a body cavity and be configured to releasably couple to a portion of tissue. However, the size of the end effector, its articulation mechanism, and location of the access site may limit the location and direction of force applied by the shafted grasper.

By contrast, the devices and systems as described in detail herein may be used without a direct physical path between an end effector within an abdominal cavity and an external control element, such that the end effector may be manipulated independent of an access site to aid tissue manipulation. As such, the methods and systems described herein may reduce stress and damage to tissue. For example, the methods and systems described herein may reduce stress and damage to the liver by manipulating specific portions of a liver independent of access site location.

Overview

Generally, the methods described herein may be used to apply force to tissue at a desired location and in a direction independent of an access site to provide access to tissue within an abdominal cavity. In some variations, a detachable end effector may be manipulated to generate forces at locations and in directions independent of an access site, thus allowing tissue to be grasped at previously inaccessible locations and manipulated in a wide range of directions. These methods may reduce the risk of damage to tissue, which may lead to better patient outcomes, such as by improving tissue visualization and allowing for less force to be applied to tissue.

The methods described here comprise releasably connecting an end effector, such as one of the graspers described here, to tissue, and providing a magnetic force to the grasper to move and/or hold the grasper and to provide traction of the tissue engaged by the grasper. In some variations, the grasper may be releasably connected to tissue inside of the body. To connect the grasper to the tissue, the grasper may be releasably coupled with a delivery device, wherein the delivery device may be configured to actuate the grasper. The delivery device may actuate the grasper to releasably connect the grasper to tissue, and may eject or otherwise decouple from the grasper after the grasper is connected to tissue.

When the grasper is decoupled from the delivery device, the grasper may be attracted by a magnetic force external to the body and may move or otherwise hold tissue without the need to have a shaft or other portion of a device positioned in a port or other access site. This may reduce the number of access sites required to provide remote suspension of tissue, which may allow for faster and more reliable surgical procedures. Furthermore, removing a shaft or other portion of a device between the access port and a grasper removes a potential obstacle from the abdominal cavity that may improve access and/or visualization of tissue. Unlike traditional tools such as a Nathanson retractor, the graspers described herein may also be configured to grasp a portion of a body organ that allow specific portions of the body organ to be moved to reduce the forces needed to manipulate the body organ, thereby reducing the risk of damage.

More particularly, a control element may be positioned externally of the body to affect (e.g., rotate, attract, repel) the grasper. A magnetic force provided by the control element may be configured to attract and/or repel the grasper to pull tissue in a desired direction of traction. The control element may be moved externally to the patient to move the grasper and grasped tissue in difficult-to-traverse areas of the body where an access site is impractical, such as near bones and the diaphragm.

The methods described herein may further comprise tilting a patient to provide access and/or visualization of tissue. In some variations, patient tilting and tissue traction may be performed together to provide access and/or visualization of tissue. For example, a patient platform having a patient lying flat thereon may be tilted such that the patient's head is above his/her feet in order for the stomach to shift inferiorly due to the force of gravity while a grasped portion of liver is held in place relative to a body wall. In some of these variations, additional procedures may be performed while the patient is tilted and tissue is retracted by the grasper and control element.

While illustrative examples of the graspers and delivery devices are described together below, it should be appreciated that the methods may involve actuating and delivering the graspers described herein using any suitable delivery device, and that that the delivery devices described here may be used to actuate and deliver any suitable grasper or grasping device. Moreover, it should be appreciated that while delivery devices are described herein primarily with reference to use with a grasper, the delivery devices described herein may also be used in the methods described herein to reversibly couple to another tool to deliver, position and reposition, and/or remove another tool. Similarly, while illustrative examples of graspers and control elements are described together below, it should be appreciated that in the methods described herein, the control elements may be used with any of the graspers and delivery devices described here. The methods may also comprise using devices or systems as described in U.S. application Ser. No. 14/019,370, filed Sep. 5, 2013, now issued as U.S. Pat. No. 8,764,769, in International Application Serial No. PCT/US2015/012319, filed Jan. 21, 2015, or in International Application Serial No. PCT/US2016/027390, filed Apr. 13, 2016, each of which is hereby incorporated by reference in its entirety.

I. Methods

The graspers and systems described herein may be used in minimally invasive procedures that may allow for greater ability to manipulate and/or retract tissues. These may include any suitable minimally invasive procedure, such as but not limited to abdominal procedures, gastric procedures, thorascopic procedures, bariatric procedures, and urological/gynecological procedures. Generally, as mentioned above, to provide tissue traction, suspension, and/or mobilization, a grasper as described herein may be advanced into the body, releasably connected to a tissue in the body, and manipulated using one or more control elements positioned externally to the body to move and hold the tissue. In some variations, the grasper may comprise a material that is attracted to a magnetic field. The control element may be a magnetic control element, and thus control of the grasper and the direction of traction may be independent of an access site (e.g., trocar, incision, natural orifice) in the body.

The methods described herein may provide a number of benefits including, for example, traction of one or more segments of a liver that may provide access to a stomach for a gastric procedure. In variations where a gastric procedure is performed, the liver may be suspended and/or repositioned as desired using the devices and systems described herein. For example, as described in more detail herein, the connection between the grasper and the tissue may be released, and the grasper may be repositioned and reconnected to tissue (either the same portion of tissue or different portion of tissue). The patient may be tilted to reposition a set of organs relative to the grasped tissue to further improve tissue access. When the methods are used to retract one or more segments of a liver, the forces applied to the liver may be lower than conventional methods so as to reduce tissue damage. Also, the grasper may be manipulated remotely without a physical path through an access site to an exterior of the abdominal cavity such as is necessary with a shafted grasper.

Figure 4:
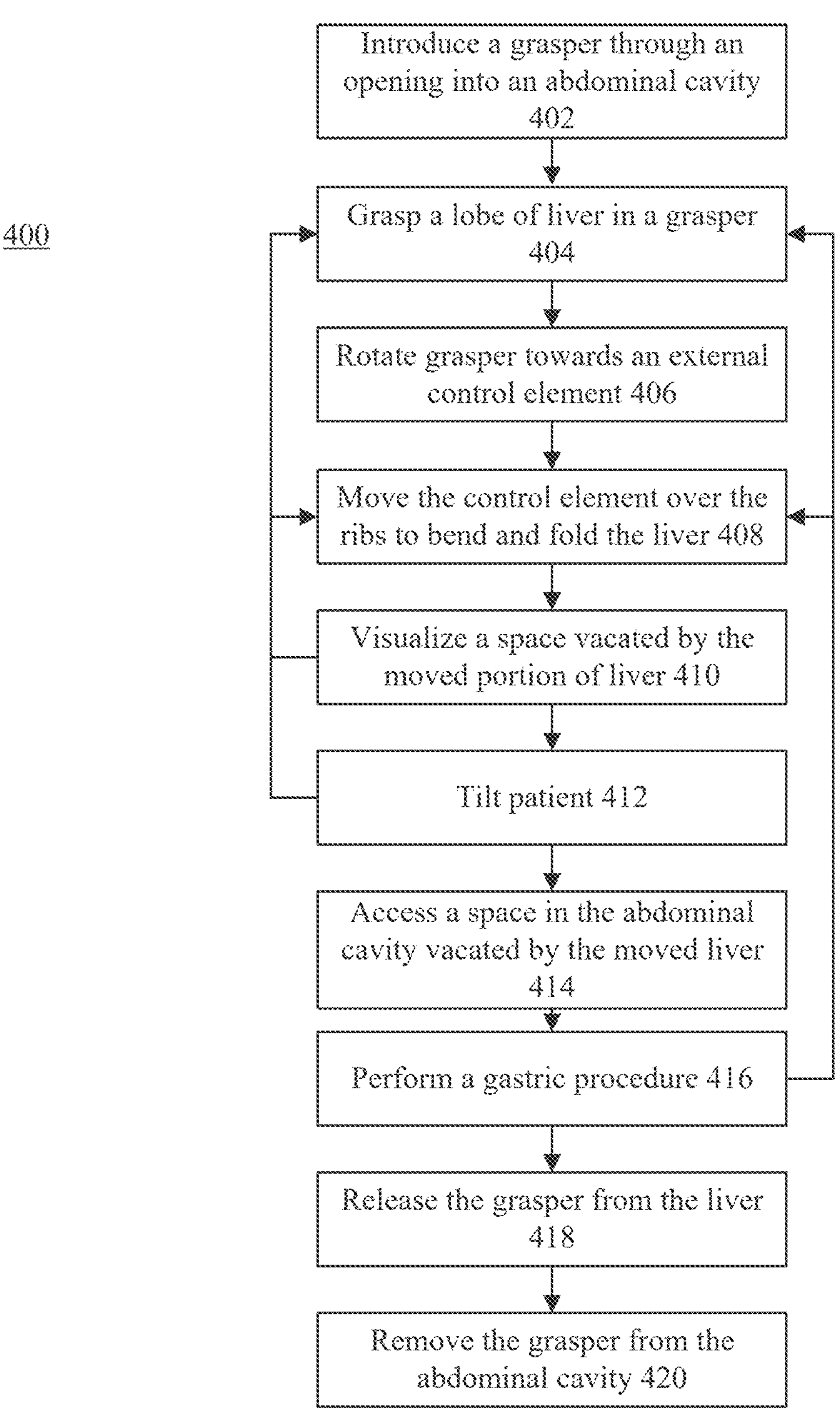
FIG. 4 depicts a flowchart representation of an illustrative variation of a surgical procedure.

FIG. 4 is a flowchart that generally describes an illustrative variation of a method (400) for performing a surgical procedure. Generally, this method for performing a surgical procedure may include introducing an end effector (e.g., grasper) through an opening into an abdominal cavity. The grasper may be advanced towards tissue such as a liver where a portion of a lobe of the liver may be grasped with the grasper. A control element may be placed near the body wall of the patient and used to apply a magnetic field to the grasper across the body wall. A delivery device, a separate instrument (e.g., shafted grasper), and/or the magnetic field may attract, rotate, and/or translate the grasper towards the control element to couple the grasper to the control element across the body wall and move the grasped portion of the liver in a desired direction. In some variations, the control element may be moved while visualizing the liver and/or other tissue to aid visualization of the underlying tissue. In some variations, additional procedures such as a gastric procedure may be performed after moving the control element. In some of these variations, retraction of the liver may be readjusted during the gastric procedure by grasping a different portion of the liver and moving the control element over the ribs of the patient. In some variations, the patient may be tilted in conjunction with tissue retraction. During any of the steps described herein, tissue within the abdominal cavity may be visualized. To complete the procedure, the grasper may release the liver and be removed from the abdominal cavity.

In some variations, the method (400) provides remote traction of tissue such as a liver that may provide access to another tissue (e.g., stomach) posterior to the retracted tissue. The method (400) may begin with introducing an end effector (e.g., grasper, clips, clamps, and the like) through an opening into an abdominal cavity (402). The grasper may be advanced into the body in any suitable manner. In some variations, an opening (e.g., access site, entry port) may be created by, for example, an incision, trocar, NOTES, and the like. In some variations, the opening may be formed inferior to the set of ribs in an area of the abdominal wall that does have not overly sensitive and/or difficult tissue (e.g., diaphragm, osseous tissue). In some variations, the opening may comprise a natural orifice (e.g., mouth, anus). In some variations, the grasper may be advanced into the body through a port as part of a minimally invasive procedure. In some instances, the minimally invasive procedure may be a reduced port technique or single-incision procedure. By contrast, conventional tools and methods operate within an opening throughout a tissue traction procedure, which may require the creation of one or more other openings for other devices (e.g., surgical instruments, visualization devices).

In some variations, the grasper may be advanced into the body using a delivery device, such as the delivery devices described in more detail herein (e.g., FIGS. 8A-8C, 9A-9F, 10A, 10D, 12A-12D). The grasper may be sterilized before use. In these variations, the grasper may be releasably coupled to a distal engagement portion of the delivery device, and the distal engagement portion of the delivery device may be advanced into the body to advance and position the grasper within the body. Once the delivery device and the grasper are advanced into the abdominal cavity, the delivery device may advance the grasper towards a portion of tissue (e.g., lobe of a liver). For example, the delivery device and attached grasper may be advanced toward the liver in a cephalic direction (e.g., toward the head) through an opening in an abdominal wall inferior to the set of ribs and/or the liver. Alternatively, a magnetic grasper may be introduced into the abdominal cavity through the opening without a delivery device. A secondary shafted grasper or other tool introduced into the abdominal cavity may be used to grasp the magnetic grasper and advance it towards a portion of tissue.

Once the grasper is positioned in the body, in step 404 of FIG. 4, the magnetic grasper may grasp a portion of tissue (e.g., by clamping a pair of jaws around the tissue). In some variations, the grasper may be placed in an open configuration using the delivery device carrying the grasper (e.g., by advancing an actuation rod through a barrel portion of the grasper) or by a grasping device which may engage and move the grasper to the open configuration (as described in more detail above). With the grasper in the open configuration, the grasper may be manipulated to position the tissue between a first jaw and a second jaw. The grasper may be returned to a closed configuration, in which the first jaw rotates toward the second jaw to hold the tissue between the jaws. For example, a surgeon may manipulate a trigger mechanism of a delivery device to actuate the jaws of a grasper from an open position to a closed position such that a desired portion of tissue may be held by the grasper. The grasper may then be released from the delivery device and/or grasping device, and these devices may be removed from the body. In variations where the grasper is advanced into the abdominal cavity using a delivery device and the delivery device is used to actuate the grasper, the grasper may be detached from the delivery device after grasping tissue.

Figure 12A:
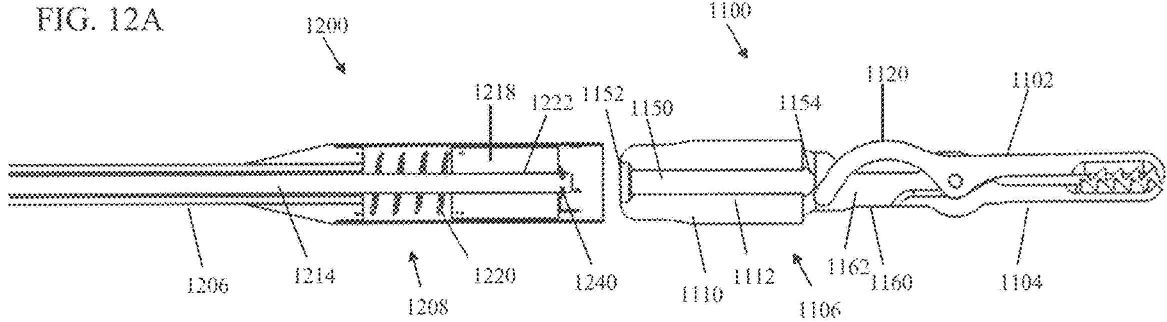
FIGS. 12A-12D depict cross-sectional side views of a distal portion of an illustrative variation of the delivery devices described here and the grasper of FIGS. 11A and 11B.
Figure 12B:
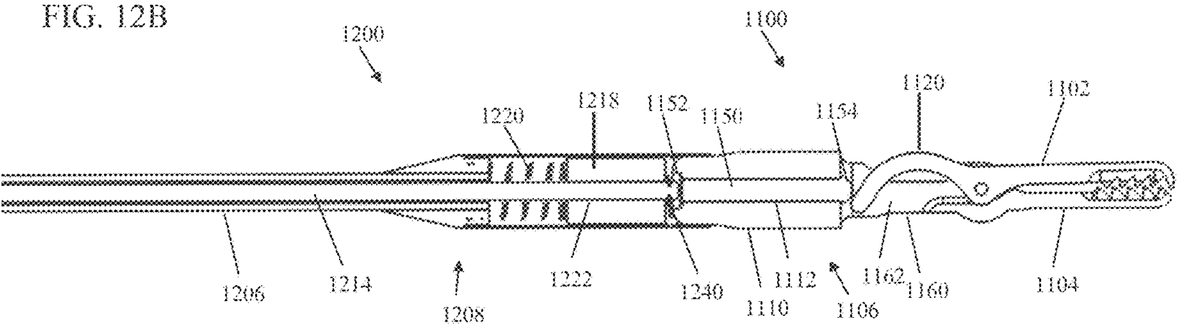

It should be appreciated that any suitable graspers, and/or delivery systems as described here may perform the steps discussed herein. For example, when the steps discussed are performed by the grasper shown in FIGS. 12A-12B, the grasper (900) may be advanced into the body toward a target tissue (1202), and positioned in an open configuration. To advance the grasper (900), the grasper (900) may be releasably coupled to a distal engagement portion (808) of a delivery device (800), and a user may advance the distal engagement portion (808) into the body to position the grasper (900). The tissue (1202) may be positioned between the first jaw (902) and second (904) jaw of the grasper (900), and the grasper (900) may be moved to a closed configuration to releasably couple the grasper (900) to the tissue (1202), as shown in FIG. 12B. Once connected to the tissue (1202), the grasper (900) may be released from the delivery device (800), and the delivery device (800) may be removed from the body. In some variations, the delivery device detached from the grasper may be completely retracted out of the opening to allow other devices (e.g., surgical instruments, visualization devices) to be advanced through and/or occupy the opening. For example, one or more visualization devices, secondary graspers, and other end effectors may be advanced into the abdominal cavity.

Figure 5:
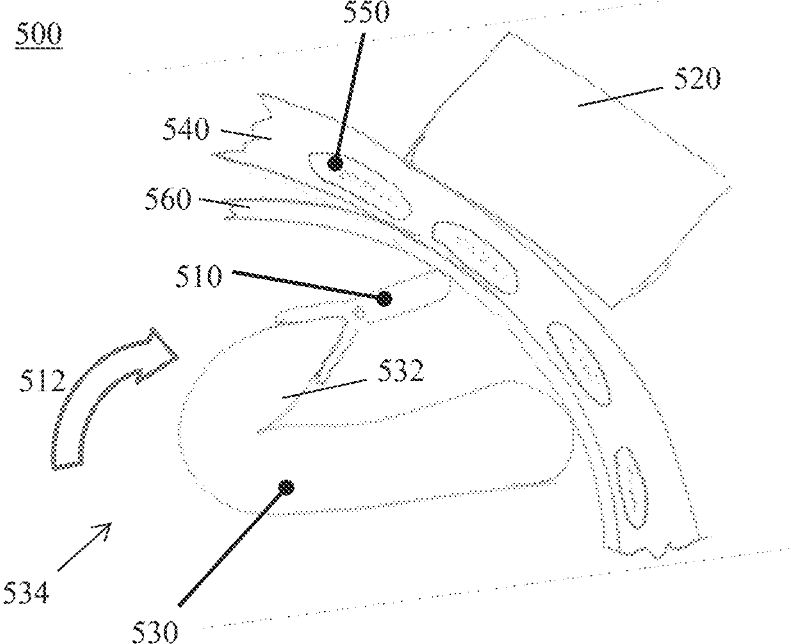
FIG. 5 depicts a cross-sectional view of an illustrative variation of a tissue traction procedure.
Figure 6:
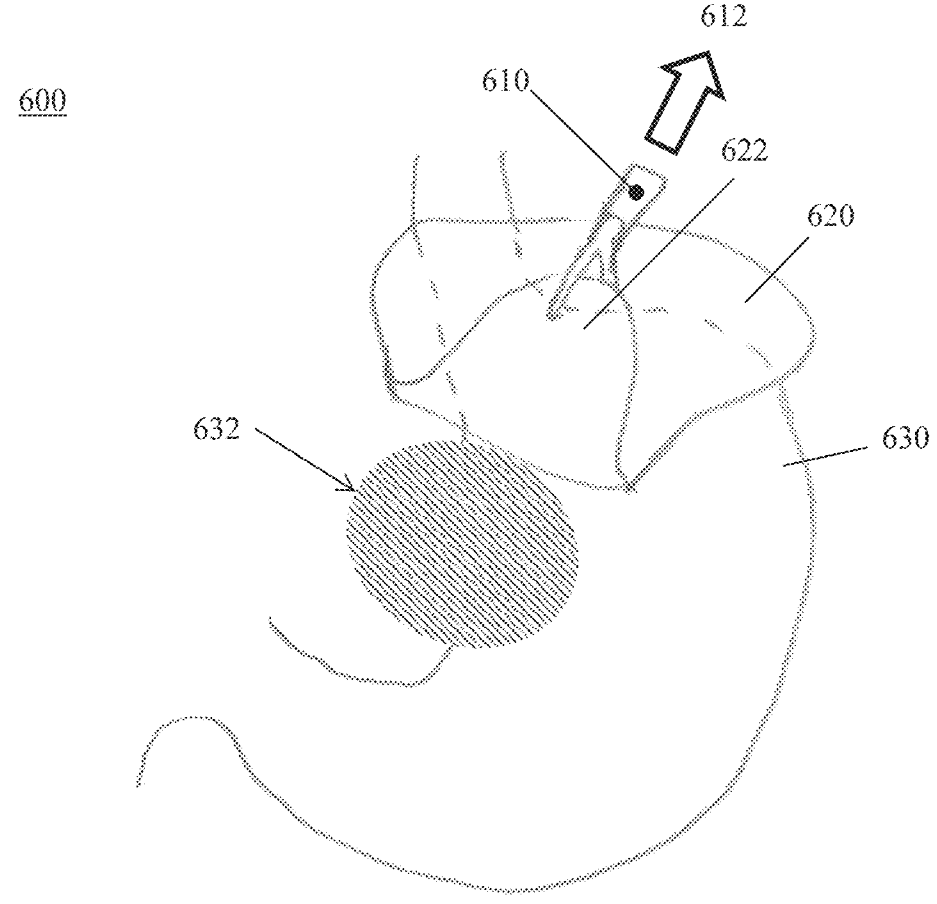
FIG. 6 depicts a schematic diagram of an illustrative variation of a tissue traction procedure.
Figure 7A:
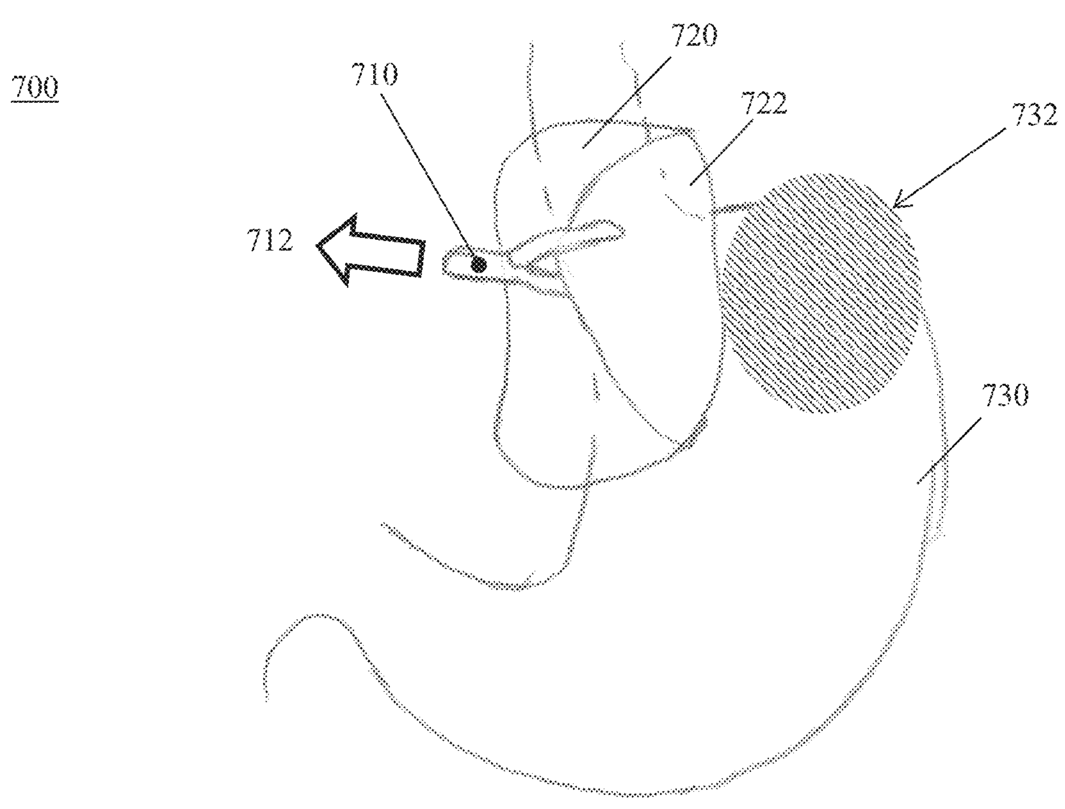
FIGS. 7A-7B depict a schematic diagram of an illustrative variation of a tissue traction procedure.
Figure 7B:
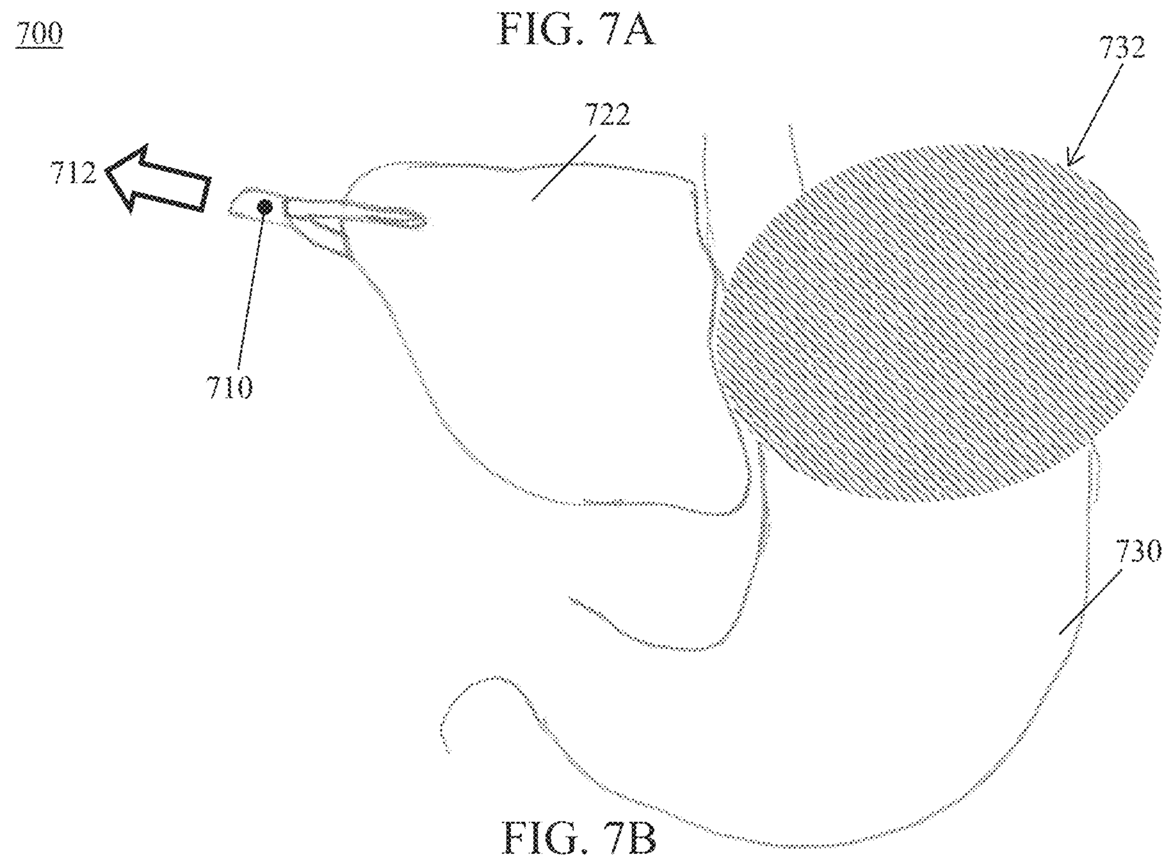

In some variations, the grasper may be used to grasp a portion of a lobe of a liver. A grasper grasping a portion of a lobe of a liver is shown in FIGS. 5, 6, and 7A-7B. The methods described herein may provide access to other organs without retracting the entire liver such that the forces applied to the liver may be reduced so as to reduce a risk of damage to the liver. In some variations, a peripheral edge (e.g., side edge, peritoneal edge) of a liver lobe may be grasped by the grasper. In some variations, a left-lateral portion of a segment II portion of the liver may be grasped, as shown in FIGS. 7A-7B. In some variations, an inferior portion of a segment III portion of the liver may be grasped, as shown in FIG. 6. Additionally or alternatively, a portion of a right lobe of a liver may be grasped. For example, an inferior portion of one or more of segments IVb, V, and VI of the liver may be grasped. A peripheral edge (e.g., side edge, peritoneal edge) of a right liver lobe may be grasped.

With the grasper releasably connected to the tissue, a control element comprising one or more magnetic elements, as described in more detail herein, may be positioned externally of the body and may apply a magnetic field of sufficient strength to attract and/or repulse the grasper to reposition and/or hold the grasper and grasped tissue. In step 406, the grasper may be rotated and/or translated towards a control element located outside the abdominal cavity by applying a magnetic field to the grasper across a body wall. That is, the grasper may be magnetically coupled to the control element such that the grasper is attracted to and rotated and/or translated towards the control element as shown in FIG. 5. Rotation of the grasper may generally include pitch rotation but may also include yaw rotation and roll rotation. As the grasper rotates, at least the portion of tissue grasped in the jaws of the grasper may rotate with the grasper. In some variations, the control element may be located on or near the body wall of the patient and generally anterior to the grasper. The magnetic field applied from the control element to the grasper may pass through tissue, such as the ribs, diaphragm, and thoracic wall, or abdominal wall of the patient. Additionally or alternatively, the grasper may be moved (e.g., raised) toward the body wall by a secondary shafted grasper or other tool, and then coupled to the control element.

For example, as shown in the cross-sectional side view of the patient (500) in FIG. 5, a grasper (510) may be coupled to a portion (532) of a liver (530) including, but not limited to, sections II, III, IV, V, and VI of the liver, as described in more detail herein. A control element (520) may be generally disposed anterior to the grasper (510) and liver (530) where a thoracic wall (540), set of ribs (550), and diaphragm (560) are between the grasper (510) and the control element (520). When a magnetic field is applied to the grasper (510) from the control element (520), the grasper (510) and the grasped portion of liver (532) may rotate and/or translate such that the grasper (510) is attracted towards the control element (520). Specifically, a proximal end of the grasper (510) may be attracted towards the control element (520). A magnetic field applied across the thoracic wall (540), ribs (550), and diaphragm (560) may pitch the grasper (510) and grasped portion of liver (530) towards the control element (520) such that the liver (530) bends into a folded configuration. That is, the grasped portion of tissue (532) may fold anteriorly over another portion of the liver (530) where, for example, the grasped portion (532) may be pulled. In some variations, the control element (520) may be spaced apart from a surface of the thoracic wall (540). In some variations, the control element may be translated toward the body wall of the patient, such as when large deposits of adipose tissue lie between the grasper and control element, and in other variations, the control element may not be translated. In some variations, the magnetic field applied by the control element (520) may rotate the grasped portion of tissue (532) to be substantially perpendicular to another portion of the liver (530). In some other variations, the magnetic field applied by the control element (520) may rotate the grasped portion of tissue (532) to form an acute angle relative another portion of the liver (530). Specifically, a grasped portion of tissue (532) may be pulled over the liver (530) to create a bend such that the liver folds over itself. This may allow tissue underneath the liver (530) to be better visualized. By contrast, conventional devices such as a Nathanson retractor lift up large portions of the liver towards the abdominal wall but do not allow smaller portions of the liver to be bent or folded over itself.

Some methods may include using a plurality of graspers to retract the liver. This may be useful in a number of situations, such as when a patient has a large liver, an abdominal cavity with limited space to maneuver, and/or when more precise control of retraction is desired. It should be appreciated that more than two graspers may be used in the same procedure, such as but not limited to three, four, five, or six graspers, or more. In these variations, for example, a plurality of graspers may be advanced into the body and be spaced apart along a peripheral edge of the tissue to releasably grasp one or more portions of a liver.

In some variations, the plurality of graspers may be coupled to one or more control elements. In some variations, a first control element may be positioned externally of the body to attract, rotate (e.g., pitch) and/or translate a first grasper toward the first control element. A second grasper may be advanced into the body through the same opening (or a second opening) using the same delivery device (or a second delivery device), releasably connected to tissue (either by gripping the tissue or by capturing it in a space between the jaws), and released from the delivery device. A second control element may then be positioned externally to the body to attract, rotate (e.g., pitch) and/or translate the second grasper toward the second control element. For example, a first set of graspers grasping a left lobe of a liver may be magnetically coupled to a first control element and a second set of graspers grasping a right lobe of a liver may be magnetically coupled to a second control element. As another example, a first grasper and a second grasper each grasping the left lobe of the liver may be magnetically coupled to the same control element located external to the abdominal cavity.

The control element (520) may be manipulated (e.g., moved axially, laterally, and/or rotated) to reposition the grasper (510) and the tissue (532). In some variations, the grasper may apply a pulling force on the grasped portion of tissue in a direction of movement of the control element. For example, the control element may pull the grasped tissue away from the opening. For example, in step 408, the control element and the magnetic field corresponding thereto may be moved over the set of ribs such that the liver bends into a folded configuration. This may create a space vacated by the grasped portion of tissue that may be accessed, visualized, and/or aid another surgical procedure (e.g., gastric procedure).

In contrast, conventional devices (e.g., straight and articulating shafted graspers) are limited in the direction and manner in which forces may be applied to move grasped tissue. The location of an access site, the amount of vacant space within a body cavity, and the geometry and/or size of an instrument may reduce the range of motion and/or the forces capable of being applied to the grasped tissue using a conventional shafted grasper. Surgeons have developed retraction movement techniques in consideration of these limitations. For example, rotation of a conventional shafted grasper towards an abdominal wall may not be possible due to the geometry and size of a grasper, shaft, and, in the case of an articulating grasper, the articulation mechanism to which the grasper is connected, and their spatial relationships relative to other body organs. That is, there may be no room, and/or no leverage, to rotate the shafted grasper in the abdominal cavity without damaging tissue. Surgeons may instead, for example, apply a pushing force to tissue using a straight-shafted grasper, which may cause damage including blunt trauma. Consequently, retraction of grasped tissue may be limited in direction due to the physical constraints of conventional devices within an abdominal cavity.

As such, patient safety and surgical experience would suggest against retracting tissue using the steps as described herein. Conventional retraction procedures allow surgeons to visualize how their physical inputs are translated into motion through an instrument providing tangible confirmation to the surgeon of the steps being performed. However, the use of the grasper, control element, and corresponding methods described herein may remove this “safety net” of tactile feedback such that the surgeon may be wary of performing movements and actions beyond those conventionally used for fear of harming the patient. This may be particularly the case when forces are applied without tactile feedback through tissue including the diaphragm, ribs, and thoracic wall, since conventional procedures are not performed through these tissues. Therefore, retraction of tissue using the portions of tissue and the direction of forces applied as described herein is neither conventionally available nor does it follow the principles of conventional retraction techniques.

As shown in FIGS. 6 and 7A-7B, the grasped portion of the liver may move anteriorly over another portion of the liver. In some variations, the set of ribs over which the control element may pass may include one or more of a fifth rib through tenth rib such as the left sixth rib and the left seventh rib. The control element may be moved in a lateral direction and/or a cephalic direction over one or more of the seventh rib through tenth rib. Additionally or alternatively, the control element may be moved over the body wall between a set of left ribs and a set of right ribs. A surgeon may thus grasp tissue and control movement of the grasper in a manner independent of a location of an access site located in the body wall inferior to the ribs. The access site cannot be located in areas over the ribs where the control element moves since forming an opening at those locations would break and/or puncture one or more of bone and the diaphragm. However, the control element may apply a force to the grasper through the thoracic wall, ribs, and diaphragm in a manner that is not possible using conventional shafted tools and is counter to conventional methods of tissue retraction that rely on force application through a direct connection through an access site.

In some variations, the control element may comprise a magnet that is movable within a control element housing and which may apply a magnetic field to the grasper within the abdominal cavity. The magnet of a control element may be manipulated (e.g., using a magnet control) to rotate, translate and/or reposition a grasper and without moving the control element. For example, the grasper may rotate in one or more of pitch, yaw, and roll through manipulation of the magnet relative to the control element.

FIG. 6 is a schematic diagram (600) of a portion of a lobe (622) of a liver (620) moved in a left-superior direction to provide access to the stomach (630). In FIG. 6, the grasper (610) may grasp an inferior portion of segment III (622) of the liver (620) and may be moved in a generally cephalic direction (612) (e.g., left-superior direction) to pull at least the grasped portion (622) of the liver in the cephalic direction. In this manner, the grasped portion of liver (622) may be moved anteriorly over another portion of the left lobe of the liver (620). This may create a space in the abdominal cavity vacated by the moved portion of tissue (622) and provide an area (632) of improved access including a portion of the stomach (630) underneath the liver (620). As described in further detail herein, the stomach (630) may be accessed through one or more of visualization using an optical sensor and a gastric procedure.

FIGS. 7A-7B are schematic diagrams (700) of a portion of a lobe (722) of a liver (720) moved in a lateral direction to provide access to an area (732) of the stomach (730). For example, the grasper (710) may grasp a left-lateral portion of a segment II portion (722) of the liver (720) and may be moved in a generally lateral direction (712) to pull at least the grasped portion (722) of the liver laterally (e.g., from the patient's left to the patient's right). In FIG. 7B, a control element (not shown) may be further moved laterally over the ribs (not shown) such that the grasped portion (722) of the liver (720) may be moved anteriorly over a right lobe of the liver (not shown). This may create a space in the abdominal cavity vacated by the moved portion of tissue (722) and provide an accessible area (732) corresponding to a portion of the stomach (730) underneath the liver (720). As described in further detail herein, the stomach (730) may be accessed through one or more of visualization using an optical sensor and a gastric procedure.

In some variations, the methods described here may additionally or alternatively comprise using a visualization device (e.g., optical sensor, camera, light source) to visualize a body cavity during a minimally-invasive procedure. In step 410, a space vacated by the moved portion of the liver may be visualized using an optical sensor such as those described in more detail herein. As shown in FIG. 12E, a visualization device comprising a camera (1250) may be advanced into the body with a lens (1252) directed towards a target tissue (1202). To advance the camera (1250), the camera (1250) may be releasably coupled to a distal engagement portion of a delivery device, and a user may advance the distal engagement portion into the body to position the camera (1250). Once in position, the camera (1250) may be released from the delivery device, and the delivery device may be removed from the body. In some variations, the method may return to step 404 to grasp and manipulate a different portion of tissue and/or step 408 to further move the grasper after visualization. This may be useful when modification to tissue traction is desired.

In some variations, access to tissue may be improved using the force of gravity to shift organs to a desired arrangement within an abdominal cavity. In step 412, a patient may optionally be tilted to shift one or more organs within the abdominal cavity to provide access to tissue within the abdominal cavity. In some variations, a superior portion of a patient may be tilted above an inferior portion of the patient. For example, a patient on a patient platform (e.g., operating table) may be tilted (e.g., pitched, rolled) such that the patient's head is above his/her feet. In some variations, the control element may remain stationary relative to a body wall of the abdominal cavity while tilting the patient. For example, the control element may be coupled to a mechanical arm further coupled to the patient platform. When the patient platform is tilted, the arm and control element may tilt along with the patient platform. In this manner, one or more organs other than the suspended tissue (e.g., grasped lobe of the liver) may move inferiorly relative to the liver and thus provide access to tissue other than the suspended tissue. For example, tilting the patient may allow a set of organs posterior to the liver (e.g., stomach, gallbladder) to move in a caudal direction (e.g., toward the feet) while the grasped liver tissue remains stationary relative to the body wall of the abdominal cavity.

In some variations, the patient may be tilted by up to about 60 degrees relative to ground. In some variations, the patient may be tilted by up to about 30 degrees relative to ground. Additionally or alternatively, the control element may be repositioned (e.g., by moving the control element relative to the ribs) while tilting the patient. Tissue within the abdominal cavity may be visualized while the patient is tilted and/or the control element is repositioned. In some variations, the patient may be tilted and the control element may be moved iteratively to manipulate the liver and other tissue. This may enlarge a space vacated by the liver. Tilting of a patient while using a conventional shafted instrument may be difficult since a surgeon would need to manually adjust a position and/or orientation of the traction instrument within the body cavity as the patient is tilted.

In some variations, the method may return to step 404 to grasp and manipulate a different portion of tissue. In some instances, the delivery device (or another device, such as a grasping device) may be used to disconnect the grasper from tissue. The grasper may then be repositioned and reattached to tissue (either the same tissue or a different tissue), or may be removed from the body.

In some variations, remote traction of tissue may aid tissue visualization and/or other procedures to be performed. In step 414, a space in the abdominal cavity vacated by the grasped portion of the liver may be accessed. Access may allow a procedure to be performed in the space such as visualization or a gastric procedure, as described in more detail herein. In some variations, the space may comprise a stomach and/or tissue posterior to the grasped portion of the liver. For example, tissue retraction may be followed by controlling the position and/or orientation of one or more of a grasper, retractor, light sources, sensors (e.g., ultrasound), scissors, electrocautery devices, and the like, located within the body using a magnetic field generated outside the body by a control element as described herein.

In step 416, a procedure, such as a gastric procedure, may optionally be performed while the liver is in a folded configuration. In some variations, the gastric procedure may comprise one or more of a gastric bypass, a sleeve gastrectomy, a gastric band procedure, a biliopancreatic diversion with duodenal switch, and a gastric cancer resection. During a gastric procedure, the control element may remain stationary or be repositioned over the set of ribs as necessary to aid different steps of a gastric procedure.

In step 418, the grasper may be released from the liver. In some variations, the control element may be moved over the set of ribs back to the location where the grasper and control element were initially magnetically coupled. This may allow the grasped portion of the liver to return closer to its natural position. In some variations, a delivery device or retraction device may be introduced into the abdominal cavity through the access site and advanced to couple to the grasper. The delivery device may then couple to the grasper. The jaws of the grasper may then release the grasped portion of the liver (e.g., via actuation by the delivery device). In step 420, the grasper coupled to the delivery device may be removed from the abdominal cavity such as through an opening (e.g., the opening through which the grasper was introduced).

Biliopancreatic Diversion with Duodenal Switch

In some variations, liver traction may be performed to aid visualization of a gastric procedure such as a biliopancreatic diversion with duodenal switch. A biliopancreatic diversion procedure with duodenal switch may include the steps of performing a sleeve gastrectomy and cutting a pylorus from a duodenum.

The biliopancreatic diversion may begin with introducing a grasper through an opening into the abdominal cavity (step 402). The grasper may grasp a left-lateral portion of a segment II portion of the liver (step 404). The control element may be moved in a generally lateral direction over the ribs to pull at least the grasped portion of the liver laterally (step 408). In some cases, the grasper and grasped portion of the liver may be folded over the right lobe of the liver. Alternatively, the grasper may grasp an inferior portion of segment III of the liver and may be moved in a generally cephalic direction (e.g., left-superior direction) to pull at least the grasped portion (622) of the liver anteriorly over another portion of the left lobe of the liver.

Retraction of the liver may create a space in the abdominal cavity for visualizing a body of a stomach (step 410). In some variations, the patient may be tilted to further aid separation between the liver and stomach (step 412). The gastric procedure may be performed (416). Specifically, a sleeve gastrectomy may be performed with the aid of the moved portion of the liver. During the sleeve gastrectomy or any step of a gastric procedure, the method may optionally return to steps 408 and/or 412 to reposition the grasped tissue. This may be useful if the position of the organs changes and/or a surgeon desires a different field of view of the abdominal cavity.

In some variations, different portions of the liver may be retracted separately in order to increase access to specific areas underneath the liver. For example, one or more of segments II and III of the liver may be retracted to aid visualization of a body of a stomach while one or more of segments IV, V, and VI of the liver may be retracted to aid visualization of a pylorus and duodenum. Accordingly, once a sleeve gastrectomy is completed, the grasper may release the portion of the liver and grasp a different portion of the liver to aid the pylorus cutting step of the gastric procedure. For example, the control element may be moved in a reverse direction across the ribs to bring the grasped segment II portion of the liver back closer to its original position. The grasper may release its connection to tissue (e.g., through control by a delivery device and/or secondary grasper) and then be moved by the control element towards one or more of segments IV, V, and VI of the right lobe of the liver.

In some variations, an inferior portion of one or more of segments IVb, V, and VI of the right lobe of the liver may be grasped by the grasper (step 404) and moved in a generally lateral or cephalic direction (step 408) to pull at least the grasped portion of the liver anteriorly over another portion of the liver to expose the pylorus and duodenum. Retraction of the liver may create a space in the abdominal cavity for visualizing the pylorus and duodenum (step 410). In some variations, the patient may be tilted to further aid separation between the liver and stomach (step 412). The pylorus may be cut from the duodenum (step 416). The grasper may release its connection to the liver (step 418) and be removed from the abdominal cavity (step 420).

II. Systems and Devices

Figure 8A:
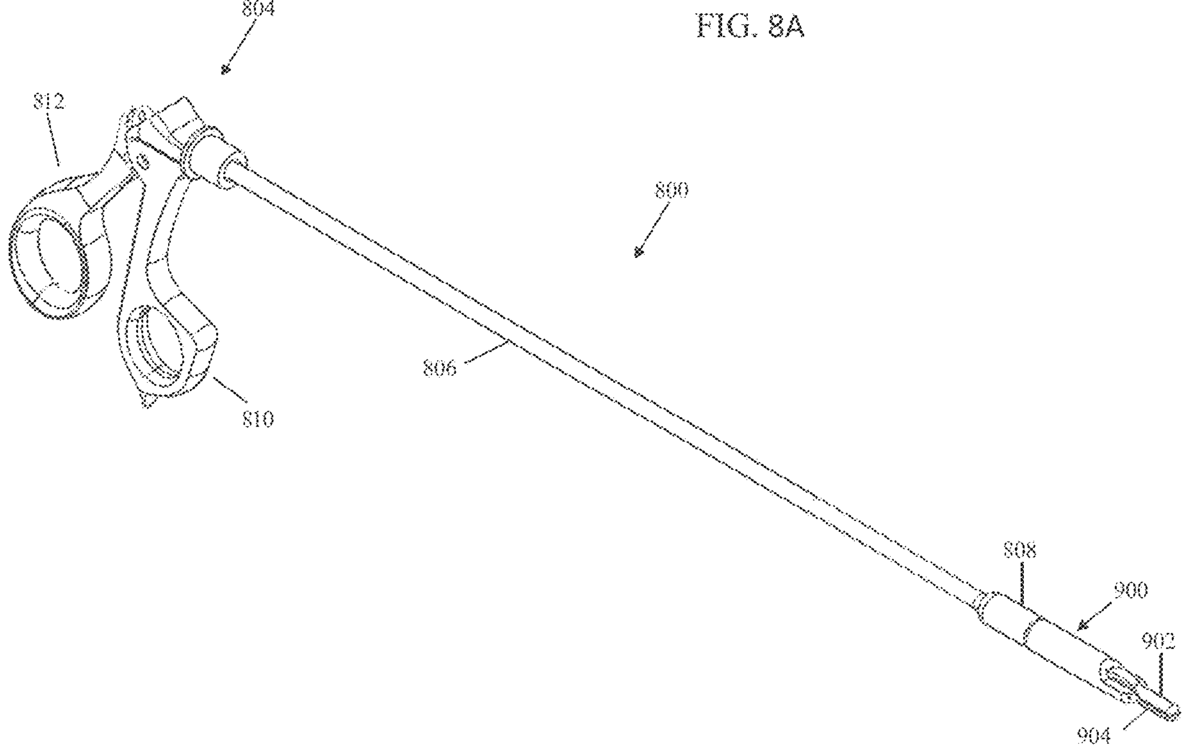
FIGS. 8A-8C depict perspective views of an illustrative variation of the systems described here.
Figure 8B:
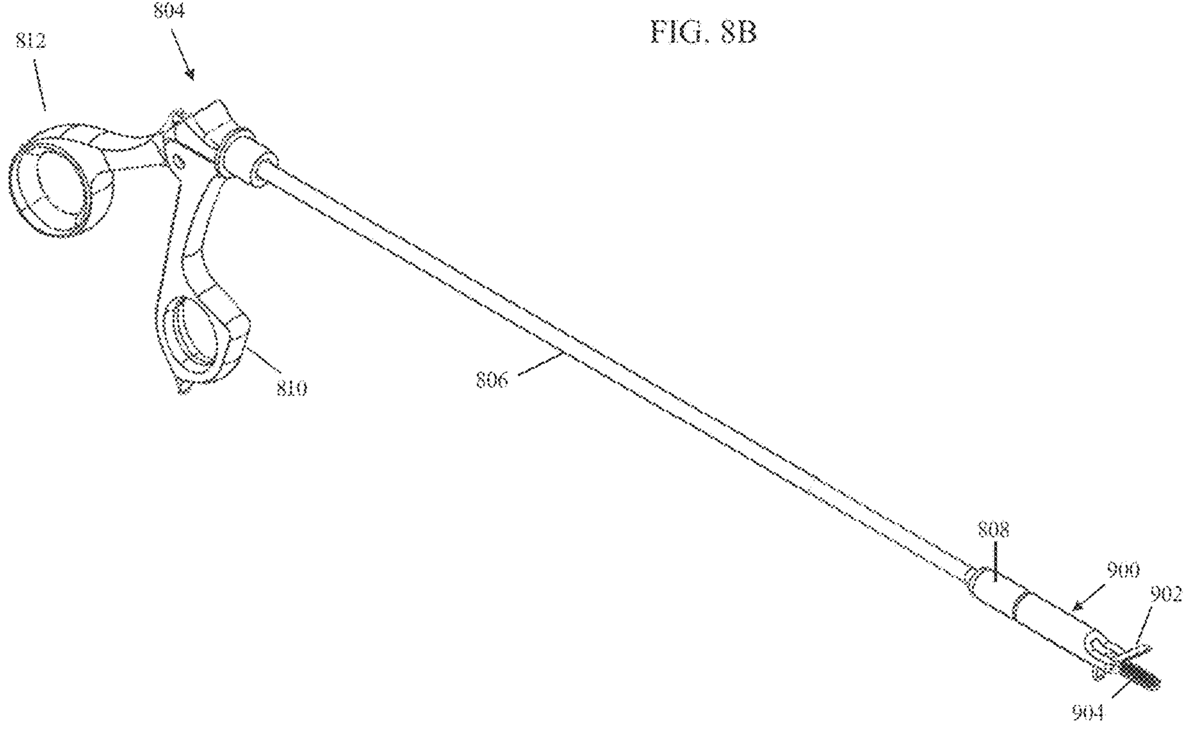
Figure 8C:
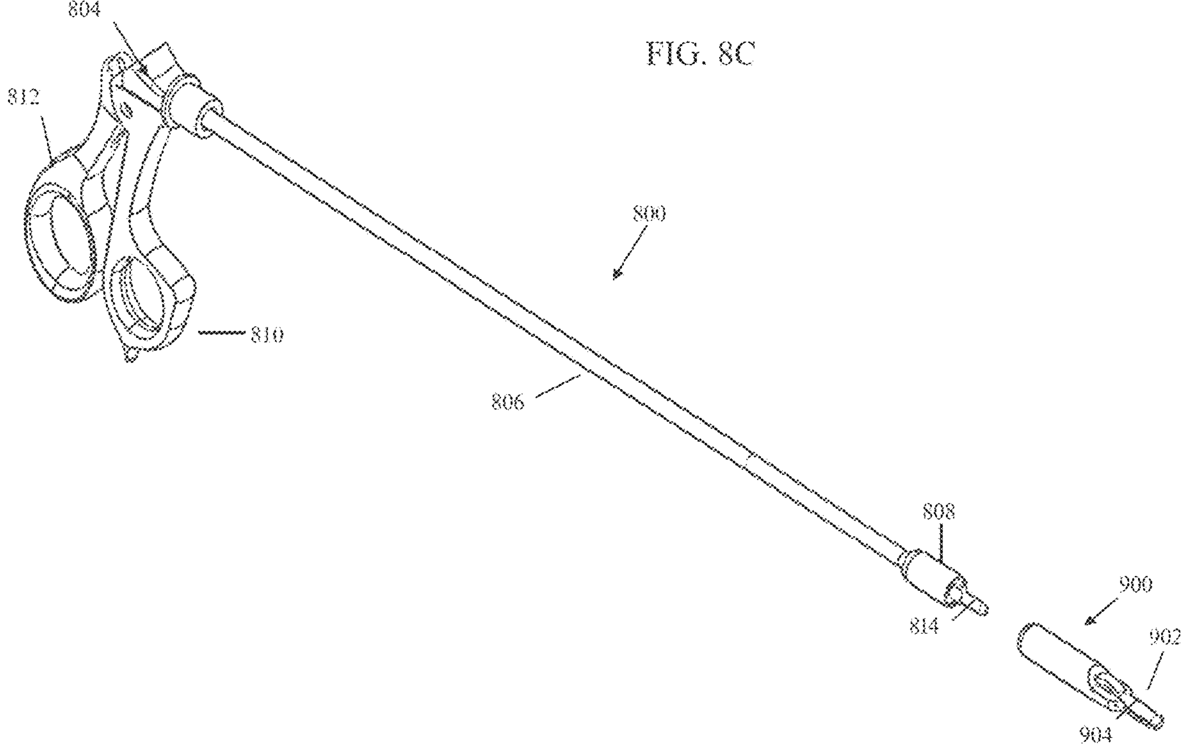

The graspers and systems described herein may be used in the procedures described herein including any suitable minimally invasive procedure, such as but not limited to abdominal procedures, thorascopic procedures, bariatric procedures, and urological/gynecological procedures. The devices and systems described here may include the devices described in U.S. application Ser. No. 14/019,370, filed Sep. 5, 2013, now issued as U.S. Pat. No. 8,764,769, in International Application Serial No. PCT/US2015/012319, filed Jan. 21, 2015, or in International Application Serial No. PCT/US2016/027390, filed Apr. 13, 2016, each of which was previously incorporated by reference. FIGS. 8A-AC depict one variation of the systems described here. Specifically, FIG. 8A shows a perspective view of a system comprising a delivery device (800) and a grasper (900). The grasper (900) may be releasably coupled to the delivery device (800) (as shown in FIGS. 8A and 8B), and may be decoupled from the delivery device (800) (as shown in FIG. 8C). When the grasper (900) is coupled to the delivery device (800), the delivery device (800) may actuate the grasper to connect the grasper to tissue and/or release the grasper therefrom.

As shown in FIG. 8A, the delivery device (800) may comprise a handle (804), a shaft (806) extending from the handle (804), and a distal engagement portion (808) at a distal end of the shaft (806). In some variations, the delivery device (800) and grasper (900) may be configured for minimally invasive introduction into a body. For instance, in some variations the grasper (900) and delivery device (800) may be configured for advancement through a 10 mm port. In these variations, the outer diameter of the grasper (900) may be less than or equal to about 10 mm. Additionally, the delivery device (800) may be configured such that the shaft (806) and the distal engagement portion (808) may each have a diameter of less than or equal to about 10 mm.

In some of these variations, the distal engagement portion (808) may have an outer diameter of less than or equal to about 10 mm, while the shaft (806) has an outer diameter of less than or equal to about 5 mm. In these variations, it may be possible to advance the distal engagement portion (808) through a 10 mm port, and to further advance a second device having a diameter of about 5 mm or less through the port while the shaft (806) is positioned in the port.

It should be appreciated that shaft (806) may have any suitable diameter (e.g., between about 1 mm and about 15 mm, between about 5 mm and about 10 mm, or the like). The shaft (806) and distal engagement portion (808) may be formed from any suitable materials, such as one or more medical-grade, high-strength plastics or metals, such as stainless steel, cobalt chromium, PEEK, one or more nylons, polyimide, polycarbonate, ABS, or the like.

It should be appreciated that the systems disclosed herein may comprise a delivery device (800) releasably coupled to a different device than a grasper (900), in order to perform one or more functions within an abdominal cavity.

A. Tissue Grasping

1. Actuation Control Mechanism

Generally, the handle (804) comprises an actuation control mechanism that may be manipulated by a user to controllably actuate the grasper (900). In some variations, the delivery device (800) may comprise a separate decoupling control, which a user may use to decouple the grasper (900) from the delivery device (800). In other variations, the delivery device (800) may be configured such that a user may use the actuation control mechanism to decouple the grasper (900) from the delivery device (800) in addition to actuating the grasper (900). For example, in the variation of the delivery device (800) depicted in FIGS. 8A-8C, the handle (804) of delivery device (800) may comprise a grip portion (810) and an actuation control mechanism comprising a trigger (812). While shown in FIGS. 8A-8C as being a trigger (812), it should be appreciated that the actuation control mechanism may comprise any suitable control element (e.g., a slider, a knob, or the like) capable of actuating the grasper (900) as described in more detail below. The trigger (812) may be configured to both actuate the grasper (900) and decouple the grasper (900) from the delivery device (800).

Specifically, in some variations the trigger (812) may be moveable between three positions. While three distinct positions will be discussed below, it should be appreciated that the trigger (812) may also assume one or more intermediate positions between these positions. Of the three positions, the trigger (812) may be moveable between a first position (as shown in FIG. 8A) and a second position (as shown in FIG. 8B) to actuate the grasper (900). Specifically, the grasper (900) may comprise a first jaw (902) and a second jaw (904), and at least one of the first jaw (902) and the second jaw (904) may be configured to rotate relative to the grasper (900). The grasper (900) may be actuated between an open configuration and a closed configuration.

In the open configuration, the first jaw (902) and second jaw (904) may be held in rotationally separated positions to define a space between the first jaw (902) and the second jaw (904), as shown in FIG. 8B. In the closed configuration, the first jaw (902) and second jaw (904) may be rotationally biased toward each other, as shown in FIG. 8A. While the first jaw (902) is shown in FIG. 8A as contacting the second jaw (904) when the grasper (900) is in the closed configuration, it should be appreciated that when the grasper (900) is connected to tissue, tissue positioned between the first jaw (902) and second jaw (904) may prevent the first jaw (902) from contacting the second jaw (904) when the grasper (900) is in the closed configuration.

The grasper (900) may be actuated between the closed and open configurations to releasably connect the grasper (900) to tissue. For example, when the trigger (812) is in the first position (as shown in FIG. 8A), the grasper (900) may be placed in the closed configuration. As the trigger (812) is moved to the second position (as shown in FIG. 8B), the grasper (900) may be moved to the open configuration. In variations where the first jaw (902) is configured to rotate relative to the grasper (900), moving the trigger (812) from the first position to the second position may rotate the first jaw (902) away from the second jaw (904), while moving the trigger (812) from the second position back to the first position may rotate the first jaw (902) toward the second jaw (904). Accordingly, by moving the trigger (812) between the first and second positions, a user may selectively open and close the jaws (902, 904) of the grasper (900) using the delivery device (800). To connect the grasper (900) to tissue, a user may place the trigger (812) in the second position (or an intermediate position between the first and second positions) to open (or partially open) the jaws (902, 904), and may manipulate the delivery device (800) to position tissue between the first jaw (902) and the second jaw (904). With the tissue positioned between the jaws (902, 904), the trigger (812) may be returned to the first position to close the jaws (902, 904) to clamp the jaws (902, 904) against the tissue, thereby releasably connecting the grasper (900) to the tissue.

As mentioned above, the trigger (812) in some variations may be configured to decouple the grasper (900) from the delivery device (800). For example, the trigger (812) may be moved from the first position (as shown in FIG. 8A) to a third position (as shown in FIG. 8C), and the delivery device (800) may be configured to decouple from the grasper (900) when the trigger (812) is moved to the third position (as will be described in more detail below). When the same actuation control mechanism is used to actuate the grasper (900) and decouple the grasper (900) from the delivery device (800), it may be desirable to decouple the grasper (900) from the delivery device (800) when the grasper (900) is in a closed configuration and engaged with tissue. Accordingly, in some variations, the first position of the trigger (812) (which may correspond to a closed configuration of the grasper (900)) may be an intermediate position between the second position and third position. In these variations, when the trigger (812) is placed in the second position to place the grasper (900) in an open configuration, the trigger (812) will move through the first position (which may move the grasper (900) to a closed configuration) before it reaches the third position. Thus the grasper (900) may be moved to the closed configuration before it is decoupled from the delivery device (800).

Figures 9A, 9B:
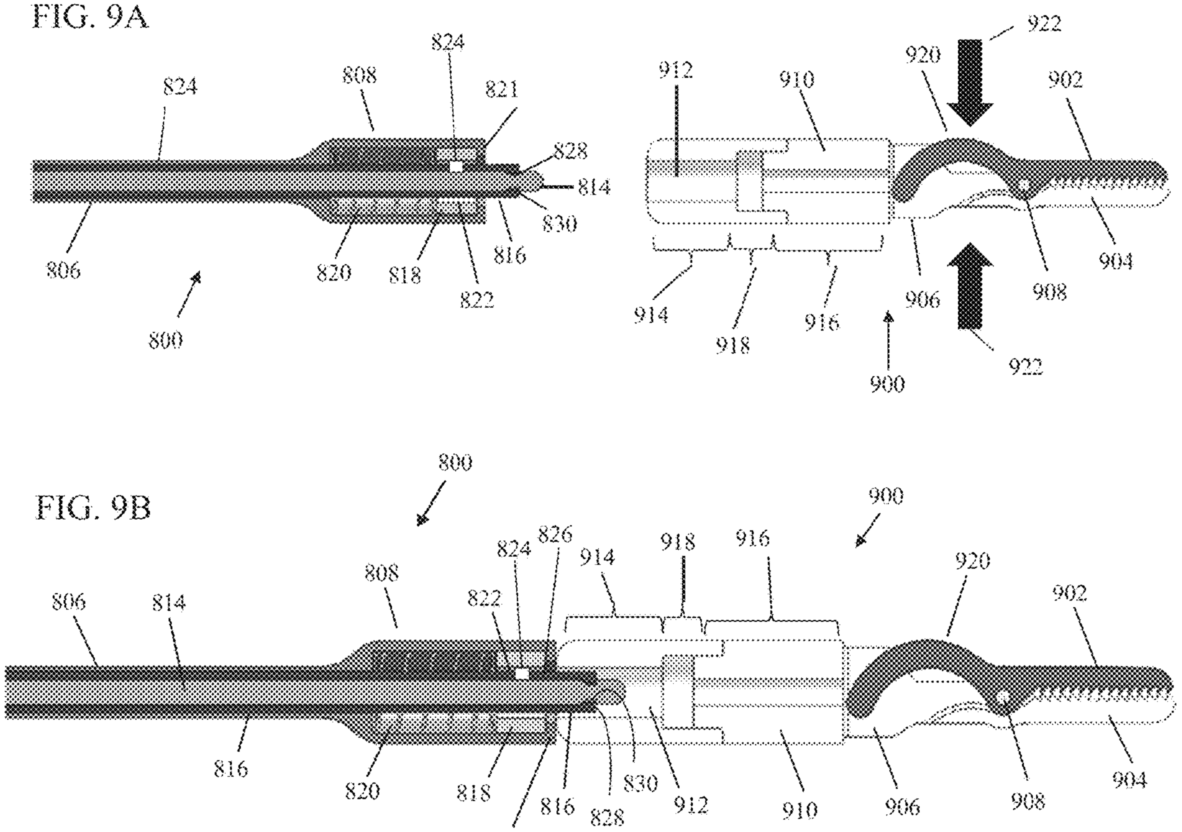
FIGS. 9A-9F depict cross-sectional side views of a distal portion of an illustrative variation of the delivery devices described here and an illustrative variation of the graspers described here.

The delivery devices described here may be configured to actuate, couple to, and decouple from, the graspers described here in any suitable manner. For example, FIGS. 9A-9F illustrate one suitable mechanism by which a delivery device may be configured to actuate and couple/decouple a grasper. For example, FIG. 9A depicts a cross-sectional side view of variations of the grasper (900) and a distal portion of the delivery device (800) each described above with respect to FIGS. 8A-8C. As shown there, the grasper (900) may comprise a first jaw (902), a second jaw (904), and a main body (906). Generally, the first jaw (902) is rotatably connected to the main body (906) at a pivot point (908), such that the first jaw (902) may rotate relative to the main body (906). In some variations (such as that shown in FIGS. 9A-9F), the second jaw (904) may be fixed relative to the main body (906), while in other variations the second jaw (904) may also be rotatably connected to the main body (906). When the second jaw (904) is fixed relative to the main body (906), the second jaw (904) may be formed separately from the main body (906) and subsequently attached thereto, or may be formed integrally with the main body (906). When a jaw as described here is configured to rotate relative to a pivot point, the jaw may be configured to rotate in any suitable manner. In some variations, a jaw (902) may be connected to the main body (906) via a rotation pin (908), such that the jaw (902) may rotate around the rotation pin (908) (or the jaw (902) and rotation pin (908) may rotate relative to the main body (906)). In other variations, the jaw may be connected to the main body via a living hinge.

The first jaw (902) and second jaw (904) may be rotationally biased toward each other (e.g., towards a closed configuration). In variations where the first jaw (902) is rotatably connected to the main body (906), the first jaw (902) may be rotationally biased toward the second jaw (904). For example, in some variations the grasper (900) may comprise a spring such as a torsional spring or a cantilever spring (not shown), which may spring-bias the first jaw (902) toward the second jaw (904). In variations where the second jaw (904) is rotatably connected to the main body (906), the second jaw (904) may also be biased towards the first jaw (902) (e.g., via one or more springs). The bias of the jaws (902, 904) toward the closed configuration may act to hold tissue positioned between the first jaw (902) and the second jaw (904).

As shown in FIG. 9A, the main body (906) of the grasper (900) may comprise a barrel portion (910) with a lumen (912) extending therethrough. A portion of the delivery device (800) may be advanced through the lumen (912) to rotate first jaw (902) (and in some instances, the second jaw (904) in variations where the second jaw (904) is rotatably connected to the main body (906)) relative to the main body (906), as will be described in more detail below. In some variations, the lumen (912) may have a constant diameter. In other variations, different portions of the lumen (912) may have different diameters.

For example, in the variation of the grasper (900) shown in FIGS. 9A-9F, the lumen (912) of the barrel portion (910) may comprise a proximal segment (914), a distal segment (916), and an intermediate segment (918) positioned between the proximal segment (914) and the distal segment (916). As shown in FIG. 9A, the proximal segment (914) may have a larger diameter than the distal segment (916), and the intermediate segment (918) may have a larger diameter than both the proximal segment (914) and the distal segment (916). The proximal (914), distal (916), and intermediate (918) segments may aid in maintaining a coupling with the delivery device (800), as will be described in more detail below.

The barrel portion (910) of the grasper (900) may be sized and configured to be engaged by the distal engagement portion (808) of the delivery device (800) to releasably couple the grasper (900) to the delivery device (800). In some variations, the outer diameter of the barrel portion (910) may have a constant diameter, or may have different portions of the barrel portion (910) having different diameters, such as described in more detail below. Turning to the delivery device (800), in the variation of the delivery device shown in FIGS. 9A-9F, the delivery device (800) may comprise an actuation rod (814) slidably disposed in the shaft (806). The actuation rod (814) may be advanced through the lumen (912) of the barrel portion (910) of the grasper (900) to actuate the grasper (900), as will be described in more detail below. Also shown in FIG. 9A is a locking sheath (816), a coupling magnet (818), and a spring (820). Each of these components will be discussed further below.

Figure 9C:
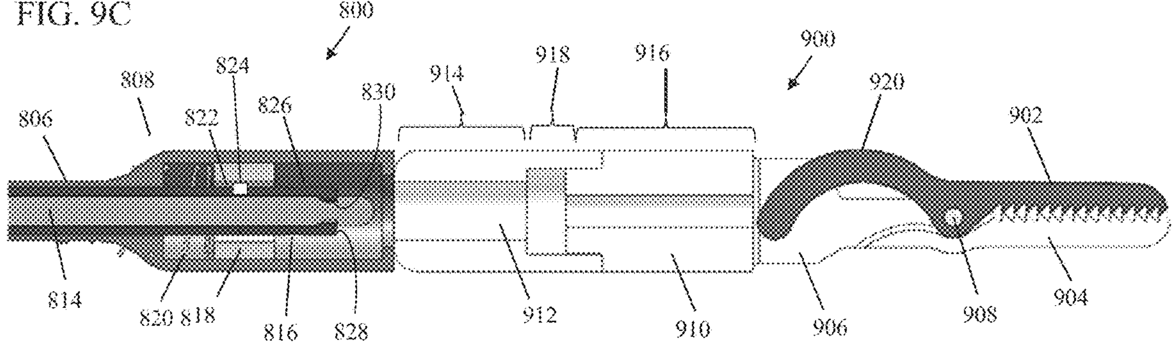

While shown in FIGS. 9A-9F as having a coupling magnet (818), the delivery device (800) need not comprise a coupling magnet. In variations of the delivery device (800) that do comprise a coupling magnet (818), the coupling magnet (818) may be slidably housed in a housing of the distal engagement portion (808), and may be configured to releasably couple the delivery device (800) to the grasper (900). The coupling magnet (818) may be movable between an advanced position (as depicted in FIG. 9A) and a retracted position (as depicted in FIG. 9C). In variations where the delivery device (800) comprises a spring (820), the spring (820) may be positioned in the distal engagement portion (808) to bias the coupling magnet (818) toward the advanced position.

The delivery device (800) may be configured to couple to the grasper (900) when the coupling magnet (818) is in the advanced position. For example, when the distal engagement portion (808) is brought near the grasper (900), the coupling magnet (818) may attract the grasper (900). Generally, at least a portion of the graspers described here are formed from one or more materials that may be attracted to a magnetic field. The materials may include one or more permanent magnets, or one or more ferromagnetic or ferrimagnetic materials, such as, for example, stainless steel, iron, cobalt, nickel, neodymium iron boron, samarium cobalt, alnico, ceramic ferrite, alloys thereof and/or combinations thereof. The particular configuration of the materials within the grasper—for example, the type, amount, polarity, and location of the materials—may alter how the grasper responds to and/or interacts with a control element, and is discussed in more detail below.

Accordingly, one or more portions of the grasper (900) may be formed from or otherwise include a material that may be attracted to a magnetic field produced by the coupling magnet (818). The attractive force provided by the coupling magnet (818) may hold the grasper (900) against or at least partially within the distal engagement portion (808), such as shown in FIG. 9B. The grasper (900) may be positioned such that a proximal end of the barrel portion (910) of the grasper (900) is held against or at least partially within the distal engagement portion (808) of the delivery device (800).

To decouple the grasper (900) from the distal engagement portion (808), the coupling magnet (818) may be withdrawn to the retracted position, as shown in FIG. 9C. Because the attractive force applied by a magnet decreases as a function of the distance from the magnet, moving the coupling magnet (818) to the retracted position (e.g., by an actuation control mechanism) may increase the distance between the grasper (900) and the coupling magnet (818) (e.g., the distal engagement portion (808) may comprise a stop (821) which may prevent the grasper (900) from being retracted with the coupling magnet (818)), which may reduce the attractive force applied to the grasper (900). Eventually, the attractive force may be sufficiently diminished such that the grasper (900) may decouple from the delivery device (800).

Nevertheless, the coupling magnet (818) may be retracted in any suitable manner. In some variations, the delivery device (800) may comprise a control sheath (not shown) which may be attached to the coupling magnet (818). The control sheath may be selectively withdrawn or advanced from the grasper (900) (e.g., via a control mechanism in the handle (804)) to withdraw and advance, respectively, the coupling magnet (818). In other variations, a portion of the actuation rod (814) may be configured to retract the coupling magnet (818). For example, the actuation rod (814) may be configured to catch on or otherwise engage the coupling magnet (818) during retraction of the actuation rod (814). In these variations, the actuation rod (814) may be withdrawn until the actuation rod (814) engages the coupling magnet (818). Once the actuation rod (814) engages the coupling magnet (818), further withdrawal of the actuation rod (814) may also withdraw the coupling magnet (818).

For example, as shown in FIGS. 9A-9F, the actuation rod (814) may be slidably disposed within a lumen (822) of the coupling magnet (818). In some variations, at least a segment of the actuation rod (814) may be sized and configured such that the portion of the actuation rod (814) cannot fully pass through the lumen (822). For example, in some variations a segment of the actuation rod (814) may have a diameter greater than a diameter of the lumen (822). Additionally or alternatively, the segment may comprise one or more projections extending from an outer surface of the actuation rod (814) and which cannot fully pass through the lumen (822). When the segment of the actuation rod (814) is positioned distal to the coupling magnet (818), the actuation rod (814) may be freely advanced relative to the coupling magnet (818). Conversely, withdrawal of the actuation rod (814) may pull the segment of the actuation rod (814) into contact with the coupling magnet (818). Since the segment cannot fully pass through the lumen (822) of the coupling magnet (818), further withdrawal of the actuation rod (814) may cause the segment of the actuation rod (814) to pull on and withdraw the coupling magnet (818). When the actuation rod (814) is subsequently advanced, the spring (820) may advance the coupling magnet (818) with the actuation rod (814) until the coupling magnet (818) reaches the advanced position.

In variations where the delivery device (800) comprises a locking sheath (816) slidably disposed in the lumen (822) of the coupling magnet (818), the locking sheath (816) may be configured to withdraw the coupling magnet (818). For example, a segment of the locking sheath (816) may be sized and configured such that the segment cannot fully pass through the lumen (822) of the coupling magnet (818), such as described above with respect to the actuation rod (814). In the variation shown in FIGS. 9A-9F, the locking sheath (816) may comprise a protrusion (824) positioned distally of the coupling magnet (818) and sized such that the protrusion (824) cannot fully pass through the lumen (822). In these variations, proximal withdrawal of the locking sheath (816) through the lumen (822) may place the protrusion (824) into contact with the coupling magnet (818), such as shown in FIGS. 9A and 9B. As depicted in FIG. 9C, further withdrawal of the locking sheath (816) may also withdraw the coupling magnet (818) (e.g., by virtue of the contact between the protrusion (824) and the coupling magnet (818)).

As mentioned above, the delivery devices described here may comprise a locking sheath (although it should be appreciated that in some variations the delivery device may not comprise a locking sheath). In variations where the delivery device does comprise a locking sheath (816), such as the variation of the delivery device (800) depicted in FIGS. 9A-9F, the locking sheath (816) may be slidably disposed in the shaft (806). The actuation rod (814) may in turn be positioned at least partially within the locking sheath (816). The locking sheath (816) may comprise an expandable distal portion (826) which may be configured to expand inside of the lumen (912) of the barrel portion (910) of the grasper (900) to temporarily engage an interior portion of the lumen (912), which may help maintain the coupling between the grasper (900) and the delivery device (800).

In these variations, the delivery device (800) may be configured such that advancement of the actuation rod (814) relative to the locking sheath (816) may expand the expandable distal portion (826) of the locking sheath (816). For example, the expandable distal portion (826) of the locking sheath (816) may comprise at least one internal projection (828) that projects inwardly and is sized and shaped to fit within at least one corresponding indentation (830) in the outer surface of the actuation rod (814). It should be appreciated that at least one internal projection (828) may be a single projection (e.g., an annular snap-fit or a projection that extends radially around some or all of the inner circumference of the locking sheath (816)) or multiple discrete projections. Similarly, the actuation rod (814) may comprise a single indentation (e.g., an indentation that extends radially around some or all of the outer surface of actuation rod (814)) or multiple indentations.

The actuation rod (814) may be positioned within the locking sheath (816) such that the internal projections (828) of the locking sheath (816) are positioned in corresponding indentations (830) of the actuation rod (814), such as shown in FIGS. 9A-9D. This may create a friction fit or mechanical interlock between the actuation rod (814) and the locking sheath (816), which may cause the locking sheath (816) to be advanced and withdrawn with the actuation rod (814).

The engagement between the actuation rod (814) and the locking sheath (816) may be further configured such that under certain circumstances the actuation rod (814) may be advanced relative to the locking sheath (816) to expand the expandable distal portion (826) of the locking sheath (816). For example, as shown in FIGS. 9A-9F, the internal projections (828) of the locking sheath (816) and the corresponding indentations (830) of the actuation rod (814) may each have a ramped proximal portion. When the internal projections (828) are positioned within corresponding indentations (830), the ramped proximal portion of each internal projection (828) may be positioned in contact with the ramped proximal portion of a corresponding indentation (830). This contact may provide the friction fit or mechanical interlock that may allow the actuation rod (814) to distally advance the locking sheath (816) as mentioned above.

When an external force is applied to the locking sheath (816) to resist distal advancement of the locking sheath (816), advancement of the actuation rod (814) may overcome the friction force or mechanical connection between the ramped proximal portions of the internal projections (828) and the corresponding indentations (830), at which point the contacting ramped surfaces may slide relative to each other as the actuation rod (814) begins to advance distally relative to the locking sheath (816). As the actuation rod (814) is advanced distally relative to the locking sheath (816), the internal projections (828) may slide out of their corresponding indentations (830) (such as shown in FIG. 9E), which may thereby expand the expandable distal portion (826) of the locking sheath (816).

Figure 9D:
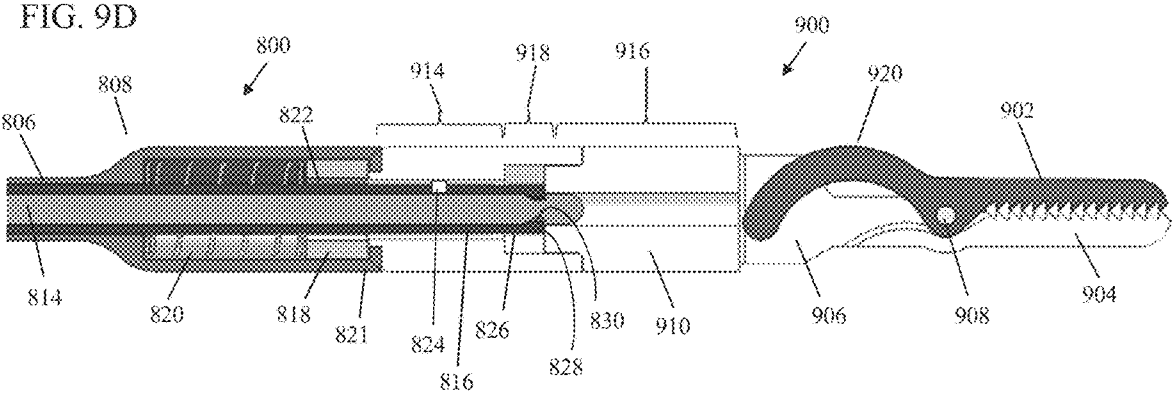
Figure 9E:
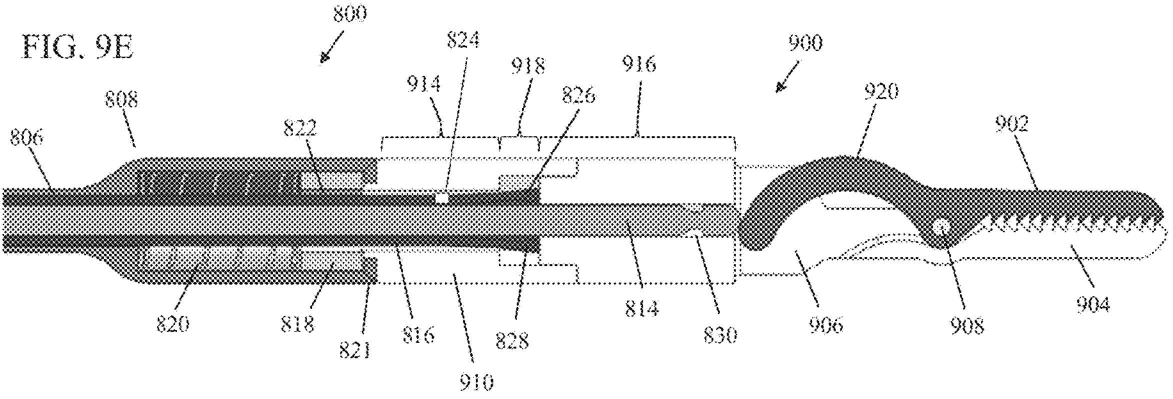
Figure 9F:
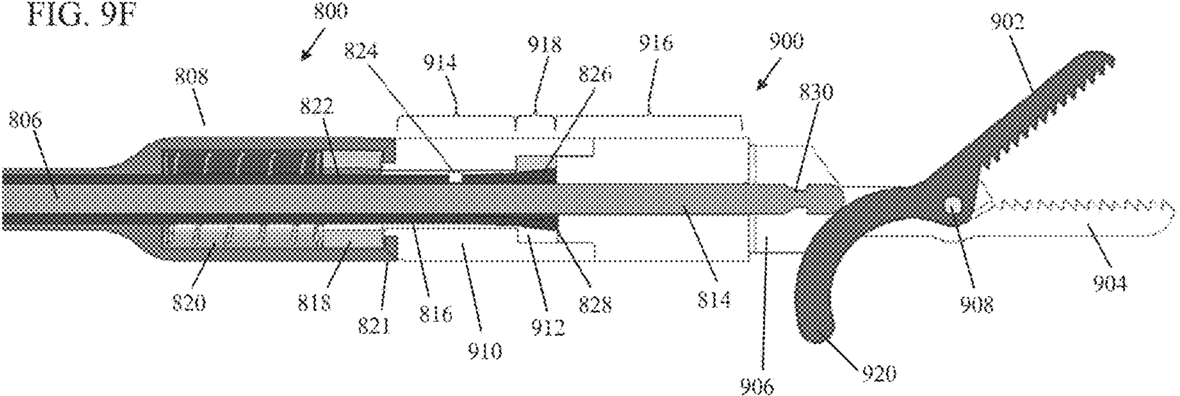
Figures 10A, 10B:
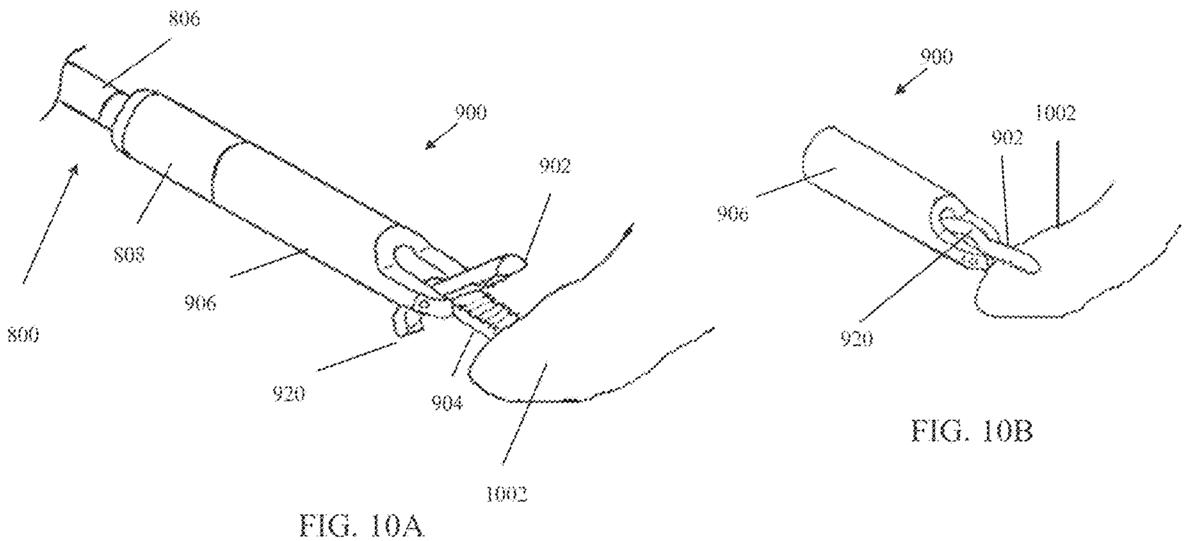
FIGS. 10A-10D depict illustrative variations of the methods described here.
Figures 10C, 10D:
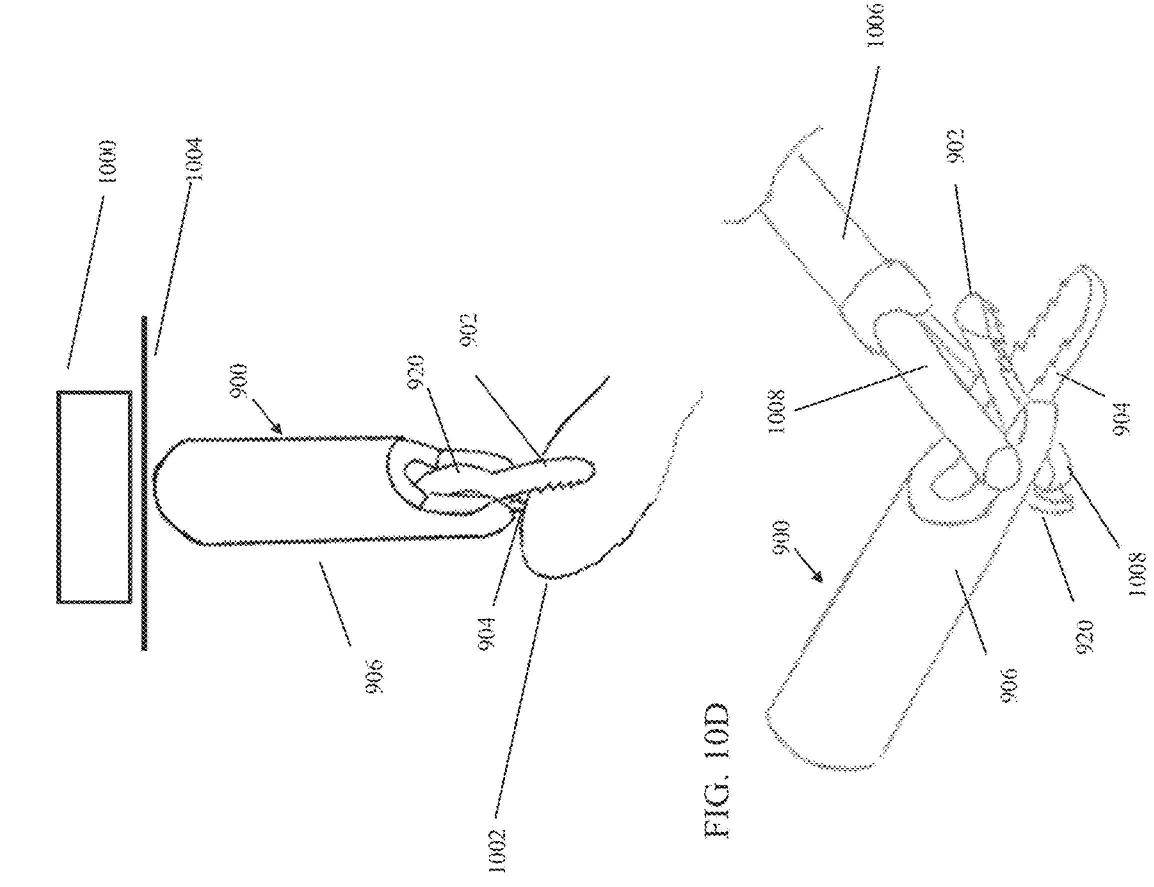

This expansion of the expandable distal portion (826) of the locking sheath (816) may help to maintain the temporary coupling between the delivery device (800) and the grasper (902), as illustrated in FIGS. 9D-9F. Specifically, the locking sheath (816) and actuation rod (814) may be positioned such that the internal projections (828) of the locking sheath (816) are positioned in respective indentations (830) on the actuation rod (814), which may allow advancement and retraction of the actuation rod (814) to advance and retract the locking sheath (816), as discussed above. The grasper (900) may be coupled to the distal engagement portion (808) of the delivery device (800), as shown in FIG. 9C, and the actuation rod (814) may be advanced to begin advancing the actuation rod (814) and locking sheath (816) into the lumen (912) of the barrel portion (910) of the grasper (900). The actuation rod (814) may be sized such that it is smaller than each of the proximal segment (914), the distal segment (916), and the intermediate segment (918) of the lumen (912) of the barrel portion (910) of the grasper (900). This may allow the actuation rod (814) to be advanced through the entire lumen (912) of the barrel portion (910). The locking sheath (816), however, may be sized and configured such that it may pass through the proximal segment (914) and the intermediate segment (918) of the lumen (912), but is prevented from entering the distal segment (916). Accordingly, the actuation rod (814) may be advanced to advance the actuation rod (814) and the locking sheath (816) through the lumen (912) of the barrel portion (910) of the grasper (900) until the locking sheath (816) reaches the distal segment (916) of the lumen (912), as shown in FIG. 9D. At this point, the locking sheath (816) may be prevented from entering the distal segment (916), and may thus be prevented from further advancement.

The actuation rod (814) may be further advanced relative to the grasper (900) to advance the actuation rod (814) through the distal segment (916) of the lumen (912). Because the locking sheath (816) is prevented from advancing further, the actuation rod (814) may be advanced relative to the locking sheath (816). This may cause the internal projections (828) of the locking sheath (816) to slide out of their respective indentations (830) and expand the expandable distal portion (826) of the locking sheath (816), as depicted in FIG. 9E. Specifically, the expandable distal portion (826) may be positioned in the intermediate segment (818) of the lumen (812) when it is expanded.

When expanded, the expandable distal portion (826) may be configured to resist being removed from the lumen (912) of the barrel portion (910) of the grasper (900). Specifically, the expandable distal portion (826) of the locking sheath (816) may be sized and configured such that, when expanded, the expandable distal portion (826) may be prevented from passing through the proximal segment (914) of the lumen (912) (e.g., the outer diameter of the expanded distal portion (826) may be larger than the diameter of the proximal segment (914) of the lumen (912)). When the expandable distal portion (826) of the locking sheath (816) is expanded in the intermediate segment (918) (as shown in FIG. 9E), the locking sheath (816) may resist both advancement of the locking sheath (816) into the distal segment (916) (as discussed above) and withdrawal of the locking sheath (816) though the proximal segment (914) of the lumen (912). Accordingly, the expanded locking sheath (816) may lock the grasper (900) in place relative to the delivery device (800).

When the actuation rod (814) is further advanced to actuate the jaws (902, 904) of the grasper (900) (as shown in FIG. 9F, and discussed in more detail below), the actuation rod (814) may apply one or more forces to the grasper (900) which may have a tendency to push the grasper (900) away from the coupling magnet (818) (which in some instances could possibly inadvertently decouple the grasper (900) from the delivery device (800)), but the engagement between the expanded locking sheath (816) and the grasper (900) may overcome these forces to maintain the position of the grasper (900) relative to the delivery device (800).

To disengage the locking sheath (816) from the grasper (900), the actuation rod (814) may be retracted until the indentations (830) of the actuation rod (814) reach the internal projections (828) of the locking sheath (816). The expandable distal portion (826) of the locking sheath (816) may be biased toward an unexpanded state such that the internal projections (828) reposition themselves into their respective indentations (830), as shown in FIG. 9D. The actuation rod (814) may then be withdrawn to withdraw the locking sheath (816) (e.g., by virtue of the connection between the indentations (830) and the internal projections (828)).

The grasper (900) may be configured to be actuated in any suitable manner. In some variations, the grasper (900) may be configured such that it may be actuated by a force applied internally of the grasper (900) (e.g., via an actuation rod (814) of the delivery device (800) advanced through the lumen (912) of the barrel portion (910) of the grasper (900), as discussed in more detail below), and may be further configured such that it may be actuated by a force applied externally of a grasper (900) (e.g., via a grasping device). For example, in the variation of the grasper (900) shown in FIGS. 9A-9F, the grasper (900) may comprise a proximal arm (920) connected to the first jaw (902), wherein rotation of the proximal arm (920) rotates the first jaw (902) relative to the main body (906) and second jaw (904) of the grasper (900). The proximal arm (920) may act as a lever and/or a cam to rotate the first jaw (902).

For example, in some instances the proximal arm (920) may act as a cam to rotate the first jaw (902). In these instances, the actuation rod (814) of the delivery device (800) may rotate the first jaw (902). Specifically, a portion of the proximal arm (920) may be aligned relative to the lumen (912) such that advancement of the actuation rod (814) through the lumen (912) pushes the actuation rod (814) into contact with the proximal arm (920), as illustrated in FIG. 9E. Once in contact with the proximal arm (920), advancement of the actuation rod (814) may push against the proximal arm (920). The proximal arm (920) may act as a cam to convert the linear motion of the actuation rod (814) into rotation of the proximal arm (920), which may in turn rotate the first jaw (902) away from the second jaw (904) as shown in FIG. 9F. When the first jaw (902) is spring-biased toward the second jaw (904), the rotation of the proximal arm (920) may overcome this spring bias, which may allow the actuation rod (814) to hold the first jaw (902) in its open position. Additionally, the first jaw (902) may rotate back toward the second jaw (904) when the actuation rod (814) is retracted.

Additionally, in the variation of the grasper (900) shown in FIGS. 9A-9F, at least a portion of the proximal arm (920) may be exposed relative to the main body (906), which may allow a grasping device to grasp the proximal arm (920) to rotate the first jaw (902) relative to the second jaw (904). For example, opposing forces (represented by arrows (922) in FIG. 9A) may be applied (e.g., via a grasping device) to the exposed portion of the proximal arm (920) and the main body (906) to cause the proximal arm (920) to rotate around the pivot point (908) (which may in turn rotate the first jaw (902) away from the second jaw (904)).

While the proximal arm (920) is shown in FIGS. 9A-9F as being curved, it should be appreciated that in some variations the graspers described here may also comprise one or more straight segments. The actuation rod (814) may be advanced and withdrawn in any suitable manner. For example, when the delivery device (800) comprises an actuation control mechanism, such as a slider, knob, trigger, or the like, the actuation control mechanism may be operatively connected to the actuation rod (814) such that the actuation control mechanism may advance and withdraw the actuation rod (814). For example, in the variation of the delivery device (800) shown in FIGS. 8A-8C, the trigger (812) may be configured to advance and retract the actuation rod (814). In some of these variations, the trigger (812) may be configured such that rotation of the trigger (812) toward the grip portion (810) withdraws the actuation rod (814) relative to the shaft (806), while rotation of the trigger (812) away from the grip portion (810) advances the actuation rod (805) relative to the shaft.

In these variations, when the trigger (810) is in the first position (as shown in FIG. 8A), the actuation rod (814) may be positioned as shown in FIGS. 9A and 9B with the coupling magnet (818) in an advanced position, which may allow the distal engagement portion (808) to connect to a grasper (such as grasper (900), as illustrated in FIGS. 8A and 9B). The trigger (812) may be rotated toward the grip portion (810) to position the trigger (812) in the third position (as shown in FIG. 8C), and this rotation may retract the actuation rod (814) relative to the shaft (806). Retraction of the actuation rod (814) may also withdraw the coupling magnet (818) to a retracted position, such as illustrated in FIG. 9C, which may decouple a grasper from the delivery device (800) as described above. The trigger (812) may be rotated away from the grip portion (810) and back to the first position to advance the actuation rod (814) back to the position shown in FIGS. 9A and 9B.

Further rotation of the trigger (812) away from the grip portion (810) may move the trigger (812) from the first position to the second position (as shown in FIG. 8B) and may advance the actuation rod (814) through a lumen of a barrel portion of a grasper (e.g., the lumen (912) of the barrel portion (910) of the grasper (900) described above) to rotate one or more jaws of the grasper (as shown in FIG. 9F). Returning the trigger (812) to the first position (e.g., by rotating the trigger (812) toward the grip portion (810)) may withdraw the actuation rod (814) relative to the shaft (806) and the grasper, which may allow the grasper to return to a closed configuration. It should be appreciated that in some variations, rotation of the trigger (812) toward the grip portion (810) may be configured to advance the actuation rod (814) relative to the shaft (806), while rotation of the trigger (812) away from the grip portion (810) may retract the actuation rod (814) relative to the shaft (806).

Figures 11A, 11B, 11C:
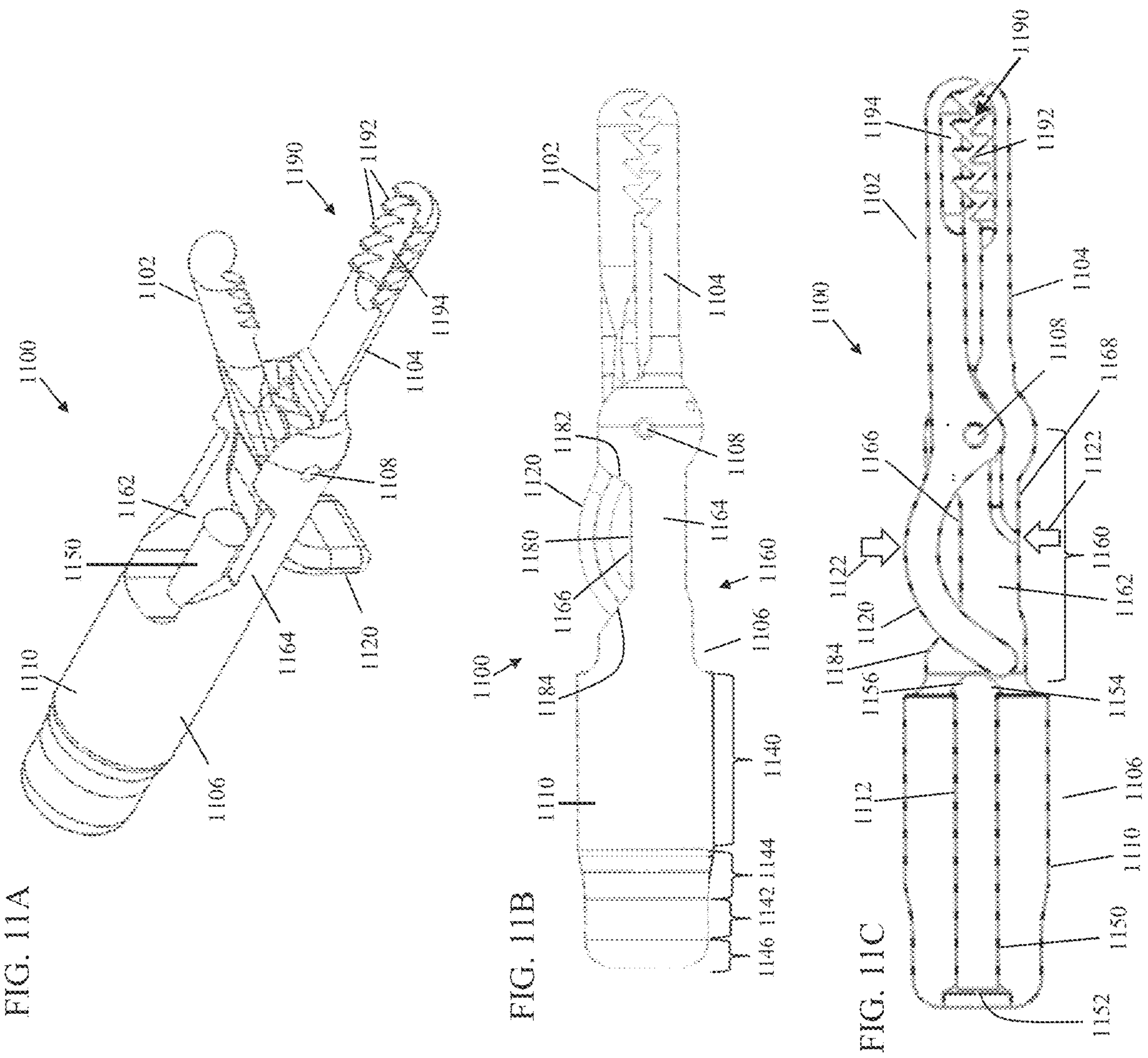
FIGS. 11A and 11B show perspective and side views, respectively, of an illustrative variation of a grasper as described here.
FIG. 11C shows a cross-sectional side view of the grasper of FIGS. 11A and 11B.

FIGS. 11A-11C depict another variation of a grasper (1100) as described here. Specifically, FIGS. 11A and 11B show perspective and side views, respectively, of the grasper (1100). As shown there, the grasper (1100) may comprise a first jaw (1102), a second jaw (1104), and a main body (1106). Generally, the first jaw (1102) may be rotatably connected to the main body (1106) at a pivot point (1108), such that the first jaw (1102) may rotate relative to the main body (1106). While the second jaw (1104) is shown in FIGS. 11A-11C as being fixed relative to the main body (1106), it should be appreciated that in some variations the second jaw (1104) may be rotatably connected to the main body (1106), such as discussed in more detail above. The first jaw (1102) (and/or the second jaw (1104) in variations where the second jaw (1104) is rotatably connected to the main body (1106)) may be rotated relative to the main body (1106) to actuate the grasper (1100) between an open configuration and a closed configuration.

Specifically, in the open configuration, the first jaw (1102) and the second jaw (1104) may be held in rotationally separated positions to define a space between the first jaw (1102) and the second jaw (1104), as shown in FIG. 11A. In the closed configuration, the first jaw (1102) and second jaw (1104) may be rotationally biased toward each other, as shown in FIG. 11B. While the first jaw (1102) is shown as contacting the second jaw (1104) in FIG. 11B, it should be appreciated that when the grasper (1100) is connected to tissue, tissue positioned between the first jaw (1102) and the second jaw (1104) may prevent the first jaw (1102) from contacting the second jaw (1104) when the grasper is in the closed configuration. The first jaw (1102) and second jaw (1104) may be rotationally biased toward a closed configuration in any suitable manner (e.g., via a torsional spring (not shown)), such as described in more detail above.

The main body (1106) of the grasper (1100) may comprise a barrel portion (1110) with a lumen (1112) extending therethrough. A portion of a delivery device may be advanced at least partially into the lumen (1112) to actuate the grasper (1100) between closed and an open configurations, as will be discussed in more detail below. The outer diameter of the barrel portion (1110) may be uniform, or may vary along the length of the barrel portion (1110). For example, in the variation of the grasper (1100) shown in FIGS. 11A-11C, the barrel portion (1110) may have a first segment (1140) having a first outer diameter and a second segment (1142) having a second outer diameter. In some variations, the first outer diameter may be greater than the second outer diameter, which may allow the first segment (1140) to act as a stop when engaged by a delivery device, such as discussed in more detail herein. For example, in some variations the first segment may have a first outer diameter of about 10 mm, and the second segment may have an outer diameter between about 7 mm and about 9 mm.

In some variations (such as the variation of grasper (1100) illustrated in FIGS. 11A-11C), the barrel portion (1110) may further comprise a tapered portion (1144) positioned between the first segment (1140) and the second segment (1142), such that the outer diameter of the tapered segment (1144) tapers between the first outer diameter and the second outer diameter. It should be appreciated, however, that the barrel portion (1110) need not have such a tapered portion (1144), and the first segment (1140) may immediately transition to the second segment (1142). In variations that do include a tapered segment (1144), the tapered segment (1144) may provide a gradual diameter transition between the first (1140) and second (1142) segments, which may in turn reduce the presence of edges that may catch on or otherwise disturb tissue during use of the grasper (1100).

Additionally or alternatively, the barrel portion (1110) may have a tapered segment (1146) at a proximal end of the barrel portion (1110), which may also be at a proximal end of the first segment (1140). In these variations, the diameter of the tapered segment (1146) may taper from the first outer diameter of the first segment (1140) to a third outer diameter smaller than that of the first outer diameter. In variations that include a tapered segment (1146) at a proximal end of the barrel portion (1110), the tapered diameter may facilitate alignment of the barrel portion (1110) with a portion of the delivery device. Specifically, when a proximal end of the barrel portion (1110) is inserted into a portion of a delivery device (as described in more detail below), the tapered segment (1146) may help guide the barrel portion (1110) into the delivery device, which may be beneficial in instances where the delivery device (or another retrieval device) is connected to the grasper to retrieve the grasper.

The first jaw (1102) may be configured to rotate in any suitable manner such as described above. For example, in the variation of the grasper (1100) shown in FIGS. 11A-11C, the grasper (1100) may comprise a proximal arm (1120) connected to the first jaw (1102) such that rotation of the proximal arm (1120) relative to the pivot point (1108) rotates the first jaw (1102) relative to the pivot point (1108) (which may also rotate the first jaw (1102) relative to the main body (1106) and/or the second jaw (1104)). While the proximal arm (1120) shown in FIGS. 11A-11C may comprise a curved arm (1120) that may be configured to act as both a cam and a lever (similar to the proximal arm (920) of the grasper (900) discussed above with respect to FIGS. 8A-8C and 9A-9F). The proximal arm (1120) (and/or an eccentric cam member) may assist in actuation of the grasper (1100), as described hereinthroughout.

Generally, at least a portion of the proximal arm (1120) may be exposed relative to the main body (1106), which may allow a grasping device to grasp the proximal arm (1120) to rotate the first jaw (1102) relative to the second jaw (1104), as will be discussed in more detail below. Specifically, the main body (1106) may comprise a barrel extension (1160) between the barrel portion (1110) and the pivot point (1108). As shown in a cross-sectional side view in FIG. 6C, the barrel extension (1160) may comprise a channel (1162) extending at least partially through the barrel extension (1160). In the variation shown in FIGS. 11A-11C, the channel (1162) may extend entirely through the barrel extension (1160). The barrel extension (1160) may have a wall (1164) on one or both sides of the channel (1162). In the variation shown in FIGS. 11A-11C, the barrel extension (1160) may have a wall (1164) on each side of the channel (1162). The proximal arm (1120) may be positioned at least partially within the channel (1162), and may be configured to rotate through the channel (1162) as the grasper (1100) is actuated between open and closed configurations.

Generally, each wall (1164) of the barrel extension (1160) may have a top edge (1166) and a bottom edge (1168). The top edge (1166) and bottom edge (1168) may have any suitable profile, and together may define a height of the wall (1164). For example, in the variation shown in FIGS. 11A-11C, the bottom edge (1168) may be linear and substantially parallel to a longitudinal axis, while the top edge (1166) may include a linear portion (1180) positioned between two ramped segments (labeled (1182) and (1184)). In these variations, the height of the walls (1164) may decrease along each of the ramped segments (1182) and (1184) toward the linear portion (1180). This may facilitate grasping of the grasper (1100) with a grasping device, as will be described in more detail below. In other variations, the top edge (1166) and/or the bottom edge (1168) may have a curved profile.

In some variations, the graspers described here may comprise a shuttle pin at least partially positioned in a lumen of the barrel portion of the grasper. Generally, the shuttle pin may reduce the distance an actuation rod may need to be inserted into the barrel portion in order to actuate the grasper. For example, in the variation of the grasper (1100) shown in FIG. 11C, the grasper (1100) may further comprise a shuttle pin (1150). The shuttle pin (1150) may be positioned at least partially within the lumen (1112) of the barrel portion (1110) of the grasper (1100) and may be configured to slide relative to the lumen (1112). The shuttle pin (1150) may have a proximal end (1152) and a distal end (1154), and may assist in actuation of the grasper (1100). Specifically, advancement of a portion of a delivery device (e.g., an actuation rod) into the lumen (1112) of the barrel portion (1110) may cause the delivery device to contact the proximal end (1152) of the shuttle pin (1150) and advance the shuttle pin (1150) relative to the lumen (1112). As the shuttle pin (1150) is advanced relative to the lumen (1112) of the barrel portion (1110), the distal end (1154) of the shuttle pin (1150) may press against the proximal arm (1120) (or an eccentric cam member, in variations where the grasper includes an eccentric cam member), which may cause the proximal arm (1120) to act as a cam member, such as discussed in more detail above.

Without the shuttle pin (1150), an actuation rod may otherwise need to be inserted into the barrel portion (1110) until it contacts the proximal arm (1120) directly, such as discussed above. When the delivery device is withdrawn relative to the shuttle pin (1150), the return bias of the first jaw (902) toward a closed configuration may push the shuttle pin (1150) proximally relative to the lumen (1112) of the barrel portion (1110). While the variations of the graspers discussed above with respect to FIGS. 9A-9F are not depicted as having a shuttle pin, it should be appreciated that any of these graspers may comprise a shuttle pin, which may be configured in any suitable manner as discussed with respect to shuttle pin (1150) of the grasper (1100) shown in FIGS. 11A-11C.

In variations where the graspers described here comprise a shuttle pin, the grasper may be configured to help prevent the shuttle pin from disengaging from the grasper. In some variations, at least a portion of a shuttle pin may be configured to have an outer profile that is larger than at least a portion of the lumen of the barrel portion of a main body. For example, in the variation of the shuttle pin (1150) shown in FIG. 11C, the distal end (1154) may comprise a cap (1156) that may have an outer diameter sized to be larger than the lumen (1112) of the barrel portion (1110) of the main body (1106). The shuttle pin (1150) may be positioned in the lumen (1112) such that the cap (1156) is positioned distally of the lumen (1112). Because the cap (1156) is sized larger than the lumen (1112), it may be prevented from entering the lumen (1112) as the shuttle pin (1150) is slid proximally relative to the barrel portion (1110). Accordingly, the shuttle pin (1150) may slide proximally until the cap (1156) contacts the barrel portion (1110), at which point the cap (1156) may act as a stop to prevent further proximal movement of the shuttle pin (1150). This may prevent the shuttle pin (1150) from sliding out of the proximal end of the barrel portion (1110) and disengaging the grasper (1100).

Additionally, the grasper (1100) may be configured to limit the amount of distal advancement of the shuttle pin (1150). Generally, a portion of a proximal arm or an eccentric cam member (e.g., the proximal arm (1120) of grasper (1100)) may be aligned with the lumen of the barrel portion, which may resist or stop forward advancement of the shuttle pin (1150) due to gravitational forces. When a delivery device or other device is used to advance the shuttle pin (1150) to rotate the proximal arm and/or eccentric cam member, the delivery device and/or grasper may be configured to limit advancement of the shuttle pin (e.g., by blocking advancement of the shuttle pin (1150) when the grasper is opened, as discussed in more detail below).

In some of these variations, when a delivery device is used to advance the shuttle pin (1150), it may be configured to advance the shuttle pin a predetermined distance (e.g., about 1 cm, about 1.25 cm, about 2 cm, or the like) to actuate the grasper (1100). In these variations, the shuttle pin (1150) may be sized to be longer than this predetermined distance (e.g., greater than about 2.5 cm, greater than about 3 cm, or the like), such that at least a portion of the shuttle pin (1150) may remain in the lumen when fully advanced by the delivery device. In some of these variations, the shuttle pin may be sized with a length such that at least a predetermined length (e.g., about 1.25 cm) of the shuttle pin remains in the lumen (1112) when the shuttle pin (1150) has been advanced the predetermined distance (e.g., for an advancement distance of about 1.25 cm, the shuttle pin may have a length of about 2.5 cm).

Additionally or alternatively, the grasper (1100) may be configured to limit the amount that the delivery device may advance the shuttle pin (1150). For example, in some variations, a portion of the grasper (1100) may be positioned in the path of the shuttle pin (1150) and resists further advancement of the shuttle pin (1150) by the delivery device. For example, the pivot point (1108) may be positioned along the movement path of the shuttle pin (1150). In these variations, the distal end (1154) of the shuttle pin (1150) may be stopped from further advancement by a portion of the first jaw (1102) and/or the proximal arm (1120) (and/or the eccentric cam member, in variations where the grasper contains an eccentric cam member) near the pivot point (1108).

The grasper (1100) shown in FIGS. 11A-11C may be actuated in any suitable manner. In some variations, the grasper (1100) may be configured such that it may be actuated by a force applied internally of the grasper (1100) (e.g., via an actuation rod of a delivery device advanced through the lumen (1112) of the barrel portion (1110) of the grasper (1100), as discussed in more detail below), and may be further configured such that it may be actuated by a force applied externally of a grasper (1100) (e.g., via a grasping device).

FIGS. 12A-12D depict cross-sectional side views of a distal portion of a delivery device (1200) and a manner of actuating the grasper (1100) using the delivery device (1200). The delivery device (1200) and grasper (1100) may be configured for minimally invasive introduction into the body, such as described above. Specifically, the delivery device (1200) may comprise a handle (not shown), a shaft (1206) extending from the handle, and a distal engagement portion (1208) at a distal end of the shaft (1206). The handle may comprise an actuation control mechanism that may be manipulated by a user to controllably actuate the grasper, and may be configured as described above with respect to the handle (804) of the delivery device (800) described above with respect to FIGS. 8A-8C. In some of these variations, the actuation control mechanism may comprise a trigger.

In some of these variations, the actuation control mechanism may be configured to both actuate the grasper (1100) and the delivery device (1200). In variations where the actuation control mechanism comprises a trigger, the trigger may be moveable between three positions (although it should be appreciated that the trigger may assume one or more intermediate positions between these positions). Of the three positions, the trigger may be moveable between a first position (such as the position of the trigger (812) of the delivery device (800) shown in FIG. 8A) and a second position (such as the position of the trigger (812) of the delivery device (800) as shown in FIG. 8B) to close and open, respectively, the grasper (1100). The trigger may be moveable to a third position (such as the position of the trigger (812) of the delivery device (800) as shown in FIG. 8C) to eject or otherwise release the grasper (1100) from the delivery device (1200). In some of these variations, to move the trigger from the second position (in which the grasper (1100) is placed in an open configuration) to the third position (to eject the grasper (1100) from the delivery device (1200)), the trigger may need to be moved through the first position, thereby moving the grasper (1100) to a closed configuration prior to ejecting the grasper (1100).

Figures 12C, 12D:
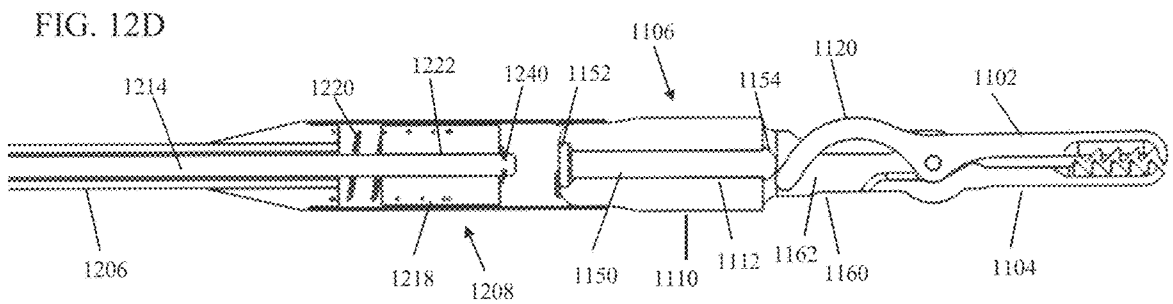

Returning to FIGS. 12A-12D, in some variations the distal engagement portion (1208) of the delivery device (1200) may comprise a coupling magnet (1218) and a spring (1220). In these variations, the coupling magnet (1218) may be slidably housed in the distal engagement portion (1208) (e.g., in a housing of the distal engagement portion (1208)). The coupling magnet (1218) may be moveable between an advanced position (as depicted in FIGS. 12A-12C) and a retracted position (as depicted in FIG. 12D). The spring (1220) may be positioned within the distal engagement portion (1208) such that the spring (1220) biases the coupling magnet (1218) toward the advanced position. The delivery device (1200) may be configured to couple to the grasper (1100) when the coupling magnet (1218) is in the advanced position.

As described in more detail herein, at least a portion of the grasper (1100) may comprise one or more materials configured to be attracted by a magnetic field. When the grasper (1100) is positioned near the distal engagement portion (1208) (such as shown in FIG. 12A), the coupling magnet (1218) may attract the grasper (1100) and temporarily couple the grasper (1100) to the delivery device (1200).

Specifically, when the grasper (1100) is temporarily coupled to the delivery device (1200), at least a portion of the barrel portion (1110) may be positioned within the distal engagement portion (1208), as shown in FIG. 12B. The attractive force between the coupling magnet (1218) and the grasper (1100) may hold the grasper (1100) in place. In variations where the grasper (1100) has a barrel portion (1110) having a first segment (1140) having a first outer diameter and a second segment (1142) having a second outer diameter (e.g., FIG. 11B), the second outer diameter may be sized to fit within the distal engagement portion (1208) while the first outer diameter may be sized such that it is too large to fit within the distal engagement portion (1208). In these variations, the first segment (1140) (or a tapered segment (1144) between the first segment (1140) and the second segment (1142)) may act as a stop to limit the amount of the barrel portion (1110) that may enter the distal engagement portion (1208).

It should be appreciated that in some variations the proximal end of the grasper may comprise a magnetic element used with a control element to maneuver the grasper. In these variations, the magnetic element in the proximal end of the grasper may also be used to attract the distal engagement portion of the delivery device and couple the grasper and the delivery device. Additionally, the delivery device may comprise a coupling magnet, but need not. When the delivery device does not comprise a coupling magnet, a distal engagement portion of the delivery device may comprise a coupling element comprising a ferromagnetic or ferrimagnetic material that is slidably housed in the distal engagement portion. The coupling element may be configured to move between an advanced position and a retracted position, where the delivery device is configured to couple to the grasper via attractive force between the magnetic element in the grasper and the coupling element when the coupling element is in the advanced position.

In order to decouple the grasper (1100) from the distal engagement portion (1208), the coupling magnet (1218) may be withdrawn to the retracted position, such as shown in FIG. 12D. As the coupling magnet (1218) is retracted, the attractive force between the coupling magnet (1218) and the grasper (1100) may move the grasper (1100) proximally relative to the distal engagement portion (1208). The first segment (1140) (or the tapered segment (1144)) may limit the movement of the grasper (1100) into the distal engagement portion (1208), such that the distance between the coupling magnet (1218) and the grasper (1100) increases. This may decrease the attractive force between the coupling magnet (1218) and the grasper (1100), which may allow the grasper (1100) to be pulled from, released from, or otherwise fall from the distal engagement portion (1208).

The coupling magnet (1218) may be retracted in any suitable manner, such as described in more detail above. For example, in the variation of the delivery device (1200) shown in FIGS. 12A-12D, the delivery device (1200) may comprise an actuation rod (1214) slidably disposed in the shaft (1206). The actuation rod (1214) may be configured to retract the coupling magnet (1218). For example, the actuation rod (1214) may be slidably disposed within a lumen (1222) of the coupling magnet (1218). In some variations, at least a segment of the actuation rod (1214) may be sized and configured such that the portion of the actuation rod (1214) cannot fully pass through the lumen (1222). For example, the variations in FIGS. 12A-12D show a segment (1240) of the actuation rod that may have a diameter greater than a diameter of the lumen (1222).

Additionally or alternatively, the segment (1240) may comprise one or more projections extending from an outer surface of the actuation rod (1214) and which cannot fully pass through the lumen (1222). When the segment (1240) of the actuation rod (1214) is positioned distal to the coupling magnet (1218), the actuation rod (1214) may be freely advanced relative to the coupling magnet (1218). Conversely, withdrawal of the actuation rod (1214) may pull the segment (1240) of the actuation rod (1214) into contact with the coupling magnet (1218). Since the segment (1240) cannot fully pass through the lumen (1222) of the coupling magnet (1218), further withdrawal of the actuation rod (1214) may cause the segment of the actuation rod (1214) to pull on and withdraw the coupling magnet (1218). When the actuation rod (1214) is subsequently advanced, the spring (1220) may advance the coupling magnet (1218) with the actuation rod (1214) until the coupling magnet (1218) reaches the advanced position.

The actuation rod (1214) may be advanced or retracted relative to the shaft (1206) to actuate and/or eject the grasper (1100). In variations where the handle comprises a trigger (such as discussed above), the trigger may be operatively connected to the actuation rod (1214), such that movement of the trigger slides the actuation rod (1214). Movement of the actuation rod (1214) may rotate the first jaw (1102) of the grasper (1100). Specifically, when the grasper (1100) is coupled to the delivery device (1200) (as shown in FIG. 12B), the actuation rod (1214) may be aligned with the lumen (1112) of the barrel portion (1110) such that the actuation rod (1214) enters the lumen (1112). As the actuation rod (1214) is advanced into the lumen (1112), the actuation rod (1214) may press against the proximal end (1152) of the shuttle pin (1150) and advance the shuttle pin (1150) along the lumen (1112). As the shuttle pin (1150) is advanced along the lumen (1112), the distal end (1154) of the shuttle pin (1150) may move into the channel (1162) of the barrel extension (1160). The distal end of the shuttle pin (1150) may in turn push against the proximal arm (1120) (e.g., against a portion of the proximal arm (1120) that is positioned in the channel (1162) and aligned with the lumen (1112)). The proximal arm (1120) may act as a cam to convert the linear motion of the shuttle pin (1150) into rotation of the proximal arm (1120), which may in turn rotate the first jaw (1102) away from the second jaw (1104). When the first jaw (1102) is spring-biased toward the second jaw (1104), the rotation of the proximal arm (1120) may overcome this spring bias, which may allow the actuation rod (1214) to hold the first jaw (1102) in its open position, as shown in FIG. 12C.

Additionally, the first jaw (1102) may rotate back toward the second jaw (1104) when the actuation rod (1214) is retracted. Specifically, as the actuation rod (1214) is withdrawn, the return bias of the first jaw (1102) may cause the proximal arm (1120) to push against the shuttle pin (1150), which may slide the shuttle pin (1150) proximally within the lumen (1112). This may return the grasper (1100) to a closed configuration, such as shown in FIG. 12B. When the grasper (1100) is closed around tissue, the actuation rod (1214) may be further retracted to release the grasper (1100) from the delivery device (1200), as discussed above. When a trigger is moveable between three positions to actuate and release the grasper (1100) as discussed above, placing the trigger in the first position may position the actuation rod (1214) in a position as illustrated in FIG. 12B, in which the grasper (1100) may be coupled to the delivery device (1200) in a closed configuration. Moving the trigger to the second position may advance the actuation rod to the position illustrated in FIG. 12C, in which the grasper (1100) may be releasably coupled to the delivery device (1200) in an open configuration. Moving the trigger to the third position may retract the actuation rod (1214) to the position illustrated in FIG. 12D, in which the grasper (1100) may be decoupled from the delivery device (1200).

Additionally, in the variation of the grasper (1100) shown in FIGS. 11A-11C, at least a portion of the proximal arm (1120) may be exposed relative to the main body (1106) (e.g., at least a portion of the proximal arm (1120) may extend out of the channel (1162) of the barrel extension (1160)), which may allow a grasping device to grasp the proximal arm (1120) to rotate the first jaw (1102) relative to the second jaw (1104). For example, opposing forces (represented by arrows (1122) in FIG. 11C) may be applied (e.g., via a grasping device) to the exposed portion of the proximal arm (1120) and the main body (1106) (e.g., the barrel extension (1160)) to cause the proximal arm (1120) to rotate around the pivot point (1108) (which may, in turn rotate the first jaw (1102) away from the second jaw (1104)). In these variations, the height of the walls (1164) of the barrel extension (1160) may limit the amount that the proximal arm (1120) may be rotated (e.g., a grasping device may rotate the proximal arm (1120) until the grasping device contacts the top and bottom edges of the wall).

Additionally or alternatively, when the top and/or bottom edges of a wall of the barrel portion are curved or ramped, the curved or ramped edges may help guide a grasping device toward another section of the barrel extension (1160) during grasping. Specifically, if the grasping device applies a compressive force at a ramped or curved portion of an edge, the grasping device may slide along the ramped/curved portion toward a shorter portion of the wall. For example, in the variation of the grasper (1100) shown in FIGS. 11A-11C, if a grasping device applies a compressive force at either the ramped segments (1182) or (1184) of the top edge (1166), the grasping device may slide toward the linear portion (1180).

2. Grasper

As mentioned above, the graspers described herein may comprise a first jaw and a second jaw, and at least one of the first jaw and the second jaw may be configured to rotate relative to the grasper to actuate the grasper between an open configuration and a closed configuration. The jaws may be configured in the closed configuration to secure tissue. In some variations, the graspers may be configured to secure tissue by engaging the tissue between a grasping surface of each of the two jaws (e.g., gripping, squeezing, compressing, etc. the tissue between the two jaws). That is, the jaws may be configured to hold tissue between two surfaces that would be in contact in the closed configuration but for the tissue between the surfaces. In these variations, the jaws of the graspers may comprise one or more features which may promote engagement with tissue. In some variations, one or more surfaces of a jaw may be roughened, which may help to reduce slipping between the jaws and tissues.

Additionally or alternatively, the graspers may comprise teeth or other projections which may facilitate engagement of the jaw with tissue. For example, in the variation of the grasper (1100) shown in FIGS. 11A-11C, the first jaw (1102) and the second jaw (1104) may each include a grasping surface (1190) having a plurality of teeth (1192). In a closed configuration, the grasper (1100) may be configured to engage tissue between the teeth (1192) of the grasping surfaces (1190). In variations in which the grasper (1100) is biased toward the closed configuration, the combination of the size, shape, and features (e.g., teeth) of the grasper (1100), as well as the biasing force (e.g., due to a torsional or cantilever spring), may be chosen to produce a desired grasping force on the tissue. It may in some instances be desirable for the grasping force to allow the delivery device to be decoupled from the grasper (1100) and to allow the tissue to be held securely during a procedure, while not causing tissue damage.

In some variations, one or more jaws of the graspers described here may include a longitudinal recess extending at least partially through the jaws. With reference to FIG. 11C for example, grasper (1100) may include a recess (1194) extending at least partially through the grasping surface (1190) and some of the teeth (1192). Similarly, graspers (1300), (1400), and (1500) may include recesses (1394), (1494), and (1594), respectively, extending at least partially through each of first and second jaws (1302, 1304), (1402, 1404) and (1502, 1504), respectively. In these variations, when the jaws are used to grasp tissue therebetween, tissue may be squeezed or captured into or otherwise enter the recess of each jaw, which may help to provide a more secure hold between the grasper and the tissue. The size and placement of the recesses may also influence the effect of a magnetic field on the graspers, as described in more detail below.

In some variations of the graspers described here, the grasper may comprise one or more coatings which may help to smooth discontinuities in the contours of the grasper and may act to provide one or more atraumatic surfaces of the grasper. The one or more coatings may comprise silicone, urethane, one or more nylon blends, polyethylenes, fluoropolymers, combinations thereof and the like. It may also be desirable to use certain coatings and/or materials in or on all or a portion of the grasper in order to reduce the occurrence of unintended electrical current flowing through the grasper. For example, in a surgical procedure involving electrical current (e.g., electrocautery), if the grasper contacts an electrocautery instrument, the electrical current may flow through the grasper and cause cauterization of, or burns in, the various tissues touching the grasper. This cauterization or burning of the tissue may be unintended and/or undesirable. Thus, non-conducting materials and/or coatings may be used on all or a portion of the grasper (e.g., a portion of the grasper closest to the surgical site) to reduce or eliminate the flow of electrical current through the grasper and thus reduce the likelihood that tissue may be damaged unintentionally by electrical current. For example, and as described in more detail below, in some variations, one of the jaws of a grasper (such as any of the graspers described herein) may be made of non-conducting material. Additionally or alternatively, the distal portion of one or both of the jaws of a grasper (such as any of the graspers described here) may be made of a non-conducting material. Any suitable non-conductive material (e.g., plastic, or the like) and/or non-conductive coating (e.g., paints, plastic tubing, co-molded thermoplastic elastomers, a combination thereof, or the like) may be used. In some instances, materials used for non-conductive properties may be the same as those used for non-magnetic properties (e.g., plastic), which are described in more detail below.

B. Maneuvering the Grasper

As mentioned above, the graspers described here may be used to provide remote manipulation of tissue during a minimally-invasive procedure. During such a procedure, it may be desirable to maneuver and/or control the grasper using one or more elements located outside of the body (e.g., one or more control elements), so that the delivery devices described here may be withdrawn, and the access ports may be utilized for other tools and/or instruments. It may also be desirable to maneuver another tool using one or more elements located outside of the body (e.g., one or more control elements), so that the position and/or orientation of the tool can be controlled without occupying an access port.

Maneuvering and/or controlling the grasper using one or more elements located outside the body, and not through a physical connection via an access port, may additionally or alternatively allow for force to be applied to the grasper (and in turn to tissue) in a direction different from the direction of force that may be applied through an access port. This may allow force to be applied to the grasper (and in turn to tissue) in a greater number of directions. Additionally or alternatively, maneuvering and/or controlling the grasper using one or more elements located outside the body, and not through a physical connection via an access port, may allow for improved visualization of a region of interest. In some variations, it may be desirable to control an orientation of the grasper using one or more elements located outside of the body (e.g., one or more control elements) to increase maneuverability and control of the grasper.

Generally, the graspers may be maneuvered using one or more attractive and/or repulsive forces. Specifically, the graspers may be configured to be attracted to and/or repelled by one or more magnetic elements positioned externally of the body. Attractive and/or repulsive forces originating from outside the body may be used to move, reposition, and/or hold the grasper. These forces may in turn move, hold, and/or provide traction for the tissue held by the grasper. In some instances, it may be desirable to configure the grasper and the control element such that their magnetic attributes and/or those of the control element do not affect other instruments that are not intended to be part of the magnetically controlled grasping system described herein.

The graspers described here may generally comprise a combination of materials having different magnetic behavior. Varying the type of materials in the grasper, where they are located in and/or on the grasper, and the configuration of those materials, may serve several purposes. Generally, the arrangement of non-magnetic, ferromagnetic, ferrimagnetic, and/or diamagnetic materials within an instrument may alter the behavior of the instrument when it is exposed to a magnetic field. The use of a combination of these materials may provide increased control over the movements of the grasper and the tissue held within its jaws, as compared to a grasper made from only one type of material. The configuration of the materials within the grasper—for example, the type, amount, polarity, and location of the materials—may alter how the grasper responds to and/or interacts with a control element.

For example, using both magnetic and non-magnetic materials may affect which portions of the grasper are attracted to, unaffected by, or repelled by magnetic fields generated by the control element (and may affect which portions of the grasper may create magnetic fields that may attract, not affect, or repel portions of the control element).

As another example, increasing the amount of magnetic material located in a specific portion of the grasper may increase the attractive or repulsive force between that portion of the grasper and a control element. Similarly, removing magnetic material from a specific portion of the grasper and replacing it with a non-magnetic material may decrease the attractive or repulsive force between that portion of the grasper and the control element. Varying the type of materials and where they are located may also modify the distribution of the mass of the grasper, which may contribute to a user's ability to control and maneuver the grasper. As mentioned above, this may provide for better control over the grasper and the tissue within its jaws, as described in more detail below.

As another example, the response of a grasper to an applied magnetic field may also be altered by removing material entirely to leave an air gap (in instances where the material is not required for the grasper to hold tissue as desired). With reference to FIG. 11C for example, grasper (1100) may include a recess (1194) extending at least partially through the grasping surface (1190) and some of the teeth (1192) of the first jaw (1102). In variations in which the jaws (1102, 1104) comprise a material attracted to a magnetic field, when a magnetic field is applied to grasper (1100), a greater force may be generated on the second jaw (1104) than the first jaw (1102), since the second jaw (1104) comprises more material. As a result, when the grasper (1100) is located in an abdominal cavity and controlled by a magnetic field from an external control element, the grasper (1100) may have an increased tendency to lie parallel to the cavity wall with the second jaw (1104) against the cavity wall.

Additionally or alternatively, employing both magnetic and non-magnetic materials may allow for control over the grasper from outside the body while decreasing the likelihood that other surgical instruments will be attracted to and/or will stick to the grasper. These other instruments, when attracted to and/or stuck on the grasper, may interfere with the ability to execute fine motions that may be required during a surgical procedure, and may cause delays during surgical procedures caused by the need to separate surgical instruments that may have been inadvertently attracted to and/or become stuck on the grasper. To reduce these undesired effects, parts of the grasper may for example be composed of non-magnetic materials (e.g., 300-series stainless steel, plastic, or the like) and/or be coated with a non-magnetic coating, including but not limited to, non-magnetic paints, plastic tubing, co-molded thermoplastic elastomers, a combination thereof, and the like. These non-magnetic materials and/or coatings may reduce or eliminate the attraction between the grasper and other instruments, while maintaining the ability to control the grasper from outside the body.

For example, in some variations a portion of the grasper may be made from plastic (e.g., both jaws, one jaw, a distal portion of one or both jaws, a proximal portion of one or both jaws, a combination thereof, or the like) while the remainder of the grasper may comprise a ferromagnetic material. In these variations, the plastic portion of the grasper will not attract surgical tools, but the grasper may still be controlled using an external control element.

In variations in which a non-magnetic coating may be applied to a magnetic material, the coating may increase the distance between the magnetic material and the surgical instruments, and may prevent close contact between the magnetic material and the instruments. This may decrease the attractive force between the coated portion of the grasper and the surgical instruments, but may still allow the grasper to be controlled by an external control element. In some instances, it may be desirable to use non-magnetic materials and/or coatings on the portion of the grasper closest to the surgical site (e.g., all or a portion of the jaws, such as a proximal portion); however, such materials and/or coatings may be utilized at any location on the grasper that does not interfere with the control of the grasper or the coupling of the delivery devices using a coupling magnet, as described above. Generally, thicker coatings will decrease the force between the grasper and the other instruments, and coatings of any suitable thickness may be used to achieve a desired force profile. In some variations, it may also be possible to use diamagnetic materials and/or coatings to reduce the likelihood that other surgical instruments will be attracted to and/or will stick to the grasper.

The control elements described here may optionally comprise a combination of magnetic and non-magnetic materials. The configuration of the magnetic and non-magnetic materials within the control element, for example, the size, type, quantity, polarity, and location of the materials, may alter the behavior of the grasper. The control elements described here may also have a surface that, in use, may be placed on or near an external surface of a patient's abdominal cavity and that may be parallel to the external surface of the patient's abdominal cavity. The grasper and the control element may be configured to yield a desired grasper position and/or movement within the body. For example, in some variations, the control element and the grasper may be configured to rotate, move, and/or hold the grasper such that it is in a perpendicular configuration relative to the internal wall of the patient's abdominal cavity or the surface of the control element, i.e., with its longitudinal axis transverse to, and in some instances, substantially perpendicular to, the surface of the cavity wall or of the control element.

In other variations, the control element and the grasper may be configured to rotate, move, and/or hold the grasper in a parallel configuration, i.e., in a configuration in which its longitudinal axis extends in the same direction as, or in some instances, is substantially parallel to, the surface of the cavity wall or of the control element. In some instances, the control element and the grasper may be configured to rotate, move, and/or hold the grasper such that its longitudinal axis forms an angle between about 5 and about 85 degrees with the surface of the cavity wall or of the control element. In some instances, the control element and the grasper may be configured to move the jaws of the grasper while maintaining the positioning of the proximal end of the grasper.

As mentioned above, the graspers and control elements described here comprise magnetic elements. Generally, at least one of the elements in either the grasper or the control element comprises a permanent magnet, an electromagnet, or an electro-permanent magnet. The remaining magnetic elements in the graspers and control elements may comprise permanent magnets, electromagnets, or electro-permanent magnets, and/or may comprise other materials that are attracted to, and/or repelled by a magnetic field, including, but not limited to ferromagnetic materials, ferrimagnetic materials, diamagnetic materials, a combination thereof, and the like. In some variations both the grasper and the control element may comprise one or more permanent magnets. For example, they may both comprise permanent magnets oriented such that the dissimilar poles of the magnets attract each other when the grasper and control element are in the desired configurations. However, the grasper and control element need not both comprise permanent magnets. For example, in some variations, the grasper may comprise a magnetic element comprising a ferromagnetic or ferrimagnetic material (e.g., iron, cobalt, nickel, and the like) that is attracted to a magnetic field but does not independently generate a magnetic field, and the control element may comprise a magnetic element (e.g., a permanent magnet) that generates a magnetic field that attracts the ferromagnetic or ferrimagnetic material.

In some surgical procedures, or at times during a surgical procedure, it may be desirable for the grasper to move to and/or be held in a perpendicular or angled configuration with respect to the control element and/or the wall of a patient's body cavity (e.g., an abdominal cavity).

While the inventive devices, systems, and methods have been described in some detail by way of illustration, such illustration is for purposes of clarity of understanding only. It will be readily apparent to those of ordinary skill in the art in light of the teachings herein that certain changes and modifications may be made thereto without departing from the spirit and scope of the appended claims.

I claim:

1. A method for performing a surgical procedure, comprising:

introducing a grasper through an opening into an abdominal cavity;

grasping a portion of a first lobe of a liver with the grasper;

rotating the grasper towards a control element using a delivery device releasably coupled to the grasper, wherein the control element is located outside the abdominal cavity;

placing the control element adjacent to a body wall to apply a magnetic field to the grasper across the body wall; and folding a first portion of the liver over a second portion of the liver by moving the control element over a set of ribs such that the first portion anteriorly overlaps the second portion as the control element is being moved.

2. The method of claim 1, wherein the first portion comprises the first lobe and the second portion comprises a second lobe.

3. The method of claim 1, further comprising accessing a space in the abdominal cavity vacated by the grasped portion of the liver.

4. The method of claim 1, further comprising accessing a stomach in the abdominal cavity vacated by the grasped portion of the liver.

5. The method of claim 1, further comprising visualizing a stomach in the abdominal cavity vacated by the grasped portion of the liver using an optical sensor.

6. The method of claim 1, further comprising performing a gastric procedure while the liver forms the fold.

7. The method of claim 6, wherein the gastric procedure comprises one or more of a gastric bypass, a sleeve gastrectomy, a gastric band procedure, a biliopancreatic diversion with duodenal switch, and a gastric cancer resection.

8. The method of claim 1, wherein grasping the portion of the liver comprises grasping a peripheral edge of the liver.

9. The method of claim 1, wherein grasping the portion of the liver comprises grasping a left-lateral portion of segment II of the liver.

10. The method of claim 1, wherein grasping the portion of the first lobe comprises grasping an inferior portion of segment III of the liver.

11. A method for performing a surgical procedure, comprising:
- introducing a grasper through an opening into an abdominal cavity;
- grasping a portion of a first lobe of a liver with the grasper;
- rotating the grasper towards a control element using a delivery device releasably coupled to the grasper, wherein the control element is located outside the abdominal cavity;
- placing the control element adjacent to a body wall to apply a magnetic field to the grasper across the body wall; and
- moving the control element in a lateral direction with respect to a patient over a set of ribs such that the liver folds over itself as the control element is being moved.

12. The method of claim 11, wherein moving the magnetic control element over the set of ribs pulls grasped tissue away from the opening.

13. The method of claim 11, wherein moving the magnetic control element over the set of ribs moves the control element in a lateral direction with respect to the patient.

14. The method of claim 11, wherein moving the magnetic control element over the set of ribs moves the grasped portion of the liver anteriorly over a right lobe of the liver such that the liver forms the fold.

15. The method of claim 11, wherein moving the magnetic control element is performed in a left-superior direction over the set of ribs.

* * * * *